US012697610B2

(12) United States Patent
Handique et al.

(10) Patent No.: US 12,697,610 B2
(45) **Date of Patent: \*Aug. 4, 2026**

(54) SYSTEM AND METHOD FOR TARGET MATERIAL RETRIEVAL FROM MICROWELLS

(71) Applicant: Bio-Rad Laboratories, Inc., Hercules, CA (US)

(72) Inventors: Kalyan Handique, Ann Arbor, MI (US); Swati Ranade, Hercules, CA (US); Vishal Sharma, Hercules, CA (US); Austin Payne, Ypsilanti, MI (US); Sam Tuck, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/381,818

(22) Filed: Oct. 19, 2023

(65) Prior Publication Data

US 2024/0066519 A1      Feb. 29, 2024

Related U.S. Application Data

(63) Continuation of application No. 17/590,543, filed on Feb. 1, 2022, now Pat. No. 11,833,507, which is a (Continued)

(51) Int. Cl.
*B01L 3/00* (2006.01)
*C12N 13/00* (2006.01)

(52) U.S. Cl.
CPC ............... *B01L 3/502* (2013.01); *C12N 13/00* (2013.01); *B01L 2200/026* (2013.01); *B01L 2300/0893* (2013.01); *B01L 2400/043* (2013.01)

(58) Field of Classification Search
None
See application file for complete search history.

(56) References Cited

U.S. PATENT DOCUMENTS

| | | | |
|---|---|---|---|
| 4,475,411 A | 10/1984 | Wellerfors | |
| 4,551,435 A | 11/1985 | Liberti et al. | |

(Continued)

FOREIGN PATENT DOCUMENTS

| | | |
|---|---|---|
| CN | 202011883 U | 10/2011 |
| CN | 103894248 A | 7/2014 |

(Continued)

OTHER PUBLICATIONS

"High-throughput imaging of a unique continuous flow microfluidics plate", Scikon Innovation, Application Note, May 2016, https://www.moleculardevices.com/en/assets/app-note/dd/img/high-throughput-imaging-of-a-unique-continuous-flow-microfluidics-plate#gref.

(Continued)

*Primary Examiner* — P. Kathryn Wright
(74) *Attorney, Agent, or Firm* — Thomas C. Meyers; Sullivan & Worcester LLP

(57) ABSTRACT

A system and method for target material retrieval and processing, the system comprising: an adaptor configured to interface with a capture region of a capture substrate for capturing particles in single-particle format within a set of wells, wherein the adaptor comprises a first region configured to interface with the capture region, a second region, and a cavity extending from the first region to the second region; and a support structure coupled to the adaptor and providing a set of operation modes for movement of the adaptor relative to the capture substrate. The system enables methods for magnetic and/or other force-based methods of retrieval of target material (e.g., derived from single cells).

8 Claims, 45 Drawing Sheets

Related U.S. Application Data continuation of application No. 16/906,337, filed on Jun. 19, 2020, now Pat. No. 11,273,439, which is a continuation-in-part of application No. 16/867,235, filed on May 5, 2020, now Pat. No. 10,900,032.

(60) Provisional application No. 62/866,726, filed on Jun. 26, 2019, provisional application No. 62/844,470, filed on May 7, 2019.

(56) References Cited

U.S. PATENT DOCUMENTS

| | | | |
|---|---|---|---|
| 4,710,635 A | 12/1987 | Chupp |
| 5,266,269 A | 11/1993 | Niiyama et al. |
| 5,281,540 A | 1/1994 | Merkh et al. |
| 5,491,343 A | 2/1996 | Brooker |
| 5,541,064 A | 7/1996 | Bacus et al. |
| 5,547,849 A | 8/1996 | Baer et al. |
| 5,785,044 A | 7/1998 | Meador et al. |
| 5,851,488 A | 12/1998 | Saul et al. |
| 5,883,370 A | 3/1999 | Walker et al. |
| 5,888,370 A | 3/1999 | Becker et al. |
| 5,993,630 A | 11/1999 | Becker et al. |
| 5,993,632 A | 11/1999 | Becker et al. |
| 6,016,712 A | 1/2000 | Warden et al. |
| 6,127,177 A | 10/2000 | Toner et al. |
| 6,133,030 A | 10/2000 | Bhatia et al. |
| 6,150,180 A | 11/2000 | Parce et al. |
| 6,174,683 B1 | 1/2001 | Hahn |
| 6,221,663 B1 | 4/2001 | Bhatia et al. |
| 6,228,624 B1 | 5/2001 | Terstappen |
| 6,281,008 B1 | 8/2001 | Komai et al. |
| 6,287,832 B1 | 9/2001 | Becker et al. |
| 6,365,362 B1 | 4/2002 | Terstappen et al. |
| 6,410,724 B1 | 6/2002 | Dejean et al. |
| 6,433,134 B1 | 8/2002 | Patron et al. |
| 6,468,810 B1 | 10/2002 | Korpela |
| 6,525,997 B1 | 2/2003 | Narayanaswami et al. |
| 6,551,841 B1 | 4/2003 | Wilding et al. |
| 6,563,634 B2 | 5/2003 | Shimada et al. |
| 6,613,525 B2 | 9/2003 | Nelson et al. |
| 6,623,983 B1 | 9/2003 | Terstappen et al. |
| 6,641,708 B1 | 11/2003 | Becker et al. |
| 6,645,731 B2 | 11/2003 | Terstappen et al. |
| 6,692,952 B1 | 2/2004 | Braff et al. |
| 6,790,330 B2 | 9/2004 | Gascoyne et al. |
| 6,821,484 B1 | 11/2004 | Gregersen |
| 6,861,259 B2 | 3/2005 | Columbus |
| 6,866,823 B2 | 3/2005 | Wardlaw |
| 6,960,449 B2 | 11/2005 | Wang et al. |
| 7,008,789 B2 | 3/2006 | Gambini et al. |
| 7,035,170 B2 | 4/2006 | Narayanaswami et al. |
| 7,046,357 B2 | 5/2006 | Weinberger et al. |
| 7,148,492 B2 | 12/2006 | Loney et al. |
| 7,172,866 B2 | 2/2007 | Hahn et al. |
| 7,198,901 B1 | 4/2007 | Rachlin |
| 7,217,520 B2 | 5/2007 | Tsinberg et al. |
| 7,238,521 B2 | 7/2007 | Hahn et al. |
| 7,248,352 B2 | 7/2007 | Hamamatsu et al. |
| 7,258,990 B2 | 8/2007 | Falcovitz-Gerassi et al. |
| 7,266,777 B2 | 9/2007 | Scott et al. |
| 7,294,468 B2 | 11/2007 | Bell et al. |
| 7,316,897 B2 | 1/2008 | Bisconte et al. |
| 7,332,288 B2 | 2/2008 | Terstappen et al. |
| 7,338,760 B2 | 3/2008 | Gong et al. |
| 7,354,389 B2 | 4/2008 | Kureshy et al. |
| 7,439,062 B2 | 10/2008 | Bhatt et al. |
| 7,449,558 B2 | 11/2008 | Yao et al. |
| 7,449,778 B2 | 11/2008 | Sander |
| 7,501,283 B2 | 3/2009 | Hersch et al. |
| 7,507,528 B2 | 3/2009 | Albert et al. |
| 7,588,672 B2 | 9/2009 | Unger et al. |
| 7,595,157 B2 | 9/2009 | Tsinberg |
| 7,597,528 B2 | 10/2009 | Rodi |
| 7,604,777 B2 | 10/2009 | Columbus |
| 7,638,464 B2 | 12/2009 | Fagnani et al. |
| 7,695,956 B2 | 4/2010 | Tsinberg et al. |
| 7,704,322 B2 | 4/2010 | Hansen et al. |
| 7,710,563 B2 | 5/2010 | Betzig et al. |
| 7,738,320 B2 | 6/2010 | Taha |
| 7,763,704 B2 | 7/2010 | Ding et al. |
| 7,767,152 B2 | 8/2010 | Stead et al. |
| 7,815,863 B2 | 10/2010 | Kagan et al. |
| 7,858,757 B2 | 12/2010 | Hollmann et al. |
| 7,863,012 B2 | 1/2011 | Rao et al. |
| 7,901,950 B2 | 3/2011 | Connelly et al. |
| 7,964,349 B2 | 6/2011 | Bell et al. |
| 8,008,032 B2 | 8/2011 | Forsyth et al. |
| 8,013,298 B2 | 9/2011 | Khursheed |
| 8,021,614 B2 | 9/2011 | Huang et al. |
| 8,062,883 B2 | 11/2011 | Woudenberg et al. |
| 8,103,080 B2 | 1/2012 | George et al. |
| 8,105,769 B2 | 1/2012 | Bell et al. |
| 8,105,780 B2 | 1/2012 | Su et al. |
| 8,131,053 B2 | 3/2012 | Ortyn et al. |
| 8,158,410 B2 | 4/2012 | Tang et al. |
| 8,174,698 B2 | 5/2012 | Peter et al. |
| 8,175,371 B2 | 5/2012 | George et al. |
| 8,186,913 B2 | 5/2012 | Toner et al. |
| 8,211,301 B2 | 7/2012 | Safar et al. |
| 8,232,112 B2 | 7/2012 | Willson et al. |
| 8,252,517 B2 | 8/2012 | Thomas et al. |
| 8,293,524 B2 | 10/2012 | Ionescu-Zanetti et al. |
| 8,304,230 B2 | 11/2012 | Toner et al. |
| 8,329,422 B2 | 12/2012 | Rao et al. |
| 8,372,579 B2 | 2/2013 | Toner et al. |
| 8,372,584 B2 | 2/2013 | Shoemaker et al. |
| 8,406,498 B2 | 3/2013 | Ortyn et al. |
| 8,465,916 B2 | 6/2013 | Bell et al. |
| 8,628,923 B2 | 1/2014 | Hamilton et al. |
| 8,658,418 B2 | 2/2014 | Daridon |
| 8,680,025 B2 | 3/2014 | Cooney |
| 8,730,479 B2 | 5/2014 | Ness et al. |
| 8,765,454 B2 | 7/2014 | Zhou et al. |
| 8,771,609 B2 | 7/2014 | Ehben et al. |
| 8,802,367 B2 | 8/2014 | Taniguchi et al. |
| 8,936,945 B2 | 1/2015 | Handique et al. |
| 8,986,988 B2 | 3/2015 | Karnik et al. |
| 9,103,754 B2 | 8/2015 | Handique et al. |
| 9,110,026 B2 | 8/2015 | Collins |
| 9,133,499 B2 | 9/2015 | Di Carlo et al. |
| 9,145,540 B1 | 9/2015 | Deutsch et al. |
| 9,174,216 B2 | 11/2015 | Handique et al. |
| 9,188,586 B2 | 11/2015 | Fan et al. |
| 9,194,001 B2 | 11/2015 | Brenner |
| 9,200,245 B2 | 12/2015 | Deutsch et al. |
| 9,201,060 B2 | 12/2015 | Voldman et al. |
| 9,249,459 B2 | 2/2016 | Hamilton et al. |
| 9,260,753 B2 | 2/2016 | Xie et al. |
| 9,278,355 B2 | 3/2016 | Kajiyama et al. |
| 9,290,808 B2 | 3/2016 | Fodor et al. |
| 9,290,809 B2 | 3/2016 | Fodor et al. |
| 9,304,065 B2 | 4/2016 | Fowler et al. |
| 9,315,768 B2 | 4/2016 | Vrouwe et al. |
| 9,315,857 B2 | 4/2016 | Fu et al. |
| 9,329,170 B2 | 5/2016 | Clarke et al. |
| 9,364,829 B2 | 6/2016 | Heid et al. |
| 9,410,201 B2 | 8/2016 | Hindson et al. |
| 9,429,500 B2 | 8/2016 | Fowler et al. |
| 9,506,845 B2 | 11/2016 | Fowler et al. |
| 9,507,609 B2 | 11/2016 | Glazer et al. |
| 9,513,195 B2 | 12/2016 | Handique et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,610,581 B2 | 4/2017 | Handique et al. |
| 9,637,799 B2 | 5/2017 | Fan et al. |
| 9,701,998 B2 | 7/2017 | Hindson et al. |
| 9,707,562 B2 | 7/2017 | Handique et al. |
| 9,708,659 B2 | 7/2017 | Fodor et al. |
| 9,746,413 B2 | 8/2017 | Handique et al. |
| 9,752,181 B2 | 9/2017 | Handique et al. |
| 9,757,707 B2 | 9/2017 | Husain et al. |
| 9,802,193 B2 | 10/2017 | Handique et al. |

(56)　　　　　References Cited

U.S. PATENT DOCUMENTS

| | | |
|---|---|---|
| 9,840,732 B2 | 12/2017 | Anderson et al. |
| 9,845,502 B2 | 12/2017 | Fodor et al. |
| 9,850,483 B2 | 12/2017 | Clarke et al. |
| 9,952,126 B2 | 4/2018 | Fowler et al. |
| 9,995,662 B2 | 6/2018 | Husain et al. |
| 10,376,889 B1 | 8/2019 | Masquelier et al. |
| 10,391,490 B2 | 8/2019 | Handique et al. |
| 10,391,492 B2 | 8/2019 | Handique et al. |
| 10,391,493 B2 | 8/2019 | Handique et al. |
| 10,401,373 B1 | 9/2019 | Holmes et al. |
| 10,408,736 B1 | 9/2019 | Handique |
| 10,466,160 B2 | 11/2019 | Handique et al. |
| 10,533,152 B1 | 1/2020 | Belgrader et al. |
| 10,633,693 B1* | 4/2020 | Handique ............ C12Q 1/6874 |
| 10,718,007 B2 | 7/2020 | Handique et al. |
| 10,900,032 B2 | 1/2021 | Handique et al. |
| 11,273,439 B2 | 3/2022 | Handique et al. |
| 11,724,256 B2 | 8/2023 | Handique |
| 2002/0009759 A1 | 1/2002 | Terstappen et al. |
| 2002/0028431 A1 | 3/2002 | Julien |
| 2002/0036142 A1 | 3/2002 | Gascoyne et al. |
| 2002/0036823 A1 | 3/2002 | Shimada et al. |
| 2002/0098535 A1 | 7/2002 | Wang et al. |
| 2002/0109838 A1 | 8/2002 | Columbus |
| 2002/0119482 A1 | 8/2002 | Nelson et al. |
| 2002/0192808 A1 | 12/2002 | Gambini et al. |
| 2003/0096277 A1 | 5/2003 | Chen |
| 2003/0103662 A1 | 6/2003 | Finkbeiner |
| 2003/0129676 A1 | 7/2003 | Terstappen et al. |
| 2003/0138941 A1 | 7/2003 | Gong et al. |
| 2004/0029241 A1 | 2/2004 | Hahn et al. |
| 2004/0106130 A1 | 6/2004 | Besemer et al. |
| 2004/0109793 A1 | 6/2004 | McNeely et al. |
| 2004/0160599 A1 | 8/2004 | Hamamatsu et al. |
| 2004/0191891 A1 | 9/2004 | Tsinberg et al. |
| 2004/0218472 A1 | 11/2004 | Narayanaswami et al. |
| 2004/0229349 A1 | 11/2004 | Daridon |
| 2004/0239922 A1 | 12/2004 | Modlin et al. |
| 2004/0248318 A1 | 12/2004 | Weinberger et al. |
| 2005/0001176 A1 | 1/2005 | Loney et al. |
| 2005/0014201 A1 | 1/2005 | Deuthsch |
| 2005/0037343 A1 | 2/2005 | Fagnani et al. |
| 2005/0042685 A1 | 2/2005 | Albert et al. |
| 2005/0063863 A1 | 3/2005 | Columbus |
| 2005/0095582 A1 | 5/2005 | Gillim-Ross et al. |
| 2005/0105172 A1 | 5/2005 | Hasegawa et al. |
| 2005/0112589 A1 | 5/2005 | Hahn et al. |
| 2005/0118640 A1 | 6/2005 | Kureshy et al. |
| 2005/0123445 A1 | 6/2005 | Blecka et al. |
| 2005/0158804 A1 | 7/2005 | Yao et al. |
| 2005/0164236 A1 | 7/2005 | Su et al. |
| 2005/0181463 A1 | 8/2005 | Rao et al. |
| 2005/0214173 A1 | 9/2005 | Facer et al. |
| 2005/0265815 A1 | 12/2005 | Rodi |
| 2005/0277125 A1 | 12/2005 | Benn et al. |
| 2006/0037915 A1 | 2/2006 | Strand et al. |
| 2006/0040274 A1 | 2/2006 | Tsinberg |
| 2006/0040407 A1 | 2/2006 | Falcovitz-Gerassi et al. |
| 2006/0050142 A1 | 3/2006 | Scott et al. |
| 2006/0115380 A1 | 6/2006 | Kagan et al. |
| 2006/0128006 A1 | 6/2006 | Gerhardt et al. |
| 2006/0141045 A1 | 6/2006 | Bhatt et al. |
| 2006/0147959 A1 | 7/2006 | Bell et al. |
| 2006/0160243 A1 | 7/2006 | Tang et al. |
| 2006/0257992 A1 | 11/2006 | McDevitt et al. |
| 2006/0263250 A1 | 11/2006 | Blouin et al. |
| 2007/0025882 A1 | 2/2007 | Zuppiger et al. |
| 2007/0026381 A1 | 2/2007 | Huang et al. |
| 2007/0053800 A1 | 3/2007 | Lehto |
| 2007/0111302 A1 | 5/2007 | Handique et al. |
| 2007/0154960 A1 | 7/2007 | Connelly et al. |
| 2007/0161051 A1 | 7/2007 | Tsinberg et al. |
| 2007/0172903 A1 | 7/2007 | Toner et al. |
| 2007/0238089 A1 | 10/2007 | Rosenthal et al. |
| 2007/0243523 A1 | 10/2007 | Ionescu-Zanetti et al. |
| 2007/0252265 A1 | 11/2007 | Sander |
| 2007/0264675 A1 | 11/2007 | Toner et al. |
| 2007/0264705 A1 | 11/2007 | Dodgson |
| 2007/0275418 A1 | 11/2007 | Hollmann et al. |
| 2008/0003224 A1 | 1/2008 | Fong et al. |
| 2008/0014589 A1 | 1/2008 | Link et al. |
| 2008/0020453 A1 | 1/2008 | Ehben et al. |
| 2008/0038231 A1 | 2/2008 | Rodgerson et al. |
| 2008/0068588 A1 | 3/2008 | Hess et al. |
| 2008/0090239 A1 | 4/2008 | Shoemaker et al. |
| 2008/0096212 A1 | 4/2008 | Bell et al. |
| 2008/0113358 A1 | 5/2008 | Kapur et al. |
| 2008/0113906 A1 | 5/2008 | Ding et al. |
| 2008/0124726 A1 | 5/2008 | Monforte |
| 2008/0182273 A1 | 7/2008 | Hansen et al. |
| 2008/0206751 A1 | 8/2008 | Squirrell et al. |
| 2008/0207615 A1 | 8/2008 | Bell et al. |
| 2008/0220422 A1 | 9/2008 | Shoemaker et al. |
| 2008/0234264 A1 | 9/2008 | Bell et al. |
| 2008/0240539 A1 | 10/2008 | George et al. |
| 2008/0248043 A1 | 10/2008 | Babcook et al. |
| 2008/0257735 A1 | 10/2008 | Jeon et al. |
| 2008/0317325 A1 | 12/2008 | Ortyn et al. |
| 2009/0014360 A1 | 1/2009 | Toner et al. |
| 2009/0061450 A1 | 3/2009 | Hunter |
| 2009/0075361 A1 | 3/2009 | DeLouise et al. |
| 2009/0081773 A1 | 3/2009 | Kaufman |
| 2009/0141593 A1 | 6/2009 | Taha |
| 2009/0153844 A1 | 6/2009 | Peter et al. |
| 2009/0158823 A1 | 6/2009 | Kaduchak et al. |
| 2009/0162853 A1 | 6/2009 | Clark et al. |
| 2009/0215088 A1 | 8/2009 | Forsyth et al. |
| 2009/0220979 A1 | 9/2009 | Davis et al. |
| 2009/0221059 A1 | 9/2009 | Williams et al. |
| 2009/0258383 A1 | 10/2009 | Kovac et al. |
| 2009/0275115 A1 | 11/2009 | Jury et al. |
| 2009/0317836 A1 | 12/2009 | Kuhn et al. |
| 2010/0087325 A1 | 4/2010 | Buermann |
| 2010/0120077 A1 | 5/2010 | Daridon |
| 2010/0127168 A1 | 5/2010 | Khursheed |
| 2010/0210009 A1 | 8/2010 | Willson et al. |
| 2010/0227387 A1 | 9/2010 | Safar et al. |
| 2010/0232675 A1 | 9/2010 | Ortyn et al. |
| 2010/0233693 A1 | 9/2010 | Kopf-Sill et al. |
| 2010/0255471 A1 | 10/2010 | Clarke et al. |
| 2010/0261179 A1 | 10/2010 | Betley et al. |
| 2010/0291584 A1 | 11/2010 | Tseng et al. |
| 2010/0304485 A1 | 12/2010 | Karnik et al. |
| 2010/0304978 A1 | 12/2010 | Robbins et al. |
| 2011/0003380 A1 | 1/2011 | Miltenyi et al. |
| 2011/0005932 A1 | 1/2011 | Jovanovich et al. |
| 2011/0030808 A1 | 2/2011 | Chiou et al. |
| 2011/0045994 A1 | 2/2011 | Voldman et al. |
| 2011/0053151 A1 | 3/2011 | Hansen et al. |
| 2011/0053152 A1 | 3/2011 | Goldkorn et al. |
| 2011/0104718 A1 | 5/2011 | Rao et al. |
| 2011/0117634 A1 | 5/2011 | Halamish et al. |
| 2011/0143964 A1 | 6/2011 | Zhou et al. |
| 2011/0220567 A1 | 9/2011 | Kreuwel et al. |
| 2011/0227558 A1 | 9/2011 | Mannion et al. |
| 2011/0236904 A1 | 9/2011 | Hauch et al. |
| 2011/0280467 A1 | 11/2011 | George et al. |
| 2012/0021456 A1 | 1/2012 | Levine et al. |
| 2012/0071355 A9 | 3/2012 | Cooney |
| 2012/0071643 A1 | 3/2012 | Helfer et al. |
| 2012/0129190 A1 | 5/2012 | Chiu et al. |
| 2012/0152369 A1 | 6/2012 | Hiddessen et al. |
| 2012/0156675 A1 | 6/2012 | Lueerssen et al. |
| 2012/0164679 A1 | 6/2012 | Vrouwe et al. |
| 2012/0194805 A1 | 8/2012 | Ness et al. |
| 2012/0270310 A1 | 10/2012 | Spence et al. |
| 2012/0309104 A1 | 12/2012 | Uematsu et al. |
| 2012/0316074 A1 | 12/2012 | Saxonov |
| 2013/0011832 A1 | 1/2013 | Moreno et al. |
| 2013/0116102 A1 | 5/2013 | Hansen |
| 2013/0130376 A1 | 5/2013 | Serobyan et al. |
| 2013/0136670 A1 | 5/2013 | Wiltsie |
| 2013/0140183 A1 | 6/2013 | Tajima |
| 2013/0142711 A1 | 6/2013 | Wilson et al. |

(56) References Cited

U.S. PATENT DOCUMENTS

| 2013/0171628 A1 | 7/2013 | Di et al. |
| 2013/0171728 A1 | 7/2013 | Simard |
| 2013/0183660 A1 | 7/2013 | Yu et al. |
| 2013/0190212 A1 | 7/2013 | Handique et al. |
| 2013/0203634 A1 | 8/2013 | Jovanovich et al. |
| 2013/0210126 A1 | 8/2013 | Williams et al. |
| 2013/0210127 A1 | 8/2013 | Williams et al. |
| 2013/0230860 A1 | 9/2013 | Park et al. |
| 2013/0244906 A1 | 9/2013 | Collins |
| 2013/0259635 A1 | 10/2013 | Maslana et al. |
| 2013/0287645 A1 | 10/2013 | Shaikh et al. |
| 2013/0309778 A1 | 11/2013 | Lowe et al. |
| 2014/0030717 A1 | 1/2014 | Zhong et al. |
| 2014/0051595 A1 | 2/2014 | So |
| 2014/0087370 A1 | 3/2014 | Maeshima |
| 2014/0155295 A1 | 6/2014 | Hindson et al. |
| 2014/0161686 A1 | 6/2014 | Bort et al. |
| 2014/0173443 A1 | 6/2014 | Hawkins et al. |
| 2014/0212881 A1 | 7/2014 | Handique et al. |
| 2014/0213487 A1 | 7/2014 | Freudenthal et al. |
| 2014/0220617 A1 | 8/2014 | Yung et al. |
| 2014/0272965 A1 | 9/2014 | Handique et al. |
| 2014/0276216 A1 | 9/2014 | Lipinsky et al. |
| 2014/0315237 A1 | 10/2014 | Masujima et al. |
| 2014/0329301 A1 | 11/2014 | Handique |
| 2014/0357511 A1 | 12/2014 | Handique et al. |
| 2014/0370612 A1 | 12/2014 | Bassler et al. |
| 2015/0011432 A1 | 1/2015 | Saxonov |
| 2015/0056663 A1 | 2/2015 | Tajima et al. |
| 2015/0089359 A1 | 3/2015 | Brisebois |
| 2015/0093306 A1 | 4/2015 | Thorne et al. |
| 2015/0133319 A1 | 5/2015 | Fu et al. |
| 2015/0160135 A1 | 6/2015 | Tibbe et al. |
| 2015/0160931 A1 | 6/2015 | Glazer et al. |
| 2015/0204864 A1 | 7/2015 | Fan et al. |
| 2015/0225714 A1* | 8/2015 | Takahashi ............ B03C 1/0332 |
| | | 422/527 |
| 2015/0253251 A1 | 9/2015 | Mckee et al. |
| 2015/0299784 A1 | 10/2015 | Fan et al. |
| 2015/0376609 A1 | 12/2015 | Hindson et al. |
| 2016/0008814 A1 | 1/2016 | Handique et al. |
| 2016/0023213 A1 | 1/2016 | Richardson |
| 2016/0024572 A1 | 1/2016 | Shishkin et al. |
| 2016/0024761 A1 | 1/2016 | Korb |
| 2016/0053253 A1 | 2/2016 | Salathia et al. |
| 2016/0060621 A1 | 3/2016 | Agresti et al. |
| 2016/0108464 A1 | 4/2016 | Saxonov et al. |
| 2016/0130649 A1 | 5/2016 | Xie et al. |
| 2016/0199838 A1 | 7/2016 | Handique et al. |
| 2016/0202157 A1 | 7/2016 | Fawcett et al. |
| 2016/0209319 A1 | 7/2016 | Adalsteinsson et al. |
| 2016/0251714 A1 | 9/2016 | Conant et al. |
| 2016/0289669 A1 | 10/2016 | Fan et al. |
| 2016/0314242 A1 | 10/2016 | Schnall-Levin et al. |
| 2016/0367991 A1 | 12/2016 | Petersen et al. |
| 2017/0044525 A1 | 2/2017 | Kaper et al. |
| 2017/0052205 A1 | 2/2017 | Silbert |
| 2017/0073405 A1 | 3/2017 | Fuh et al. |
| 2017/0153219 A1 | 6/2017 | Handique et al. |
| 2017/0276682 A1* | 9/2017 | Park ................. G01N 33/57492 |
| 2017/0307502 A1 | 10/2017 | Mason et al. |
| 2017/0320038 A1 | 11/2017 | Husain et al. |
| 2017/0321252 A1 | 11/2017 | Hindson et al. |
| 2017/0335385 A1 | 11/2017 | Hindson et al. |
| 2017/0356027 A1 | 12/2017 | Hindson et al. |
| 2017/0370951 A1 | 12/2017 | Buffiere et al. |
| 2018/0030515 A1 | 2/2018 | Regev et al. |
| 2018/0036731 A1 | 2/2018 | Handique et al. |
| 2018/0037942 A1 | 2/2018 | Fu |
| 2018/0051321 A1 | 2/2018 | Hindson et al. |
| 2018/0080075 A1 | 3/2018 | Brenner et al. |
| 2018/0088112 A1 | 3/2018 | Fan et al. |
| 2018/0094298 A1 | 4/2018 | Hindson et al. |
| 2018/0094312 A1 | 4/2018 | Hindson et al. |
| 2018/0105808 A1 | 4/2018 | Mikkelsen et al. |
| 2018/0112266 A1 | 4/2018 | Hindson et al. |
| 2018/0127744 A1 | 5/2018 | Hu et al. |
| 2018/0127823 A1 | 5/2018 | Shekhar et al. |
| 2018/0272296 A1 | 9/2018 | Link et al. |
| 2018/0274027 A1 | 9/2018 | Hindson et al. |
| 2018/0282804 A1 | 10/2018 | Hindson et al. |
| 2018/0311636 A1 | 11/2018 | Jacobson et al. |
| 2018/0372741 A1 | 12/2018 | Matsumoto et al. |
| 2019/0002814 A1 | 1/2019 | Masquelier et al. |
| 2019/0060902 A1 | 2/2019 | Handique et al. |
| 2019/0064168 A1 | 2/2019 | Handique et al. |
| 2019/0106739 A1 | 4/2019 | Terbrueggen |
| 2019/0153532 A1 | 5/2019 | Bharadwaj et al. |
| 2019/0241944 A1 | 8/2019 | Cater et al. |
| 2019/0285644 A1 | 9/2019 | Regev et al. |
| 2019/0338353 A1 | 11/2019 | Belgrader et al. |
| 2020/0209229 A1 | 7/2020 | Strong et al. |
| 2020/0354715 A1* | 11/2020 | Handique ............. G01F 23/292 |
| 2021/0171939 A1 | 6/2021 | Mccoy et al. |
| 2021/0252509 A1 | 8/2021 | Szita et al. |

FOREIGN PATENT DOCUMENTS

| CN | 103998394 A | 8/2014 |
| CN | 104789468 A | 7/2015 |
| EP | 2414548 A2 | 2/2012 |
| EP | 2414548 B1 | 10/2015 |
| JP | 2006098696 A | 4/2006 |
| JP | 2008136415 A | 6/2008 |
| JP | 2009195160 A | 9/2009 |
| JP | 2010085343 A | 4/2010 |
| JP | 2011127965 A | 6/2011 |
| JP | 2011234671 A | 11/2011 |
| JP | 2013500496 A | 1/2013 |
| JP | 2013541959 A | 11/2013 |
| JP | 2015527588 A | 9/2015 |
| JP | 5998218 B2 | 9/2016 |
| JP | 2017063716 A | 4/2017 |
| JP | 2018508187 A | 3/2018 |
| JP | 2019516099 A | 6/2019 |
| WO | 9942832 A1 | 8/1999 |
| WO | 2003035909 A2 | 5/2003 |
| WO | 2006098696 A1 | 9/2006 |
| WO | 2007044917 A2 | 4/2007 |
| WO | 2008061165 A2 | 5/2008 |
| WO | 2009076560 A2 | 6/2009 |
| WO | 2010120818 A2 | 10/2010 |
| WO | 2010142954 A1 | 12/2010 |
| WO | 2011017094 A2 | 2/2011 |
| WO | 2011162290 A1 | 12/2011 |
| WO | 2012057548 A2 | 5/2012 |
| WO | 2013176767 A1 | 11/2013 |
| WO | 2014007074 A1 | 1/2014 |
| WO | 2015133337 A1 | 9/2015 |
| WO | 2015150278 A1 | 10/2015 |
| WO | 2016115025 A1 | 7/2016 |
| WO | 2016149639 A1 | 9/2016 |
| WO | 2016151719 A1 | 9/2016 |
| WO | 2016162997 A1 | 10/2016 |
| WO | 2016191533 A1 | 12/2016 |
| WO | 2017095917 A1 | 6/2017 |
| WO | 2017184242 A2 | 10/2017 |
| WO | 2018013723 A1 | 1/2018 |
| WO | 2018058073 A2 | 3/2018 |
| WO | 2019006436 A1 | 1/2019 |
| WO | 2019046307 A1 | 3/2019 |
| WO | 2019104337 A1 | 5/2019 |
| WO | 2019165318 A1 | 8/2019 |

OTHER PUBLICATIONS

Chen, H. , et al., "High-throughput, deterministic single cell trapping and long-term clonal cell culture in microfluidic devices", Lab Chip. Feb. 21, 2015;15(4):1072-83. doi: 10.1039/c41c01176g. PMID: 25519528.

Dura, Burak , et al., "scFTD-seq: freeze-thaw lysis based, portable approach toward highly distributed single-cell 3' mRNA profiling",

(56) References Cited

OTHER PUBLICATIONS

Nucleic Acids Research, 2019, vol. 47, No. 3, published online Nov. 20, 2018.

Guo, P., et al., "Microfluidic capture and release of bacteria in a conical nanopore array", Lab Chip. Vol. 12, p. 558-561, 2012, published online Nov. 2011.

Lindstrom, Sara , "Microwell devices for single-analyses", Royal Institute of Technology, Stockholm, Sweden, 2009, pp. 1-80., Feb. 12, 2018 00:00:00.0.

Murphy, Travis W., et al., "Recent advances in the use of microfluidic technologies for signs;e cell analysis", Analyst, Oct. 26, 2017, vol. 143, pp. 60-80.

Sarkar, S., et al., "Phenotypic drug profiling in droplet microfluidics for better targeting of drug-resistant tumors", Lab on a chip., vol. 15, 23 (2015): 4441-50. doi: 10.1039/c51c00923e.

Seale, K. T. , et al., "Mirrored pyramidal wells for simultaneous multiple vantage point microscop", Journal of Microscopy (2008) 232 1-6. (Year: 2008).

Shaminie, Jairaman , et al., "Improvement in the detection rate of t(14;18) translocation on paraffin-embedded tissue: combination approach using PCR and FISH", Pathology, Oct. 2003, 35(5), pp. 414-421.

Stahl, Patrik L., et al., "Visualization and analysis of gene expression in tissue sections by spatial transcriptomics", sciencemag.org, Jul. 2016, vol. 353, Issue 6294, pp. 78-82.

Sugio, Yoshihiro , et al., "An agar-based on-chip neural-cell-cultivation system for stepwise control of network pattern generation during cultivation", Sensors and Actuators B 99 2004 156-162., Feb. 12, 2018 00:00:00.0.

Tan, Wei-Heong , et al., "A trap-and-release integrated microfluidic system for dynamic microarray applications", PNAS, vol. 104 No. 4, Jan. 23, 2007, pp. 1145-1151.

Tan, Wei-Heong , et al., "Supplemental Information", PNAS, vol. 104, No. 4, Jan. 23, 2007.

Yeh, EC , et al., "Self-powered integrated microfluidic point-of-care low-cost enabling (SIMPLE) chip", Sci Adv. Mar. 2, 20172;3(3):e1501645. doi:10.1126/sciadv.1501645. PMID: 28345028; PMCID: PM 5362183.

Yuan, J. , et al., "An Automated Microwell Platform for Large-Scale Single Cell RNA-Seq.", Sci Rep. Sep. 27, 2016;6:33883. doi: 10.1038/srep33883. PMID: 27670648; PMCID: PMC5037380.

Yuan, Jinzhou , et al., "SCOPE-Seq: a scalable technology for linking live cell imaging and single-cell RNA sequencing", vol. 19, No. 227, Dec. 24, 2018, XP055680743, DOI: 10.1186/s13059-018-1607-x *Fig. 1; p. 3,. left col. "in SCOPE-Seg, we load . . . ."

* cited by examiner

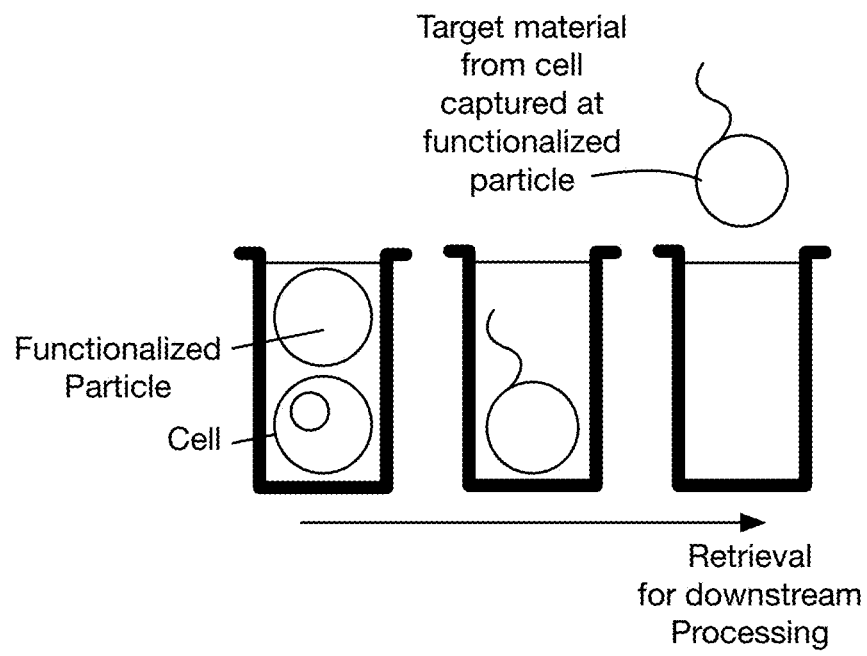
Target material
from cell
captured at
functionalized
particle
Functionalized
Particle
Cell
Retrieval
for downstream
Processing
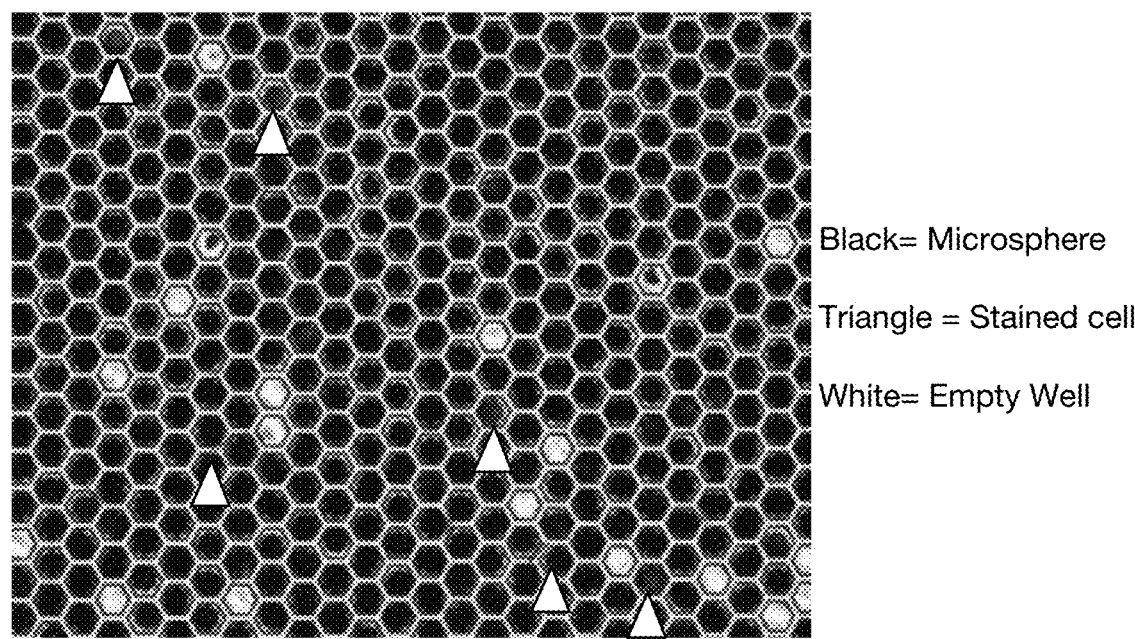
Black= Microsphere
Triangle = Stained cell
White= Empty Well
FIGURE 1B Sample Processing
Cartridge 130"

Cover
48
*

Lid
135

Inlet Reservoir
133

Base Substrate
131

Waste Containment
Region 137

Access Region
134

Sample Processing Chip
132

Opening
44

Valve
43

Inlet Reservoir
133

Lid
135

Waste Containment
Region 137

(TOP VIEW)

Inlet Opening
32

33

34

35

Outlet
Opening
36

Waste Outlet
51

Sample Processing Chip
132

(BOTTOM VIEW)

(ELEVATION VIEW,
CROSS-SECTION)

Process Container 20'

Fifth
Domain
25'

Third
Domain
23'

Second
Domain
22'

First
Domain
21'

Fourth
Domain
24'

System 200'

To Interface
of Pipettor 174

Interface
162

Support
Structure
240'

Magnet 230'

Adaptor 210'

Interface
162

Support
Structure
240'

Magnet
230'

Internal Cavity
220'

Protrusion
214'

2nd Region
212'

Adaptor 210'

1st Region
211'

(SIDE VIEW)

Fourth Operation
Mode 164d
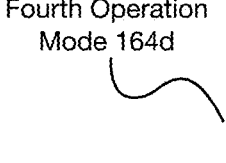
Actuator
Interface 6
Separation
Reservoir
<u>129</u>
Magnet
167b
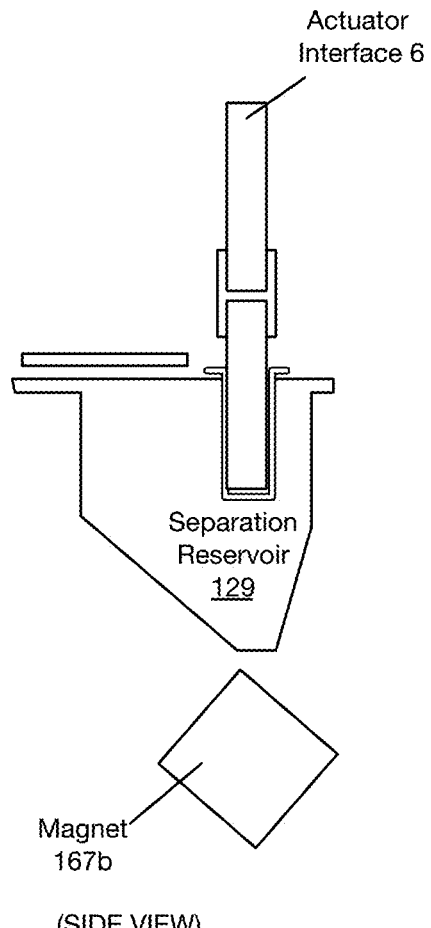
(SIDE VIEW)
FIGURE 11E Sixth Operation
Mode 164f
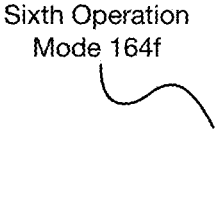
Actuator
Interface 6
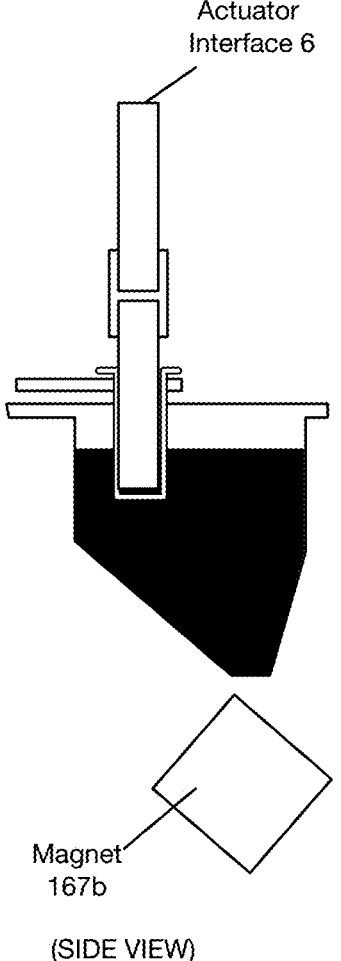
Magnet
167b
(SIDE VIEW)
FIGURE 11G Seventh Operation
Mode 164g Actuator
Interface 6

Magnet
167b (SIDE VIEW)

Actuator
Interface 6

Eighth Operation
Mode 164h

Magnet
167b (SIDE VIEW)

Ninth Operation
Mode 164i

Actuator
Interface 6

Magnet
167b (SIDE VIEW)

Process Container 20'

Adaptor 210'

Separation
Reservoir
129

Process Container 20'

300

Support
Structure
340

Protrusion 314

Adaptor
310

Set of Plugs
350

Guide 360

400

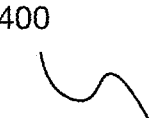

capturing a set of particles, in single-particle format, at a set of wells distributed across a substrate at a capture region  410 supporting an environment for processing target material of the set of particles within the capture region, according to a set of operations 420 forming an assembly with an adaptor configured to interact with the substrate 430 transmitting a force to the adaptor and the capture region, thereby releasing target material of the set of particles toward the adaptor  440 releasing target material of the set of particles for capture by the adaptor 450

FIGURE 14

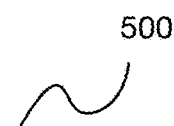
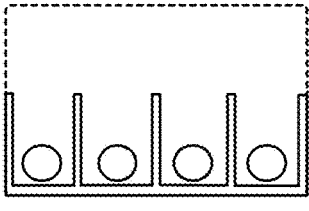
Non-magnetic bead for
Capturing biomarkers from single cells 510
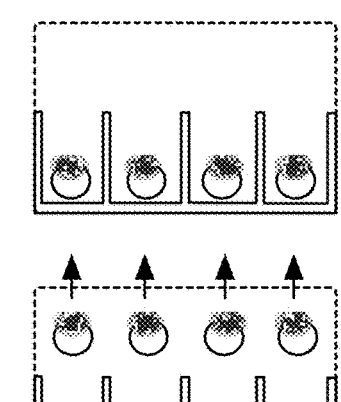
Bind magnetic beads through specific interactions
On non-magnetic beads 520
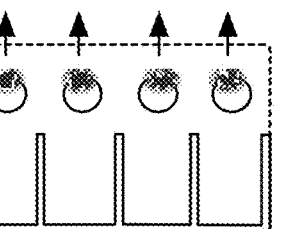
Apply magnetic force and remove beads from well 530
FIGURE 15A Co-capture single cells and barcoded beads 502

Link mRNA/protein to sequence on bead through RT/ligation 506

Retrieve by magnetic force 530

Lyse cells and transfer mRNA to beads 504

Add magnetic beads that bind to target beads 520

600

Template switching oligonucleotide for complete capture of 5' ends using template switching mechanism of MMLV RT enzyme 740
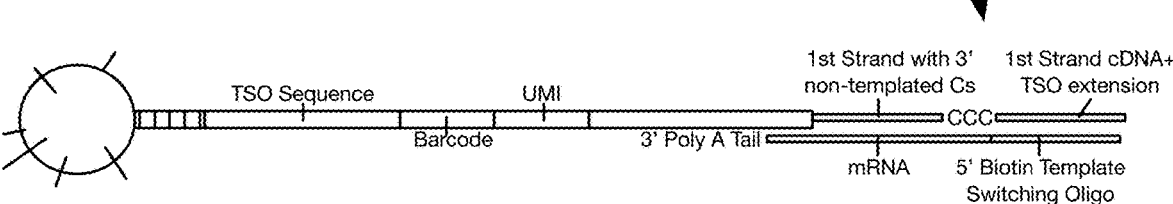
Binding productive beads in the wells to magnetic beads 750
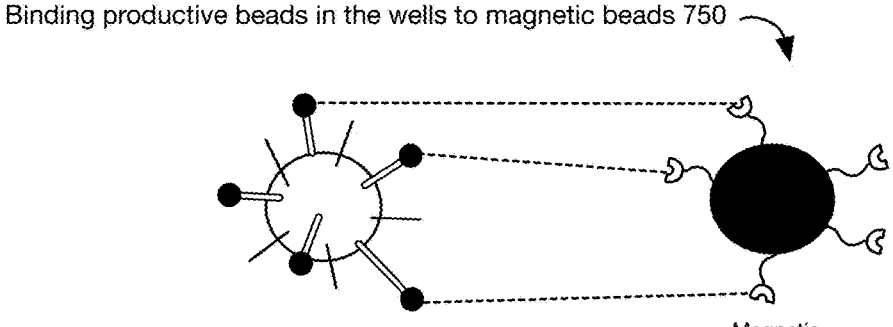
FIGURE 17B Pull out non-magnetic beads bound to magnetic beads, with magnetic force 760 non-magnetic                                    Magnetic          magnetic
force Collect beads in process container for downstream processing 800
dU set
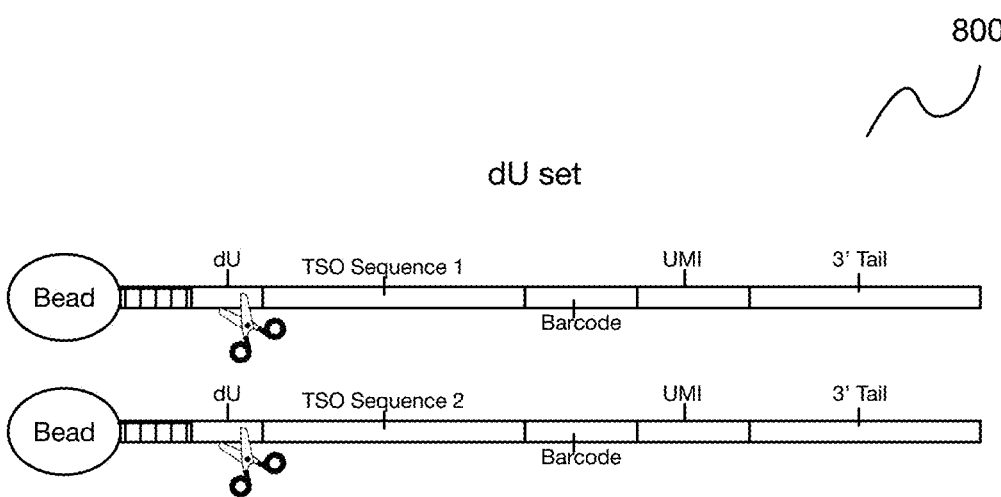
dSpacer set
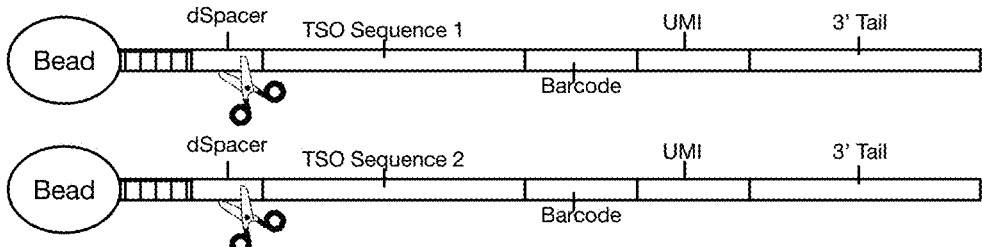
FIGURE 18A Bead loaded in well and hybridized to mRNA 810, 820
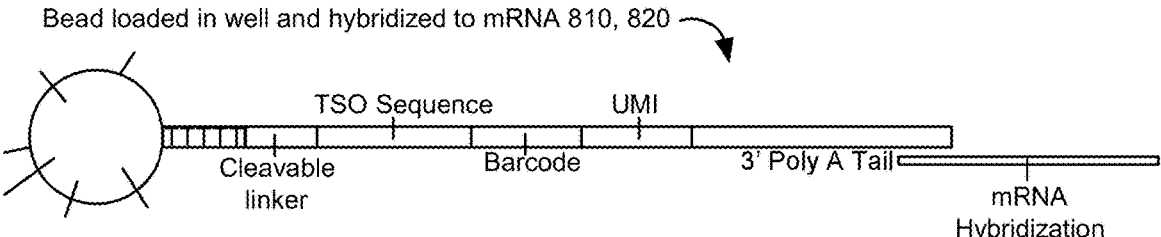
RT reaction 830
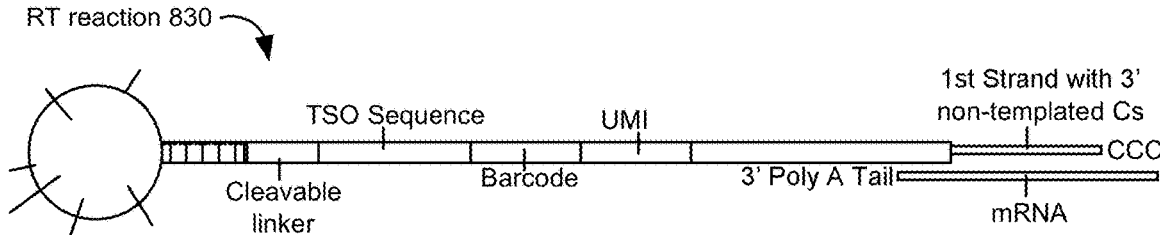
FIGURE 18B
Template switching oligonucleotide for complete capture of 5' ends using template switching mechanism of MMLV RT enzyme 840
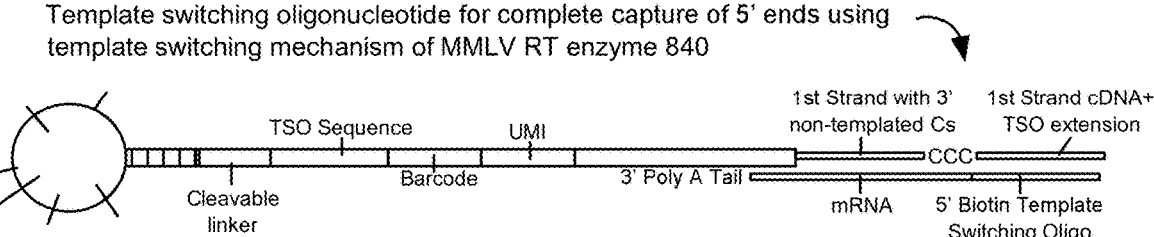
Release RNA-cDNA hybrids by restricting/cleaving linkers 850
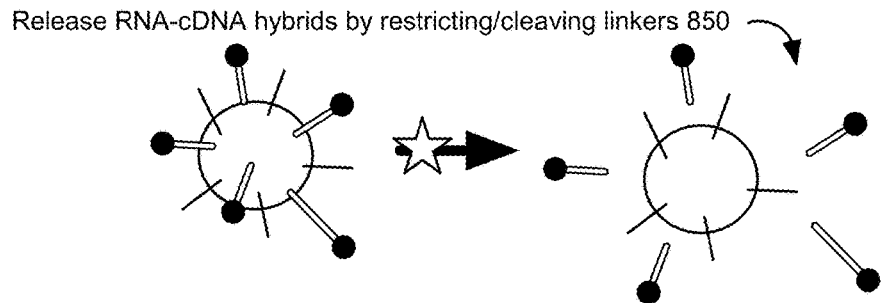
FIGURE 18C

Pull out targets bound to magnetic beads, with magnetic force 860 non-magnetic        Magnetic     magnetic force

Collect beads in process container for downstream processing

SYSTEM AND METHOD FOR TARGET MATERIAL RETRIEVAL FROM MICROWELLS

CROSS-REFERENCE TO RELATED APPLICATIONS

This application is a continuation of U.S. application Ser. No. 17/590,543, filed 1 Feb. 2022, which is a continuation of U.S. application Ser. No. 16/906,337, filed 19 Jun. 2020, which claims the benefit of U.S. Provisional Application No. 62/866,726, filed on 26 Jun. 2019, each of which is incorporated in its entirety herein by this reference.

U.S. application Ser. No. 16/906,337, filed 19 Jun. 2020, is a Continuation-in-part of U.S. application Ser. No. 16/867,235, filed 5 May 2020, which claims the benefit of U.S. Provisional Application Ser. No. 62/844,470, filed 7 May 2019, which are each incorporated in its entirety herein by this reference.

TECHNICAL FIELD

This invention relates generally to the cell capture and cell processing field, and more specifically to a new and useful system and method for target material retrieval in the cell capture and cell processing field.

BACKGROUND

With an increased interest in cell-specific drug testing, diagnosis, and other assays, systems and methods that allow for individual cell isolation, identification, and retrieval are becoming highly desirable. Single cell capture systems and methods have been shown to be particularly advantageous for these applications. However, associated processes and protocols for single cell capture and subsequent analysis must often be performed in a particular manner and with a high precision in order to properly maintain the cells. Furthermore, efficient retrieval of target material from high density platforms is subject to many challenges. As such, these processes can be time consuming for the user, require extensive and iterative manual library preparation and selection processes, not amenable to automation as well as result in damage to the cells or otherwise unfavorable results if they are not performed properly.

Thus, there is a need in the cell capture and cell processing field to create a new and useful system and method for sample processing and target material retrieval and minimize steps required in the library preparation of the target biomaterials.

BRIEF DESCRIPTION OF THE FIGURES

FIG. 1B depicts schematics of applications of an embodiment of a system for target material retrieval.

FIGS. 11A-11J depict operation modes of a separation subsystem associated with a system for target material retrieval and processing;

FIGS. 13A-31C depict a second variation of a system for target material retrieval.

FIG. 14 depicts a flowchart of an embodiment of a method for target material retrieval.

FIGS. 15A and 15B depict schematics of a variation of a method for target material retrieval.

FIG. 16 depicts a flowchart of a method for target material retrieval.

FIGS. 17A-17D depict schematics of a first example of a method for target material retrieval.

FIGS. 18A-18E depict a schematic of a second example of a method for target material retrieval.

FIG. 19 depicts a flow chart of a variation of a method for target material retrieval.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. BENEFITS

The system(s) and method(s) described can confer several benefits over conventional systems and methods.

The invention(s) confer(s) the benefit of providing mechanisms for efficient retrieval of target material (e.g., beads, cells, released nucleic acid material, etc.) from high-aspect ratio wells of a high-density capture platform. Retrieval is typically difficult and non-efficient in this scenario due to close packing of wells of the capture platform. Retrieval mechanisms described also subject target material to acceptable amounts of shear and other potential stresses that would otherwise obstruct downstream processing steps.

The invention(s) also confer(s) the benefit of reducing burden on system operators in relation to target material retrieval processes from wells, where standard processes can require repeating aspiration and dispensing steps that require additional time.

The invention(s) can also confer the benefit of increasing the efficiency at which target material is retrieved (and non-target material is not retrieved). Selective retrieval efficiency can thus reduce downstream costs in relation to processing reagent and other material costs (due to reduced volumes needed) and processing burden. For instance, the invention(s) can enable a system operator to purchase smaller volumes of reagents, reduce the number of splits required for successful amplification of target molecules and obviate the need for doing SPRI-based clean-up and size selection of target oligonucleotide products from other oligonucleotide tags that do not contain products, but get carried over from one process step to the next. Such improved recovery of target products and reduction of carryover of non-target products can also reduce the complexity of data analysis and also provide more useable data pertaining to the desired biomarker analysis as well. This can function to save costs, reduce reagent waste, or have any other suitable outcome.

The invention(s) also confer the benefit of enabling at least partial automation of the protocols involved in single cell capture, target material retrieval, and subsequent processing. For instance, a human operator user can be removed from part or all of the method, in relation to protocols involving repeated purification, washing, and retrieval steps. Furthermore, the system(s) and/or method(s) can enable better accuracy in performance of a protocol over conventional systems and methods. Some of these inventions are also much amenable to full automation with a liquid handling robot.

Additionally or alternatively, the system and/or method can confer any other suitable benefit.

2. SYSTEM

Figure 1A:
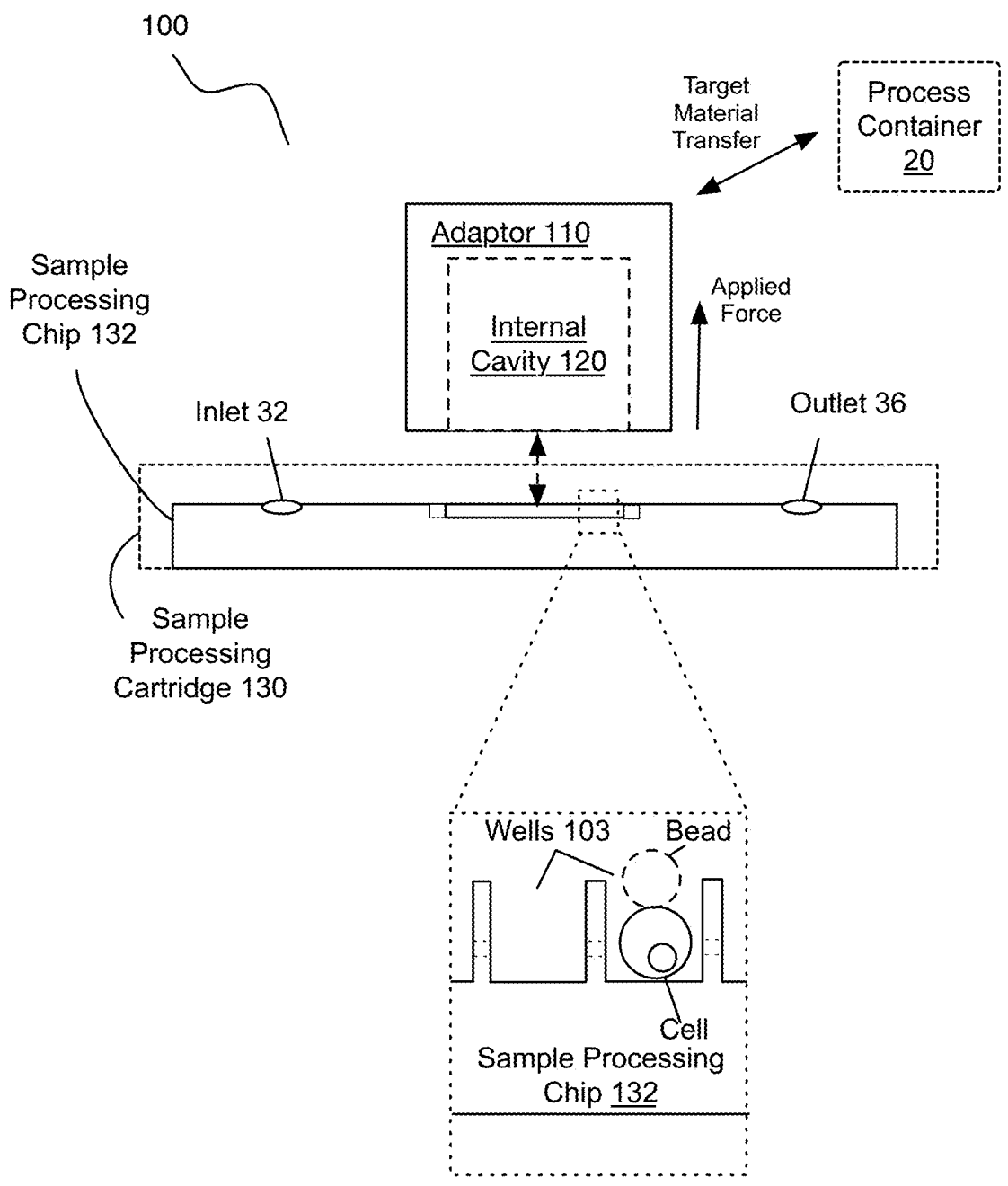
FIG. 1A depicts a schematic of an embodiment of a system for target material retrieval.

As shown in FIG. 1A, embodiments of a system 100 for target material retrieval include: an adaptor 110 configured to interface with/communicate with a capture region of a sample processing chip 132 for capturing particles in single-particle format within a set of wells, wherein the adaptor 110 can include a cavity 120 configured to, in response to an applied force, promote release of target material from the set of wells and into or to the adaptor no for efficient retrieval of target material from the chip 101. Applied forces are preferentially applied perpendicular)(90°±30° to the plane of the microwells. Embodiments of the system 100 function to provide mechanisms for efficient retrieval of target material from a high-density capture device (e.g., microwell chip), where the high-density capture device includes a high-density array of high-aspect ratio microwells, in order to promote increased efficiency in captured single cell-bead pairing efficiency. Embodiments of the system 100 can also function to reduce manual burden in relation to retrieval of target material from the high-density capture device. Embodiments of the system 100 can also function to increase the efficiency at which target material is retrieved from the high-density capture device, and the efficiency at which non-target material is retained at the capture device.

In an embodiment, as shown in FIG. 1B (top), a microwell of the high-density capture device can co-capture a functional particle with a single biological cell having target material. Then, the system can enable cell lysis and transfer of target materials to the functional particle within the microwell, and the system can enable performance of reverse transcription or ligation to link the target materials to an oligonucleotide tag on the functional particle. Then, the target material (and, in some embodiments, the functional particle) can be retrieved from the microwell. A specific example of the embodiment is shown in FIG. 1B (bottom), which depicts a top-down view of a high-density capture platform having an array of microwells, where some microwells contain a functional particle, some microwells contain a single cell, and some microwells are empty.

In relation to retrieval of target material in response to being subject to one or more applied forces, the applied forces can include one or more of: a magnetic force; a gravity-associated force (e.g., centrifugal force, buoyancy force, etc.); a fluid pressure-driven force produced by applying positive and/or negative pressure at the capture region (e.g., through an inlet channel of the chip 101, through an outlet channel of the chip 101, through an adaptor manifold coupled to the chip 101, etc.); an electric field-associated force (e.g., due to applied voltage); ultrasound force; acoustic force; photo-generated pressure force; laser-generated shock force and any other suitable force.

In an embodiment of a fluid pressure-driven mechanism, the system 100 can enable retrieval of target material from capture wells of the chip 101 with an adaptor 110 comprising structures for interacting with a pipettor, in a position where the aspirator is fluidly coupled to a fluid volume interfacing with the capture wells, and where the system 100 includes a first operation mode for dispensing fluid into the fluid volume and a second operation mode for aspirating fluid from the fluid volume. The first operation mode produces local convective forces at the capture wells for loosening and lifting material within the capture wells, and the second operation mode produces convective currents for delivery material from the capture wells into the aspirator, where target material can then be delivered to an elution container. The system 100 cycles between the first and the second operation modes to increase efficiency of target material from the capture wells. Variations of this embodiment can produce retrieved target material within 10-15 minutes of manual operation time, with a retrieval efficiency of 85-90% (in relation to percent of captured particles that are retrieved). Embodiments, variations, and examples of a fluid pressure-driven system and method are described in more detail in U.S. application Ser. No. 15/815,532 titled "System and Method for Retrieving and Analyzing Particles" and filed on 16 Nov. 2017, which is incorporated in its entirety herein by this reference.

Other embodiments, variations, and examples of systems associated with other forces are described in more detail in Sections 2.2 and 2.3 below. Furthermore, embodiments, variations, and examples of the system can be configured to implement embodiments, variations, and examples of the method(s) described in Section 3 below.

In relation to sample processing, embodiments of the system 100 can include or be configured to process cells, cell-derived material, and/or other biological material (e.g., cell-free nucleic acids). The cells can include any or all of mammalian cells (e.g., human cells, mouse cells, etc.), embryos, stem cells, plant cells, microbes (e.g., bacteria, virus, fungi, etc.) or any other suitable kind of cells. The cells can contain target material (e.g., target lysate, mRNA, RNA, DNA, proteins, glycans, metabolites, etc.) which originates within the cells and is optionally captured by the cell capture system for processing. Additionally, the containers containing the cells can be prepared from multiple cell-containing samples (e.g., 12 samples, 24 samples, 48 samples, 96 samples, 384 samples, 1536 samples, other numbers of samples), wherein the various samples are hashed or barcoded prior to mixing them together into a single container (or reduced number of containers). Multiple samples may be dispensed into the same microwell chip by dispensing into geographically-distinct locations of the chip. This feature enables automated processing of multiple samples in the same automated run for their respective single cell preparation and library preparation operations. Additionally or alternatively, the system 100 can be configured to interact with particles (e.g., beads, probes, nucleotides, oligonucleotides, polynucleotides, etc.), droplets, encapsulated cells, encapsulated biomarkers, reagents, or any other suitable materials.

The system 100 can further additionally or alternatively include any or all of the system components as described in U.S. application Ser. No. 16/890,417 filed 2 Jun. 2020; U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017, which are each incorporated in their entirety by this reference.

2.1 System—Sample Cartridge and Sample Processing Chip

As shown in FIGS. 1A and 2A-2C, the sample processing chip 132 functions to provide one or more sample processing regions in which cells are captured and optionally sorted, processed, or otherwise treated for downstream applications, where the downstream applications can be performed at a sample processing cartridge 130 supporting the sample processing chip 132 (e.g., on-chip) and/or away from the sample processing cartridge 130 (e.g., off-chip).

The sample processing cartridge 130 functions to support the sample processing chip 132, and to provide fluid pathways for fluid delivery, capture, and sample processing at the sample processing chip 132. The sample processing cartridge 130 can also function to facilitate heat transfer to and from the sample processing chip 132 in relation to sample processing procedures. Portions of the sample processing cartridge 130 can be configured within a single substrate, but can additionally or alternatively include multiple portions (e.g. connected by fluidic pathways) across multiple substrates.

As shown in FIGS. 2A-2D, an example of the sample processing cartridge 130' can include a base substrate 131 to which other elements are coupled and/or in which other elements are defined. Furthermore, in relation to sample processing involving microfluidic elements, the base substrate 131 can function as a manifold for fluid transfer to microfluidic elements, accessing of sample processing volumes at various stages of processing, and transfer of waste materials produced during sample processing. In variations, the base substrate 131 supports one or more of: the sample processing chip 132, an inlet reservoir 133 for receiving sample material (e.g., containing cells, containing particles, etc.) and delivering it into the sample processing chip 132, an access region 134 for accessing one or more regions of the sample processing chip 132, a lid 135 covering the access region and including a gasket 136 providing sealing functions, and a waste containment region 137 for receiving waste material from the sample processing chip 132. The cartridge may have additional gasketed ports to also connect with off-cartridge pumping systems. Variations of the base substrate 131 can, however, include other elements. For instance, as described in more detail below, the base substrate can include one or more openings, recesses, and/or protrusions that provide further coupling with the sample processing chip 132, in order to collectively define valve regions for opening and closing flow through the sample processing chip 132.

Figure 2A:
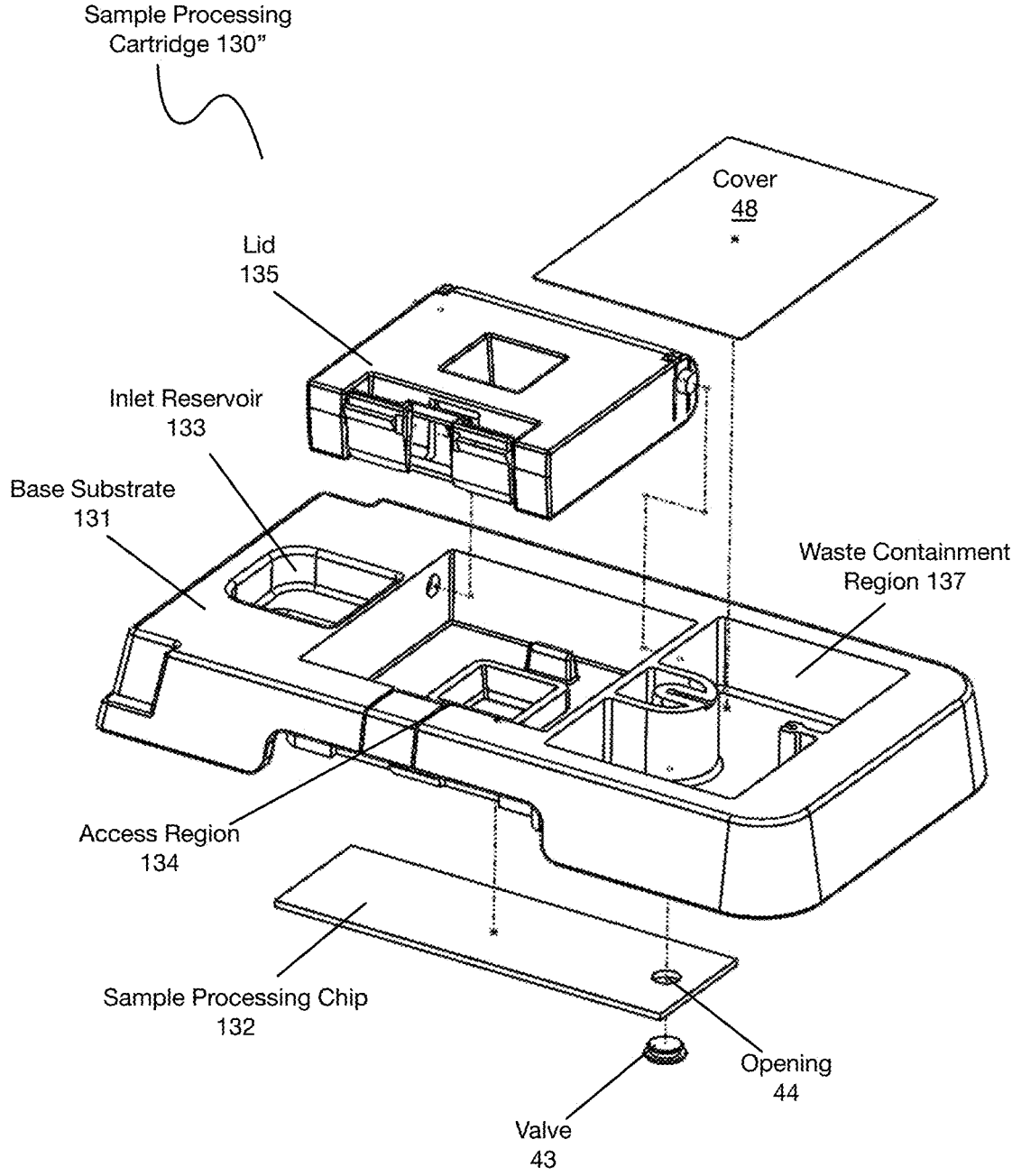
FIGS. 2A-2C depict views of a variation of a sample processing cartridge associated with a system for target material processing and retrieval.
Figure 2B:
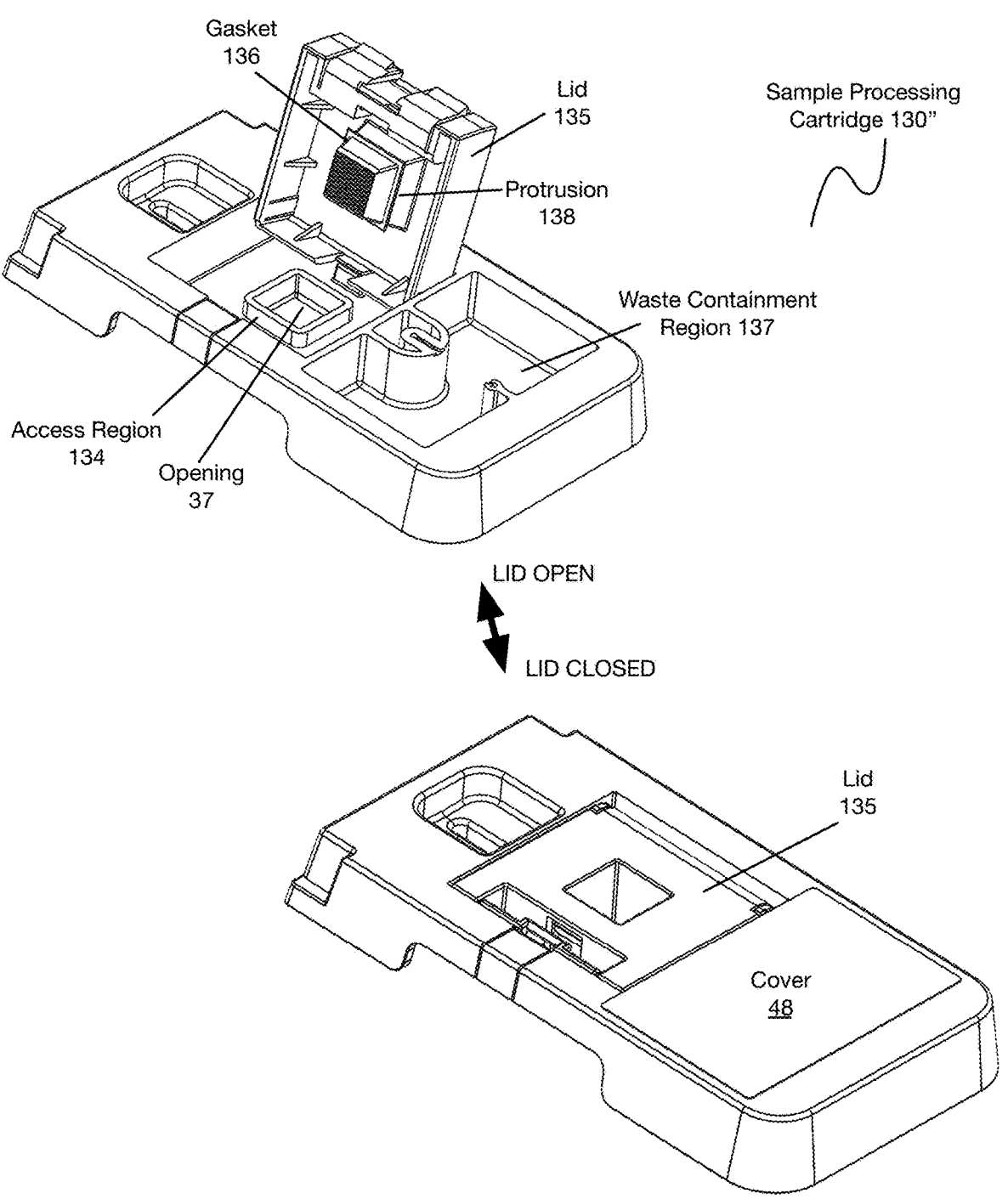
Figure 2C:
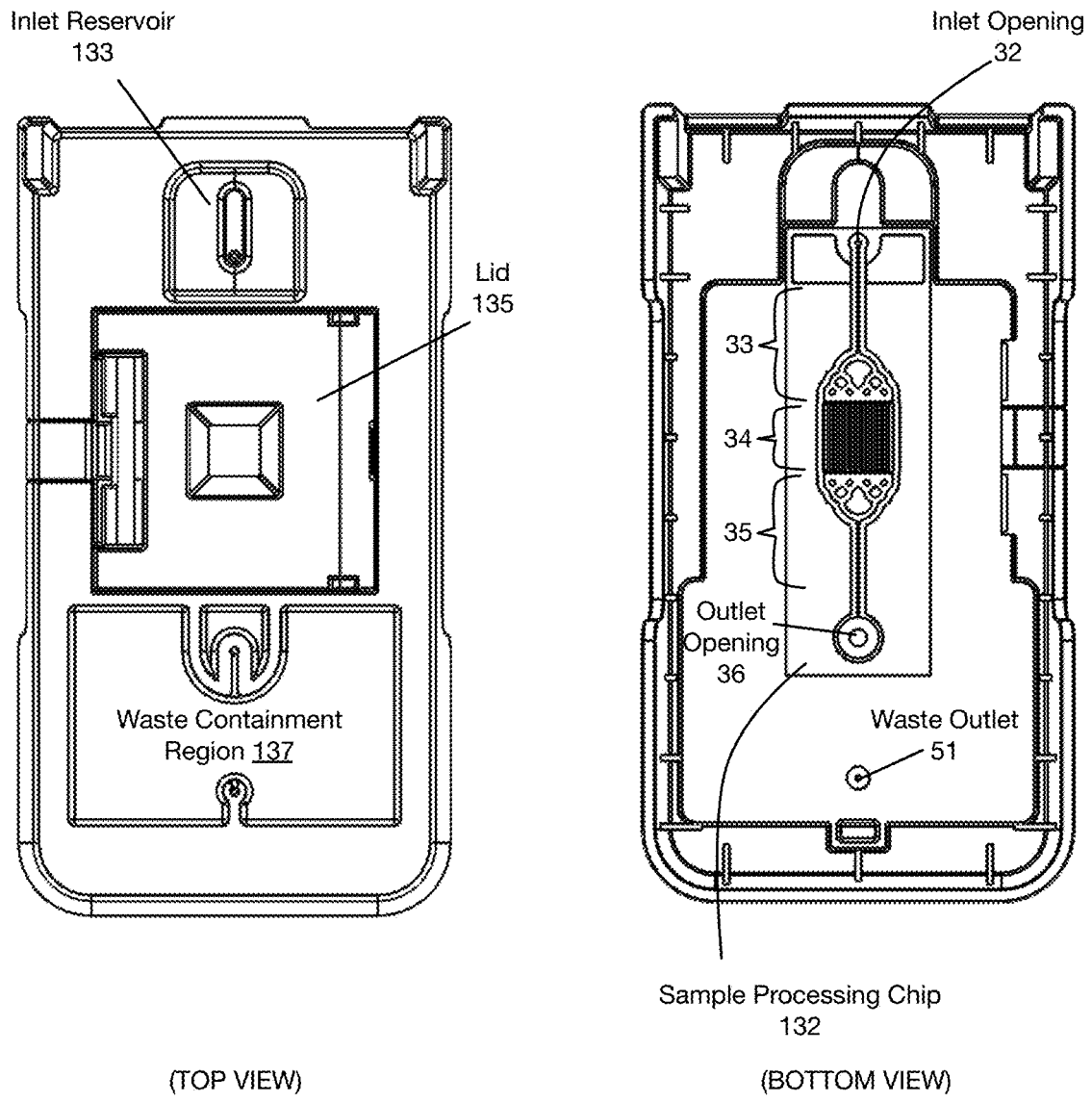

As shown in FIGS. 2A and 2C (bottom view), the sample processing chip 132, (equivalently referred to herein as a microwell device or a slide) defines a set of wells 103 (e.g. microwells) of a microwell region 34. Each of the set of wells can be configured to capture a single cell and/or one or more particles (e.g., probes, beads, etc.), any suitable reagents, multiple cells, or any other materials. In variations, microwells of the sample processing chip 132 can be configured for co-capture of a single cell with a single functional particle, in order to enable analyses of single cells and/or materials from single cells without contamination across wells. Embodiments, variations, and examples of the sample processing chip 132 are described in one or more of: U.S. application Ser. No. 16/890,417 filed 2 Jun. 2020; U.S. application Ser. No. 16/867,235, filed 5 May 2020; U.S. application Ser. No. 16/867,256, filed 5 May 2020; U.S. application Ser. No. 16/816,817, filed 12 Mar. 2020; U.S. application Ser. No. 16/564,375 filed 9 Sep. 2019; U.S. application Ser. No. 16/115,370, filed 28 Aug. 2018; U.S. application Ser. No. 16/048,104, filed 27 Jul. 2018; U.S. application Ser. No. 16/049,057, filed 30 Jul. 2018; U.S. application Ser. No. 15/720,194, filed 29 Sep. 2017; U.S. application Ser. No. 15/430,833, filed 13 Feb. 2017; U.S. application Ser. No. 15/821,329, filed 22 Nov. 2017; U.S. application Ser. No. 15/782,270, filed 12 Oct. 2017; U.S. application Ser. No. 16/049,240, filed 30 Jul. 2018; and U.S. application Ser. No. 15/815,532, filed 16 Nov. 2017, which are each incorporated in their entirety by reference above.

In material composition, the sample processing chip 132 can be composed of microfabricated silicon or glass-fused silica materials, which function to enable higher resolution of the set of wells, enabled, for instance, by defining sharper edges (e.g., thinner well walls, well walls arranged at an angle approaching 90 degrees, etc.) in the set of wells. Material composition can further enable optical interrogation of contents of the sample processing chip 132 (e.g., through a bottom surface, through a top surface), in relation to the imaging subsystem 190 described in more detail below. Materials and fabrication processes described can further enable one or more smaller characteristic dimensions (e.g., length, width, overall footprint, etc.) of the microwell cartridge as compared to conventional chip designs. In specific examples, the sample processing chip 132 is fabricated using deep reactive $10n$ etching (DRIE) techniques, according to specifications associated with one or more of: number of finished devices with acceptable level of defects (e.g., <5%); depth measured to within +/−1 micron of nominal depth (e.g., 25 microns); Rib measured to within +/−1 micron of nominal rib dimensions (e.g., 5 microns). To mitigate any issues during the fabrication, specific examples of the sample processing chip 132 were developed with: a) determination of resist thickness and lithography required for etching glass substrates with nominal depth of 30 microns with nominal widths of 5 microns between microwells; b) lateral resist erosion and determination of mask bias; c) characterization of vertical taper of microwell side-wall after etching; and d) dicing process optimization to achieve good yield of final devices.

Additionally or alternatively, the sample processing chip 132 can include any other suitable material, such as—but not limited to—a polymer, metal, biological material, or any other material or combination of materials. The sample processing chip 132 may be fabricated by various processes such as precision injection molding, precision embossing, microlithographic etching, LIGA based etching, or by other suitable techniques.

In some variations, one or more surfaces of the set of wells 103 (e.g., bottom surface, side surface, bottom and side surfaces, all surfaces, etc.) can be reacted with oligonucleotide molecules for capture of biomarkers from individual cells into individual microwells. The oligonucleotide molecules present on each and individual microwells may be barcoded to allow biomarkers processed in each microwell to be linked back to a particular well and hence a particular single cell. In one variation, the set of wells includes a set of microwells having hexagonal cross sections taken transverse to longitudinal axes of the wells, as described in one or more of the applications incorporated by reference above.

In one variation, as shown in FIG. 2C, the sample processing chip 132 can include an inlet opening 32, a first fluid distribution network 33 downstream of the inlet opening, for distribution of fluids to a set of microwells 34 (e.g., 1,000 to 10,000,000 wells), a second fluid distribution network 35 downstream of the set of microwells 34, and an outlet opening 36 coupled to a terminal portion of the second fluid distribution network 35, for transfer of waste fluids from the sample processing chip 132. In this variation, the sample processing chip 132 is coupled to a first side (e.g., under-side) of the base substrate 131 (e.g., by laser welding, glue bonding, solvent bonding, ultrasonic welding or another technique). Coupling of the sample processing chip 132 to the side of the base substrate 131 can enable transfer of heat from the heating and cooling subsystem 150 to the set of microwells 34 and/or other regions of the sample processing chip 132, where the heating and cooling subsystem 150 is described in more detail below.

The base substrate 131, as described above, can also include an inlet reservoir 133 (e.g., defined at a second side of the base substrate 131 opposing the first side to which the sample processing chip 132 is coupled). The inlet reservoir functions to receive sample material (e.g., samples containing cells, sample containing barcoded cells, sample containing encapsulated materials, samples containing particles, etc.) and/or sample processing materials from the process container 20' described above, for delivery into the inlet opening 32 of the sample processing chip 132. In variations, the inlet reservoir 133 can be defined as a recessed region within a surface of the base substrate 131, wherein the recessed region includes an aperture that aligns with and/or seals with the inlet opening 32 of the sample processing chip 132. The inlet reservoir 133 of the base substrate 131 can interface with upstream fluid containing components and/or bubble mitigating components, as described in applications incorporated in their entirety by reference above.

In variations, one or more of the inlet reservoir 133 of the base substrate 131 and the inlet 32 of the sample processing chip 132 can include valve components that can be open or closed by one or more components of the system 100. In a first variation, the inlet reservoir 132 includes an aperture that can be accessed by a pipette tip or any other suitable attachment of a fluid handling subsystem coupled to the gantry 170 (described in more detail below). In some embodiments, the aperture can be closed and therefore prevent fluid from traveling from the inlet reservoir 132 to the sample processing chip 132. The inlet reservoir 132 can, however, be configured in another suitable manner. The opening associated with the inlet reservoir 133 may have a conical shape surface open towards the top allowing interfacing and sealing a pipette tip such that fluid (aqueous solutions or oil or air) may be pumped directly into the microchannel defined in 33 in FIG. 2C.

As shown in FIGS. 2A and 2B, the base substrate 131 can also define an access region 134 for accessing one or more regions of the sample processing chip 132, where the access region can allow regions of the sample processing chip 132 to be observed and/or extracted from the sample processing chip 132 at various phases of sample processing. As shown in FIGS. 2A and 2B, the access region 134 can be defined as a recessed region within the base substrate 131, and include an opening 37 aligned with the region of the sample processing chip 132 that includes the set of microwells. The sample processing chip 132 may have as few as 100 microwells to as many as 100 million microwells. As such, in variations wherein the microwell region is open to the environment (e.g., without a covering to seal the wells), the opening 37 of the access region 134 can function as a microwell to provide access to contents of the microwells for observation and/or material extraction (e.g., by magnetic separation, as described in further detail below). The opening 37 can match a morphology and footprint of the microwell region, and in a first variation, as shown in FIG. 2B, can be a square opening. However, in other variations, the opening 37 can have another suitable morphology.

As shown in FIGS. 2A-2C, the base substrate 131 can include or otherwise couple to a lid 135 covering the access region 134, where the lid 135 can include a gasket 136 providing sealing functions, and where the lid 135 functions to transition the access region 134 between open and closed modes, thereby preventing evaporative sample loss and/or contamination of contents of the sample processing chip 132 during operation. The lid 135 can additionally or alternatively function to protect the contents of the microwells or other processing regions of the sample processing chip 132 from debris, enable a processing of the contents of the sample processing chip 132 (e.g. by isolating regions from the ambient environment), initiate the start of a protocol (e.g., by opening to accept reagents from a pipettor), prevent user manipulation of the sample processing chip 132 (e.g., by closing after all necessary reagents have been added), define (e.g., with the lid 135) part or all of a fluid pathway, cavity, or reservoir (e.g. serve as the top surface of a fluidic pathway between the inlet and the set of microwells, serve as a boundary of a fluid pathway adjacent the microwell region, serve as the top surface of a fluidic pathway between the set of wells and the waste chamber, etc.), or perform any other suitable function.

As shown in FIG. 2B, in at least one variation, the lid 135 can be complementary in morphology to features of the access region 134, such that the lid 135 mates with the access region 134, while providing a gap with the sample processing chip 132. Additionally, in variations (shown in FIGS. 3B and 3C), the lid 135 can be substantially flush with the base substrate 131 at a top surface when the lid 135 is in the closed position. However, the lid 135 can be morphologically configured in another suitable manner.

In variations, a protrusion 38 of the lid 135 can interface with the opening 37 of the access region 134, thereby substantially preventing access to the opening 37 when the lid is in the closed position. As shown in FIG. 2B, in some variations, the protrusion 38 can have a base (or other region) surrounded by a gasket 136, which functions to seal the opening 37 of the access region 134 in the closed position of the lid 135. Variations of the lid 135 can, however, omit a gasket and promote sealing of the access region 134 in another suitable manner. In another embodiment, the entire bottom surface of the lid that comes closest to the microwells in the sample processing chip 132 can be an elastomeric substrate (e.g., flat elastomeric substrate) allowing the elastomeric lid to cover the microwells, thereby preventing any evaporative or diffusive loss of molecules during thermocycling in each of the microwells.

In some variations, the lid 135 can include a locking or latching mechanism that allows the lid 135 to be maintained in the closed position with the base substrate 131 until the locking/latching mechanism is released. In the variation shown in FIGS. 3A-3C, a peripheral portion of the lid 135 can include a one or more tabs 39 that interface with corresponding tab receiving portions of the base substrate 131, where, the tabs 39 are configured to flex when pushed into the base substrate 131 until they interface with the tab receiving portions of the base substrate 131 and return from a flexed configuration to a latched state. Additionally or alternatively, in the variation shown in FIGS. 3A-3C, the locking/latching mechanism can include a releasing body 41 (e.g., bar, recess, hook, etc.) that can be interfaced with in order to release the tab(s) 39 from the tab receiving portions, and transition the lid 135 from the closed mode to the open mode in relation to the base substrate 131. As such, the lid 135 provides the lid an open mode in which the access region 134 is uncovered and a closed mode in which the access region 134 is covered. In the variation shown in FIGS. 3A-3C, the releasing element 41 includes a bar that is recessed away from the access region 134 of the base substrate 131, where the bar can be reversibly coupled to a lid-opening tool 145. In variations, the lid-opening tool 145 can include a first region (e.g., first end) that interfaces with a an actuator (e.g., actuating tip, pipettor of a fluid handling subsystem coupled to the gantry 170 described below, etc.), and a second region (e.g., second end) including a linking element 42 configured to interface with the releasing element 41 of the lid 135. Then, with movement of the pipettor/pipette interface, the lid-opening tool 145 can be configured to pull on the releasing element 41 and/or push on the lid 135 in order to transition the lid between open and/or closed modes. As such, in relation to fluid handling elements coupled to the gantry 170 described below, the system 100 can provide operation modes for: coupling a lid-opening tool 145 to an actuator (e.g., coupled to a gantry 170), the lid-opening tool including a linking element 42; moving the lid-opening tool into alignment with a releasing element 41 of the lid 135, reversibly coupling the linking element 42 with the releasing element 41; and applying a force to the releasing element 41, thereby releasing the lid 135 from a latched state and transitioning the lid 135 from a closed mode to an open mode. In order to effectively apply an unlatching force (e.g., by the actuator (e.g., coupled to a gantry 170), the base substrate 131 can be retained in position (e.g., by retention elements described in Section 2.1.4, by retention elements of the heating and cooling subsystems, by retention elements of the fluid level detection subsystem, by retention elements of the deck, etc.) which passively or actively apply counteracting forces against the unlatching forces applied through the lid-opening tool 145.

In variations, however, the locking/latching mechanism can additionally or alternatively include or operate by way of: a lock-and-key mechanism, magnetic elements, or another suitable mechanism. Furthermore, in alternative variations, the lid 135 can include another lid actuator, for instance, including a motor that rotates the lid about an access parallel to a broad surface of the sample processing cartridge 130. The actuator can additionally or alternatively be configured to translate the lid 135 (e.g. slide the lid 135 parallel to a broad surface of the sample processing cartridge 130, translate the lid 135 perpendicular to the broad surface, etc.) or otherwise move the lid 135 to selectively cover and uncover one or more predetermined regions (e.g. the set of microwells). As such, the lid 135 can be configured to operate in an automated or semi-automated fashion, such that the lid 135 automatically closes upon one or more triggers (e.g., cell capture protocol is initiated by a user, cell processing protocol is initiated by a user, all reagents for a selected protocol have been added from the process container 20, etc.) and opens upon one or more triggers (e.g., cell capture protocol has been completed, upon user request, it has been determined that the cells are viable, it has been determined that single cells have been captured, etc.). Additionally or alternatively, operation of the lid 135 can be initiated and/or completed by a user, operated according to a schedule or other temporal pattern, or otherwise operated.

As shown in FIGS. 2A-2C, the base substrate 131 can also include a waste containment region 137 for receiving waste material from the sample processing chip 132. The waste containment region 137 can also function to maintain desired pressures (e.g., vacuum pressures, etc.) within the sample processing chip 132, thereby enabling flow of liquid from the inlet reservoir 133 through the sample processing chip 132 and to the waste containment region 137. The waste containment region 137 can be defined as a volume (e.g., recessed into the base substrate 131, extending from the base substrate 132, coupled to an outlet of the base substrate 131, etc.) for receiving waste or other materials from the sample processing chip 132. In the variation shown in FIGS. 2A-2C, the waste containment region 137 is defined at a side of the base substrate 131 opposing the side to which the sample processing chip 132 is coupled, such that waste from the sample processing chip 132 is pushed or pulled upward into the waste containment region 137 by forces of the pumping subsystem 157 described in more detail below. However, the waste containment region 137 can additionally or alternatively be configured in another suitable position relative to the base substrate 131 and the sample processing chip 132, in order to receive waste. The waste containment region 137 can have a volumetric capacity of 10-100 mL or another suitable volumetric capacity.

As shown in FIGS. 2A-2C, the waste containment region 137 can include a cover 48 (e.g., a cover that is approximately co-planar with the lid 135), which facilitates containment of waste within the waste containment region 137. Alternatively, the waste containment region 137 may not include a cover. Furthermore, as shown in FIG. 2C, examples of the waste containment region 137 can include a pump outlet 51 distinct from the cover, where the pump outlet 51 can allow the residual air in the waste chamber to be pressurized by an off-cartridge pump (e.g., by pumping mechanisms, etc.); however, variations of the waste containment region 137 can alternatively omit a waste outlet.

In relation to the waste containment region 137, the system 100 can further include a valve 43 configured to allow and/or prevent flow from the sample processing chip 132 to the waste containment region 137. The valve 43 can interface with the outlet opening 36 of the sample processing chip 132 described above, in order to enable and/or block flow out of the outlet opening 36 and into the waste containment region 137. The valve 43 can have a normally open state and transition to a closed state upon interacting with a valve-actuating mechanism. Alternatively, the valve 43 can have a normally closed state and transition to an open state upon interacting with a valve-actuating mechanism.

Figure 4A:
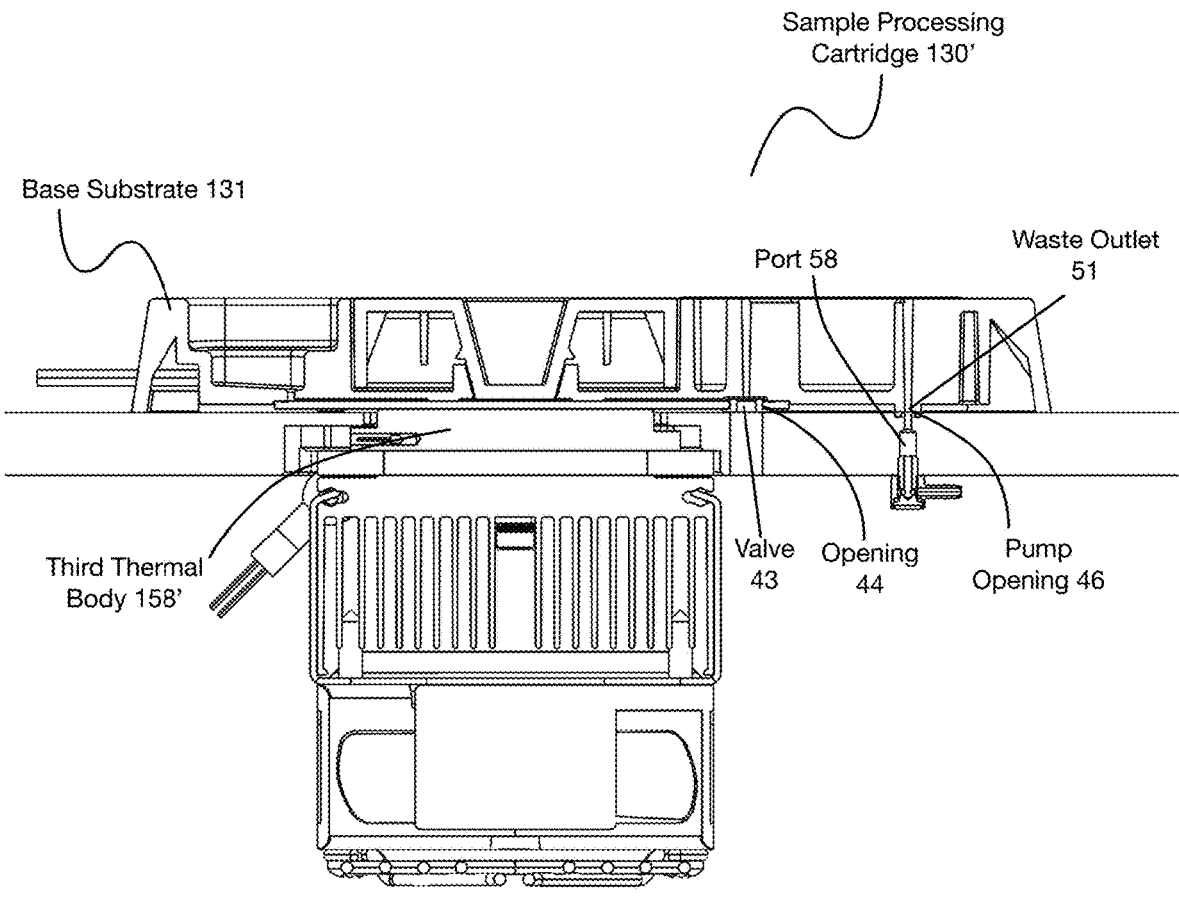
FIGS. 4A-4B depict operation modes of a valve subsystem associated with the sample processing cartridge shown in FIGS. 2A-2C
Figure 4B:
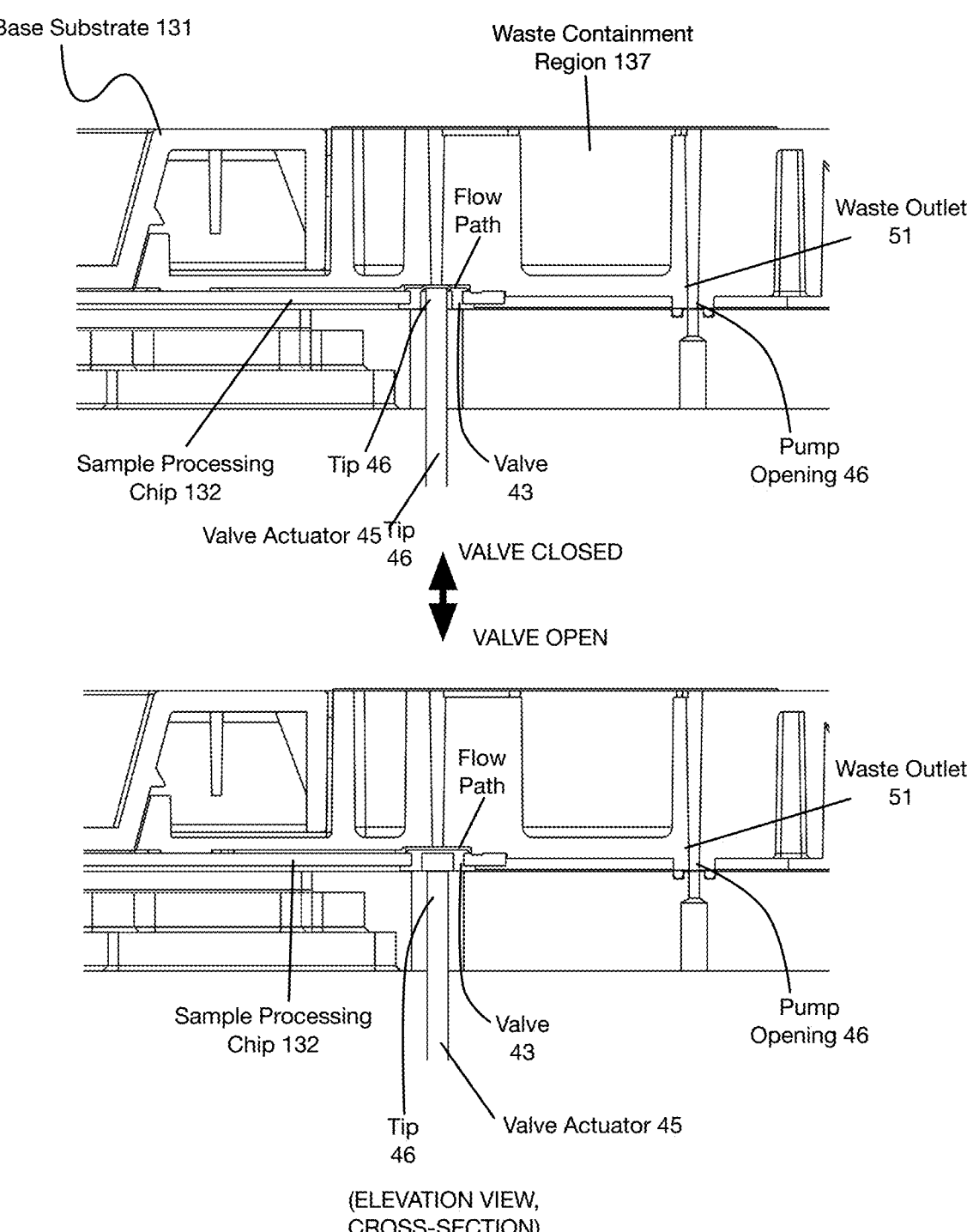

In the variation shown in FIGS. 2A and 4A-4B, the valve 43 can include an elastomeric body and is configured to couple the sample processing chip 132 to the base substrate 131 through an opening 44 of the sample processing chip 132 that aligns with a corresponding valve-receiving portion of the base substrate 131. In this variation, a transitionable portion of the valve 43 is configured to be positioned along a flow path from the outlet opening 36 of the sample processing chip 132 to the inlet of the waste containment region 137 of the base substrate 132 (e.g., along a flow path from the microwell region to an outlet of the sample processing chip into a waste containment region of the sample processing cartridge). In an example the opening 44 of the sample processing chip 132 is contiguous with the outlet opening 37 of the sample processing chip 132; however, in other variations, the outlet opening 37 and the opening 44 may be displaced from the each other and connected by another microfluidic channel. As such, closure of the valve 43 can block flow from the outlet opening 37 into the waste containment region 137, and the valve 43 can be opened to allow flow from the outlet opening 37 into the waste containment region 137.

In a variation shown in the cross sectional images of the base substrate 131 shown in FIGS. 4A-4B, a valve actuator 45 can access the base substrate 131 from below (e.g., from below the deck), and pass through a channel or other recess/opening of the base substrate 132 in order to interact with the valve 43. In particular, when a tip 46 (aligned with the opening into the base substrate) of the valve actuator 45 pushes against the valve (e.g., a elastomeric membrane of the valve 43), as shown in FIG. 4B (top), the valve 43 can transition to a closed state in order to fluidically decouple the outlet opening 37 of the sample processing chip 132 from the waste containment region 137. Additionally or alternatively, as shown in FIG. 4B (bottom), removal of force by the valve actuator 45 can remove pressure from the valve 43 and transition it to an open state to fluidically couple the outlet opening 36 of the sample processing chip 132 from the waste containment region 137. As such, the valve actuation subsystem includes an engaged mode wherein the tip extends into the valve opening to deform the elastomeric valve, thereby closing the flow path, and a disengaged mode wherein the tip is retracted, thereby opening the flow path. However, the valve 43 can additionally or alternatively be configured in another suitable manner.

In other variations, the system can include a similar mechanism for coupling a valve to other flow paths of the sample processing chip 132 and/or to the base substrate 131.

Variations of the base substrate 131 can, however, include other elements. For instance, as described in more detail below, the base substrate 131 can include one or more openings, recesses, and/or protrusions that provide further coupling with the sample processing chip 132, in order to promote or inhibit flow through the sample processing chip 132. For instance, as shown in FIG. 4A, the base substrate 131 can include a pump opening 46 that couples the base substrate 131 to a pumping element of the pumping subsystem 157 (e.g., through deck no), in order to drive and/or stop fluid flow through the sample processing chip 132. The base substrate 131 of the sample processing cartridge 130 can, however, include other suitable elements.

Embodiments, variations, and examples of the chip 101 can include embodiments, variations, and examples of the capture devices described in one or more applications incorporated by reference above.

2.2. System—Containers for Processing Retrieved Materials

In relation to processing (e.g., purification, washing, extraction, amplification, etc.) of retrieved material using the separation systems described, the system 100 can also include a process container 20. The process container 20 functions to process retrieved target components of samples according to one or more workflows for various applications, as described in further detail below. As such, material can be retrieved from the sample processing chip 132 described above and transferred to the process container 20 for further processing, as described in more detail below. Additionally or alternatively, in some variations, the process container 20 can contain, in one or more compartments, materials for cell capture and sample processing, in the context of a fully automated system. As such, the process container 20 can define a set of storage volumes distributed across a set of domains, where the set of domains can be configured for providing suitable environments for the material contents of each domain. The set of storage volumes can directly contain sample processing materials, and/or can alternatively be configured to receive and maintain positions of individual containers (e.g., tubes, etc.) that contain sample processing materials. The storage volumes of each domain can be distributed in arrays, or otherwise arranged.

Individual storage volumes of the set of storage volumes of the process container 20 can further include one or more seals, which function to isolate materials within the process container 20, to prevent cross-contamination between materials within individual storage volumes, to prevent contaminants from entering individual storage volumes, and/or to prevent evaporative loss during storage and shipment. The seal(s) can be puncturable seal(s) (e.g., composed of paper, composed of a metal foil, and/or composed of any other suitable material). However, the seal(s) can alternatively be configured to be non-puncturable (e.g., the seal(s) can be configured to peel away from the process container 20). In embodiments, certain reagent containers may also be sealed by a hinged lid that can be opened or closed by a tool (e.g., as described in more detail below), as needed for processing at appropriate steps of the protocol.

In variations, the set of domains can include a first domain for storing reagents requiring a chilled environment (e.g., at a temperature from 1 C-15 C), a second domain for storing materials that can be stored in ambient conditions, a third domain storing tubes with materials for performing polymerase chain reaction (PCR) operations and interfacing with heating elements described below, a fourth domain for storing functionalized particles (e.g., beads with probes having barcoding regions and other functional regions, as described in U.S. application Ser. No. 16/115,370, etc.), and a fifth domain for performing separation operations (e.g., separation of target from non-target material by magnetic force). In variations, domains providing different environments for the storage volumes can be configured differently. For instance, the first domain (i.e., for cold storage) can be composed of a thermally insulating material and/or can include insulating material about storage volumes of the domain (e.g., individually, about the entire domain). Additionally or alternatively, a domain for separation can be include magnetically conductive materials configured to provide proper magnetic field characteristics for separation. Additionally or alternatively, domains for thermocycling or other heat transfer applications can be configured with thermally conductive materials to promote efficient heat transfer to and from the process container 20. In embodiments, various domains can be optimally positioned such that there is minimal cross-talk between certain operations. For example, the domain(s) for chilled reagent storage volumes can be maintained a temperature (e.g., 4 C) during a run, whereas the domain(s) for PCR reactions can require heating (e.g., up to 95 C during denature). As such, to minimize the effect of PCR thermocycling on chilled reagents, the domain(s) containing the reagents stored at ambient temperature may be configured in between the PCR thermocycling domain(s) and chilled domain(s). In order to further prevent heat cross-talk, additional buffer tubes with just air may be used in between critical domains that need independent temperature control.

In variations, process materials supported by the domains of the process container 20 can include one or more of: buffers (e.g. ethanol, priming buffer, lysis buffer, custom lysis buffers, sample wash buffers, saline with RNAase inhibitors, bead wash buffers, RT buffer, buffer, etc.), oils (e.g. perfluorinert oil), PCR master mixtures, cells, beads (e.g. functionalized beads) or any other suitable materials used for cell capture and/or sample processing. Additionally or alternatively, one or more of the set of storage volumes can be empty (e.g. initially empty, empty throughout one or more processes, empty prior to filling by an operator, etc.). Different storage regions in various domains of the process container 20 can have initial reagent volumes from a few microliters (e.g., 5 microliters) to 50 milliliters.

Figure 5:
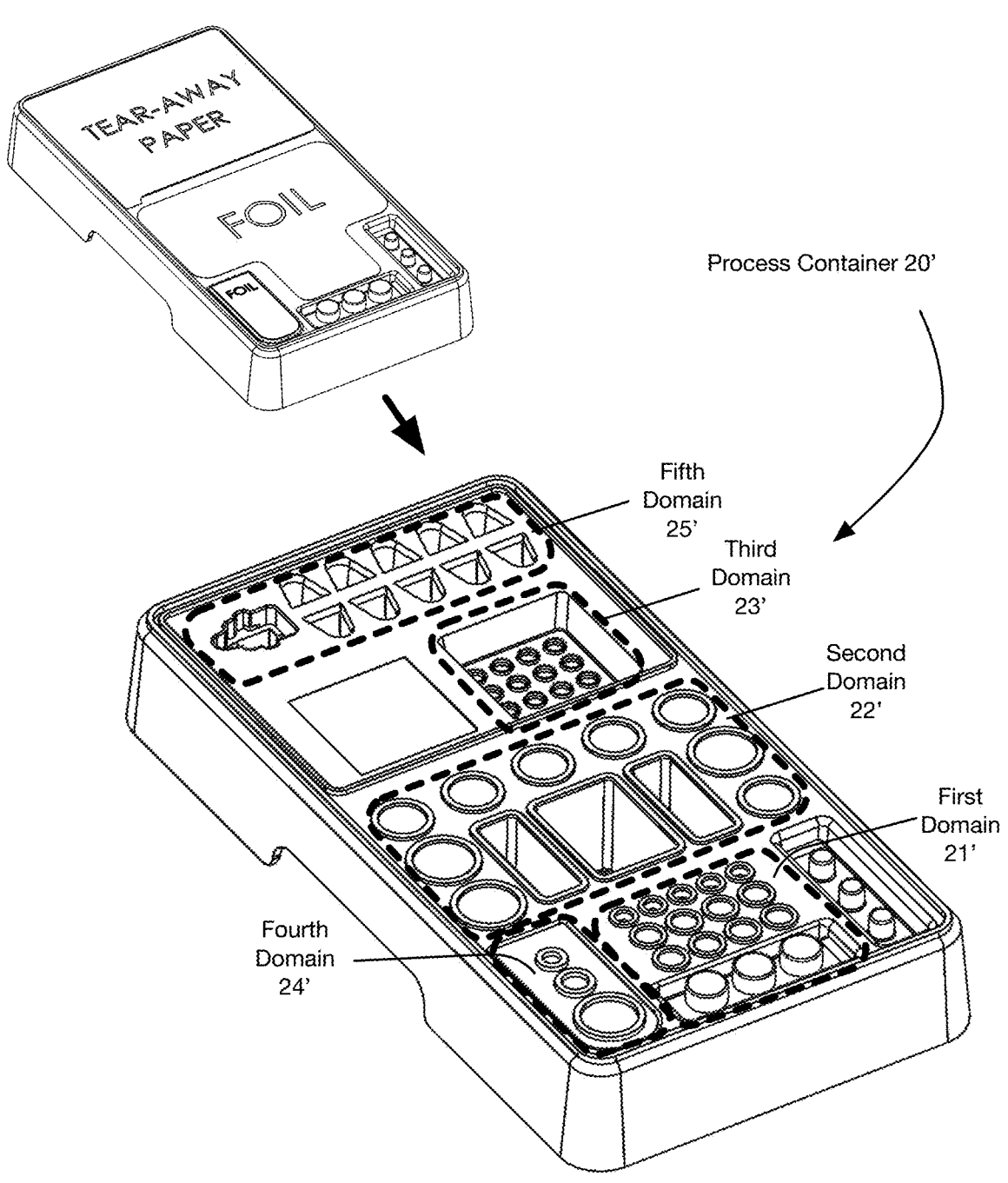
FIG. 5 depicts a variation of a process container for target material processing, retrieval, and downstream processing.

In a specific example, as shown in FIG. 5, the process container 20' includes a first domain 21' at a first peripheral region of the process container 20' for storing reagents requiring a chilled environment, a second domain 22' at a central region of the process container 20' for storing materials that can be stored in ambient conditions, a third domain 23' at a peripheral region of the process container 20', near the second domain 122, for storing tubes with materials for performing polymerase chain reaction (PCR) operations, a fourth domain 24' at a peripheral region of the process container 20', for storing functionalized particles (e.g., beads with probes having barcoding regions and other functional regions, as described in U.S. application Ser. No. 16/115, 370, etc.), and a fifth domain 25' at a peripheral region of the process container 20' for performing separation operations (e.g., separation of target from non-target material by magnetic force). In the specific example, the fourth domain 24' can be a modular element, whereby the fourth domain 24' can be stored separately from the rest of the process container 20' until the functionalized particles are ready for use, at which point the fourth domain 24' is set in position and coupled with the process container 20'.

In the specific example, the first domain 21' and the second domain 22' are covered by a first seal composed of a metal foil, the third domain 23' and the fifth domain 25' are covered by a second seal composed of a paper, and the fourth domain 24' is covered by a third seal composed of a metal foil. However, variations of the example of the process container 20' can be configured in another suitable manner.

Furthermore, variations of the process container 20, 20' can omit various domains, and be configured for processing and separation of retrieved target materials, as described in more detail below.

The process container 20 can further additionally or alternatively include aspects described in applications incorporated by reference above.

2.3 System—Deck, Separation Subsystem, and Gantry Aspects

In variations, aspects of the sample processing cartridge 130 and process container 20 can be supported by or otherwise interact with other system elements (e.g., of a system for automating sample processing). As shown in FIGS. 6A-6B and 7A-7C, in embodiments, the system 100 can include a deck 10, which functions as a platform to support and position one or more components of the system 100 (e.g., at a top broad surface, at a top and bottom broad surface, at a side surface, etc.) for automated sample processing. Furthermore, the deck 10 can function to position one or more components of the system 100 to align with or otherwise interact with fluid processing subsystems, imaging subsystems, heating subsystems, separation subsystems (e.g., magnetic separation subsystems), and/or other subsystems coupled to the gantry 170 and/or base 180, as described below. In this regard, the deck 10 can be stationary as a reference platform, while other components are actuated into position for interacting with elements of the deck 10. Alternatively, the deck 10 can be coupled to one or more actuators for positioning elements of the deck 10 for interactions with other subsystems.

Figure 6A:
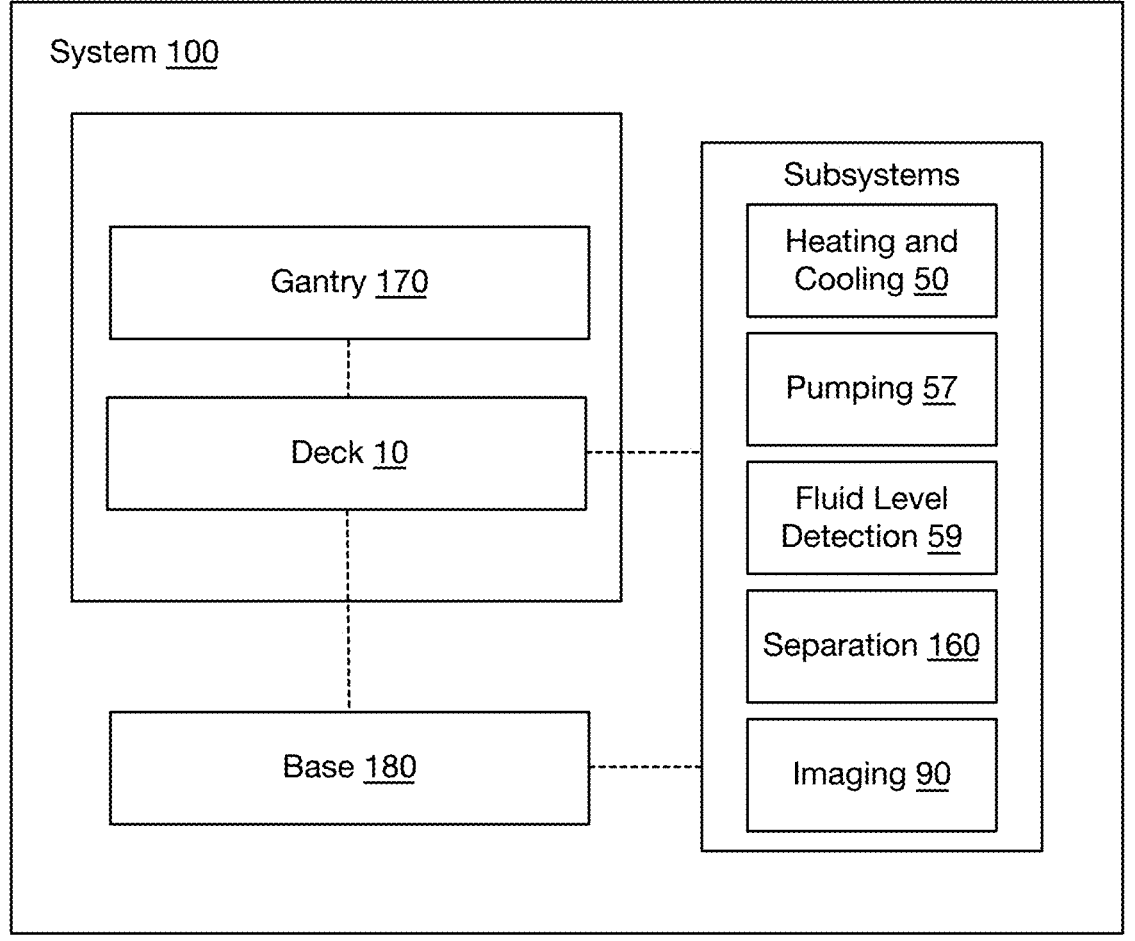
FIGS. 6A-6B depict schematic representations of an embodiment of a system for automated single cell sample processing.
Figure 6B:
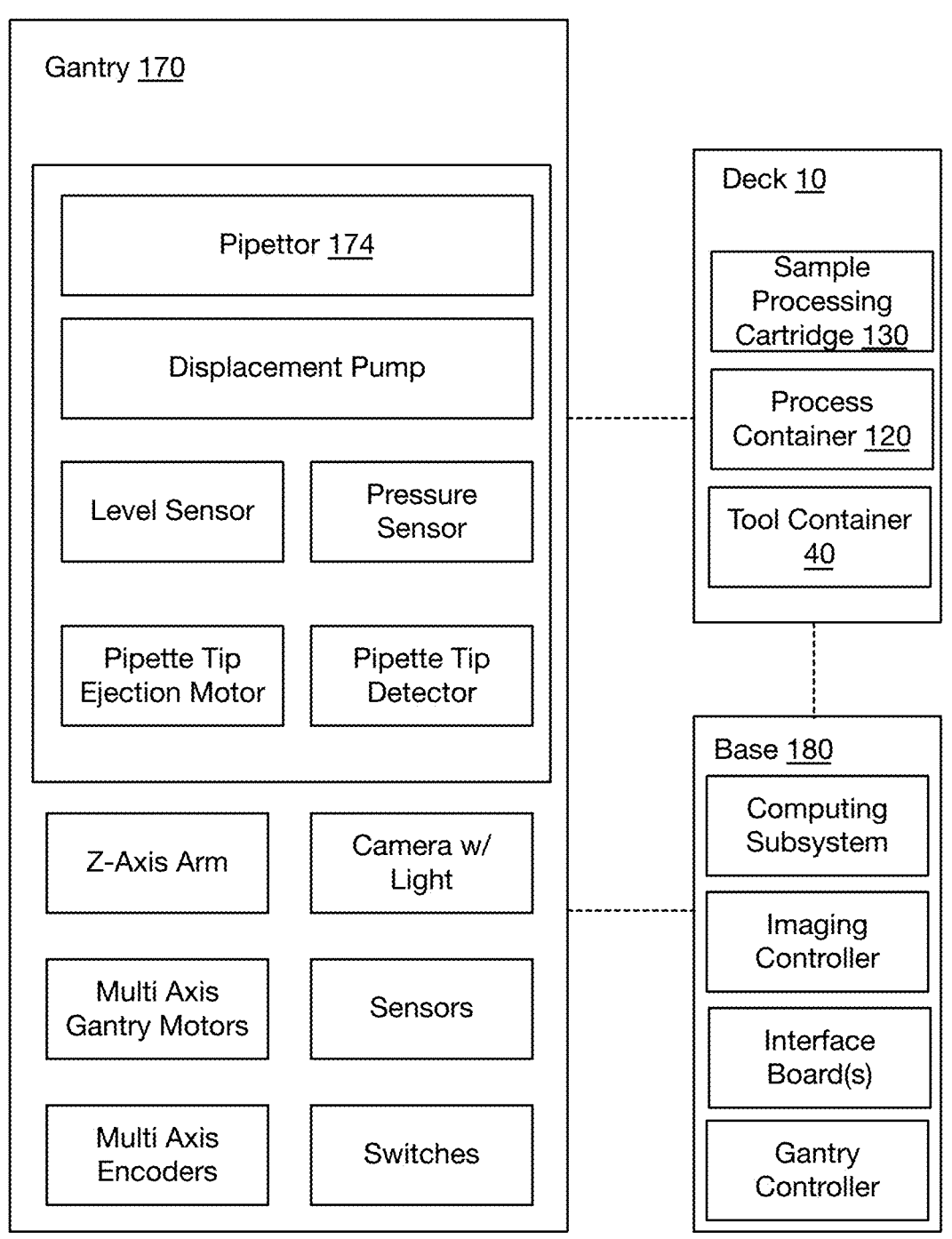

In the embodiment shown in FIGS. 6A-6B, the deck no provides a platform supporting one or more units of the sample processing cartridge 130, the process container 20, a tool container 40 (described in applications incorporated by reference), a heating and cooling subsystem 50, a pumping subsystem 57, a fluid level detection subsystem 59, a separation subsystem 160, and an imaging subsystem 90. The sample processing elements can be supported in a co-planar manner by the deck 10, or alternatively at different planes. Preferably, discrete elements supported by the deck are non-overlapping, but alternative embodiments of the deck no can support the sample processing elements in an overlapping manner (e.g., for conservation of space, etc., for operational efficiency, etc.).

Figure 7A:
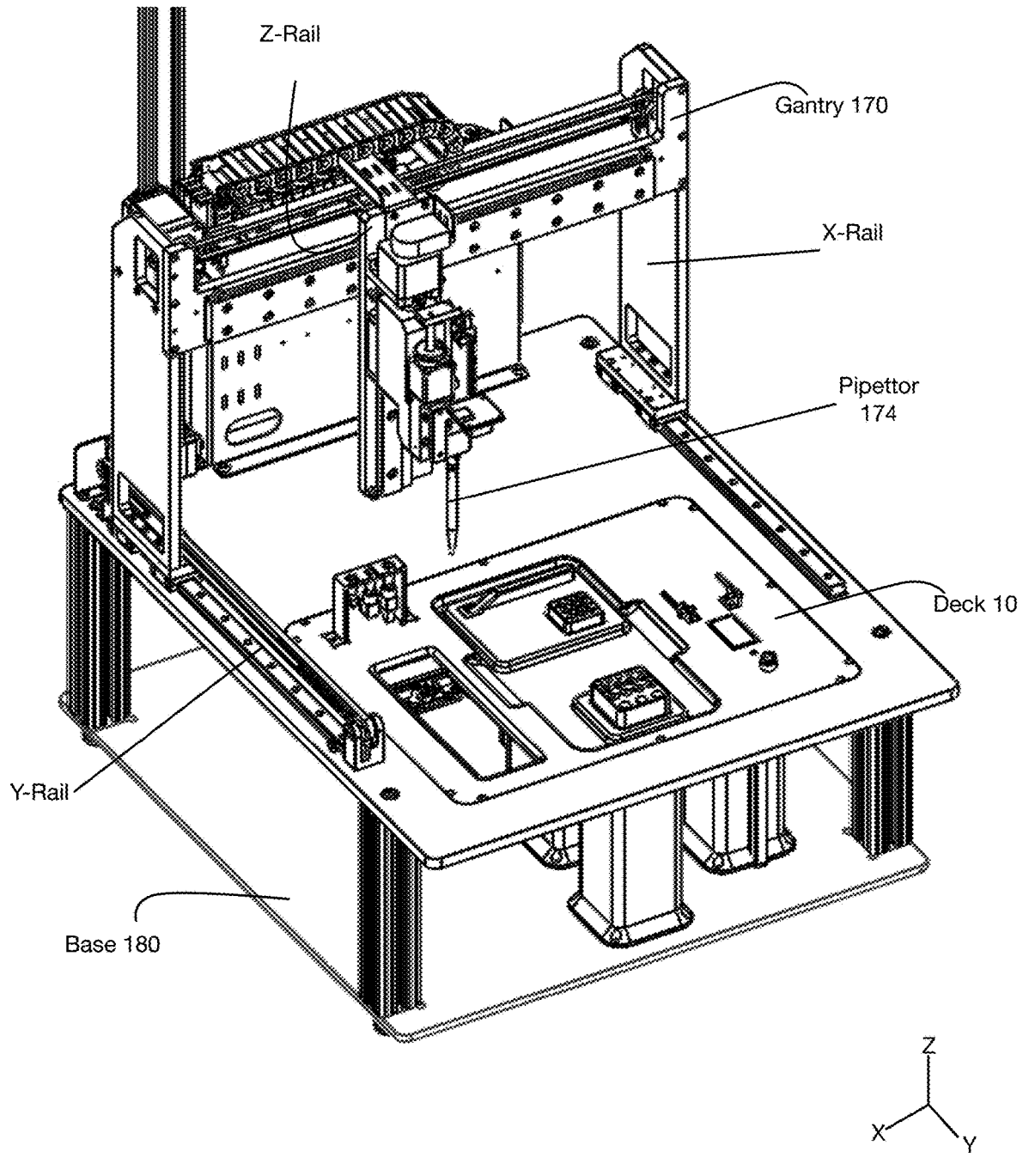
FIGS. 7A-7C depict views of a variation of the system shown in FIGS. 6A-6B.
Figure 7B:
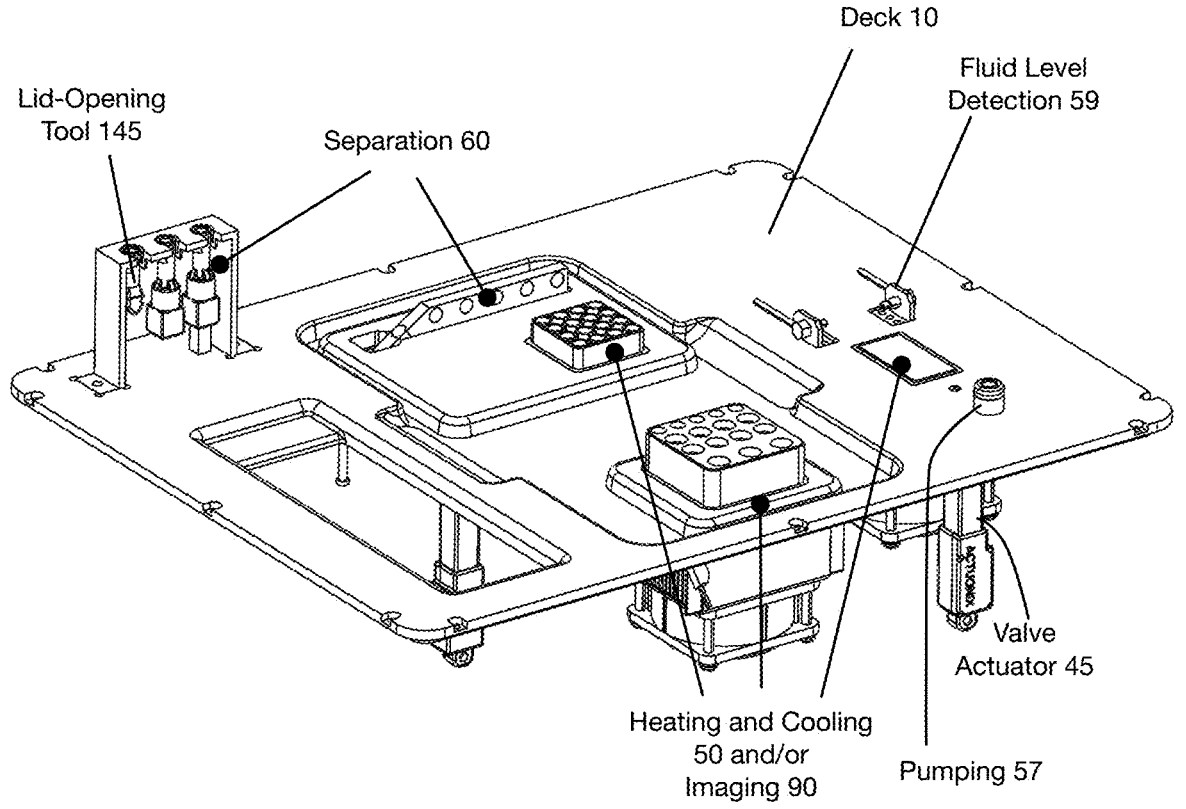
Figure 7C:
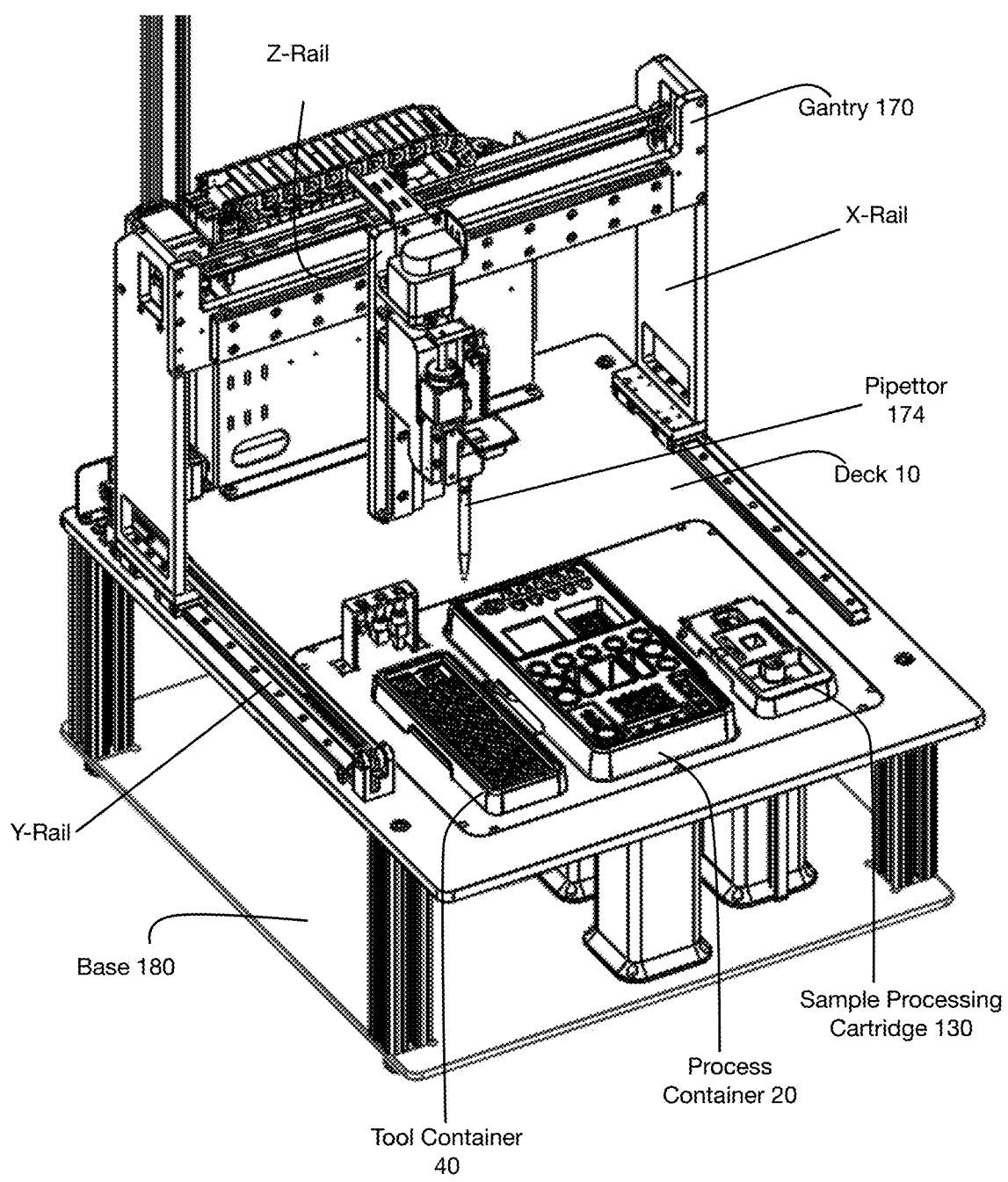

As such, and as shown in FIGS. 7A-7C, the deck 10 also includes at least one region for supporting a unit of the sample processing cartridge 130, where the region functions to position the sample processing cartridge 130 relative to portions of the heating and cooling subsystem 50, the pumping subsystem 57, the fluid level detection subsystem 59, and/or the imaging subsystem 90. In this regard, the region can include one or more openings, recesses, and/or protrusions for providing interfaces between complementary portions of the sample processing cartridge 130 and associated portions of the heating and cooling subsystem 50, the pumping subsystem 57, the fluid level detection subsystem 59, and the imaging subsystem 90, and additionally to promote and maintain alignment between such portions.

Similarly, as shown in FIGS. 7A-7C, the deck 10 can include at least one region for supporting a unit of the process container 20, where the region functions to position the process container 20 relative to portions of the heating and cooling subsystem 50, and separation subsystem 160 described in more detail below. In this regard, the region can include one or more openings, recesses, and/or protrusions for providing interfaces between complementary portions of the process container and associated portions of the heating and cooling subsystem 50 and separation subsystem 60, and additionally to promote and maintain alignment between such portions.

As shown in FIGS. 7A and 7B, the deck 10 can also include at least one region for supporting a unit of a tool container 40, where the region functions to position the tool container 40 relative to fluid handling apparatus of the gantry 170 described below. Embodiments, variations, and examples of the tool container 40 are described in applications incorporated by reference above.

Embodiments, variations, and examples of the heating and cooling subsystem 50, pumping subsystem 57, fluid level detection subsystem 59, and imaging subsystem 90, and coupling with regard to gantry 170 (with pipettor 174)

and base 180 are also described in more detail in applications incorporated by reference. Aspects of the separation subsystem 160 are further described below.

2.4 System—First Variation for Retrieval by Magnetic Force

Figure 8A:
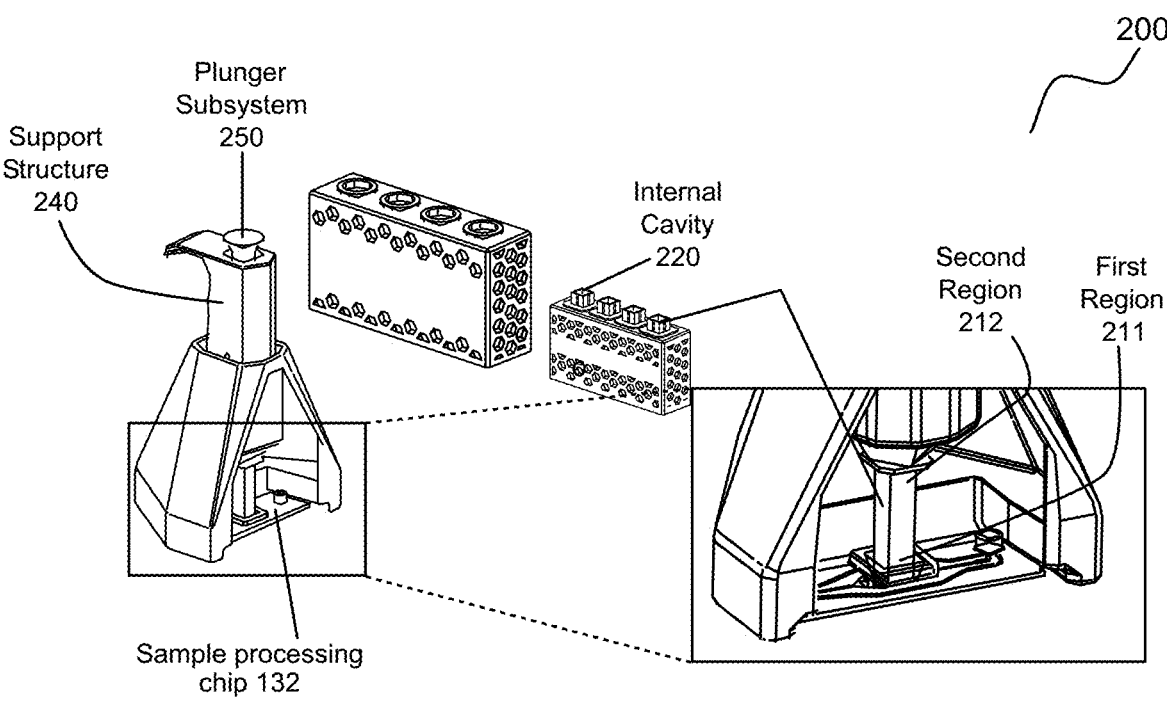
FIGS. 8A-8C depict a first magnetic variation of a system for target material retrieval.
Figure 8B:
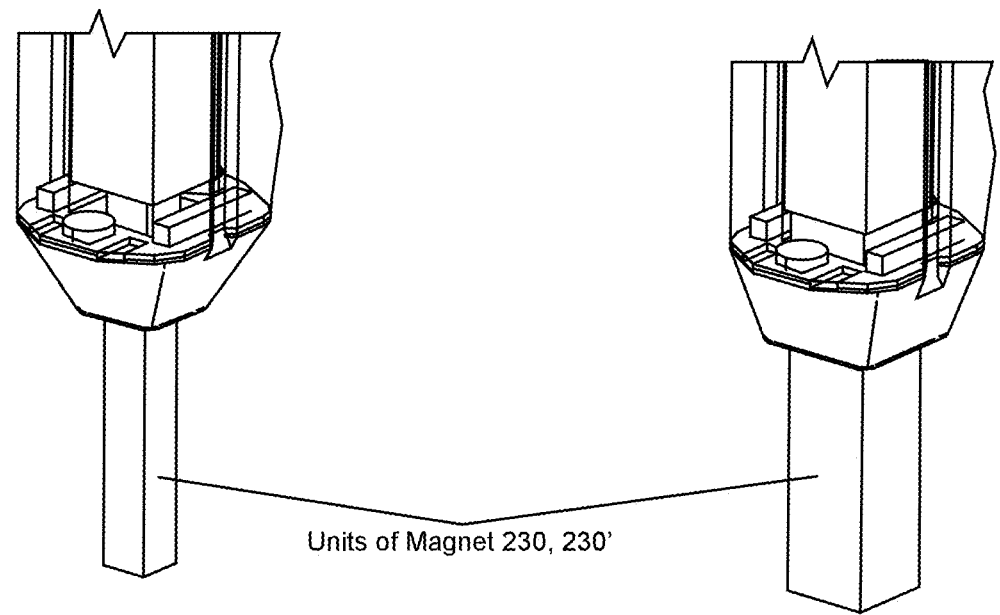
Figure 8C:
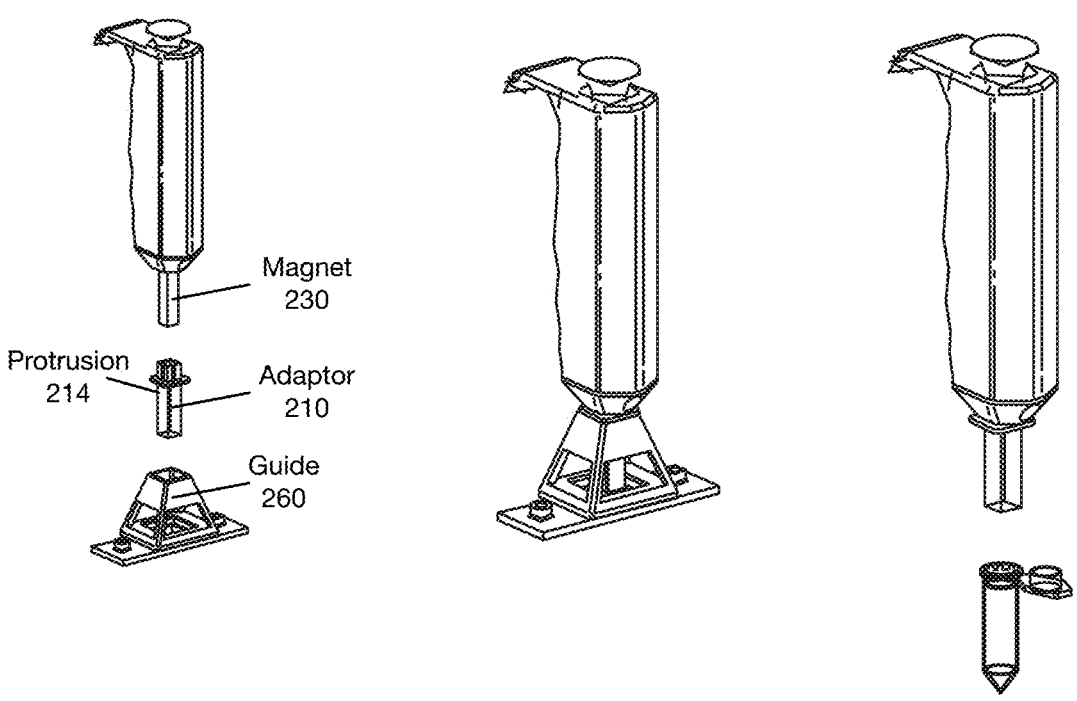

As shown in FIGS. 8A-8C, a variation of the system 200 includes an adaptor 210 (e.g., of separation subsystem 160 described above) including a first region 211 configured to couple to a capture region of a sample processing cartridge (e.g., embodiment of sample processing cartridge 130 described above), for capturing particles in single-particle format, a second region 212, and an internal cavity 220 passing from the first region to the second region; a magnet 230 configured to pass into the internal cavity 220 of the adaptor 210 and apply an attracting force to the capture region of the sample processing cartridge 130 during operation; and a support structure 240 reversibly coupled to the second region 212 of the adaptor 210 and to the magnet 230.

The support structure 240 of the system 200 can also include a plunger subsystem 250 coupled to an ejector proximal the magnet 230, wherein in a baseline operation mode the adaptor 210 is coupled to the support structure 240 and the plunger subsystem 250 is not activated, and in an ejecting mode, the adaptor 210 is released from the support structure 240 in response to activation of the plunger subsystem 250. In variations, the plunger subsystem 250 can also include structures that function to facilitate fluid dispensing and aspiration functions in order to dispense and/or retrieve material from the capture region of the sample processing cartridge 130. Furthermore, the system 200 can include a guide 260 configured to retain the support structure 240 in position relative to the capture region of the sample processing cartridge 130 and to prevent physical contact between the magnet 230 and the capture region of the sample processing cartridge 130 during operation.

The system 200 functions to controllably apply a magnetic force to the capture region of the chip 201, in order to provide an attractive force for drawing target material coupled (directly or indirectly) to magnetic components within the capture region, into the adaptor 210. Embodiments of methods implemented with the system 200 can produce retrieval of target material in 5-8 minutes of manual operation time (and 10-45 minutes total time), with a retrieval efficiency of >90% where only magnetic particles coupled to target material of the sample are retrieved. The system 200 can thus function to produce increased selective retrieval efficiency can thus reduce downstream costs in relation to processing reagent and other material costs (due to reduced volumes needed, due to reduced splits in biochemistry reactions) and processing burden. The system 200 can implement one or more embodiments, variations, or examples of the method(s) described below, and/or can be used to implement other methods.

2.4.1 First Magnetic Variation—Adaptor

As shown in FIGS. 8A-8C, the adaptor 210 includes a first region 211 configured to couple to a capture region of a sample processing chip 132 for capturing particles in single-particle format, a second region 212, and an internal cavity 220 passing from the first region to the second region. The adaptor 210 functions to provide structures that separate the magnet 230 from physically contacting wells or other sensitive material at the capture region of the sample processing cartridge 130, and to support application of a magnetic field to the capture region for retrieval of target material of the sample processing cartridge 130 by the system 200, by transmitting magnetic forces to a region of the adaptor 210 interfacing with the capture region of the sample processing cartridge 130. The adaptor 210 can also function to prevent sample cross contamination, by serving as a disposable component that can be discarded between uses of the system 200. Units of the adaptor can be stored at an embodiment of the tool container 40 supported by the deck 10 described above, or can be stored or staged by the system in another suitable manner. As shown in FIG. 8A, units of the adaptor 210 can be retained in position within a rack or portion of the tool container 40 until they are needed for use.

The adaptor 210 can be morphologically prismatic with an internal cavity 220, where the cross section of the adaptor 210 along its longitudinal axis is defined by a polygonal perimeter, an ellipsoidal perimeter, an amorphous perimeter, or a boundary of any other suitable shape (e.g., closed shape, open shape). The cross section of the adaptor 210 can complement a shape of a footprint of the capture region of the sample processing cartridge 130, but may alternatively not complement a shape corresponding to the capture region of the sample processing cartridge 130. The adaptor 210 can have a length from 0.5-8 cm and a width from 0.2-4 cm (e.g., corresponding to the shape of the capture region of the chip 201). The adaptor 210 preferably has a wall thickness that supports application of a magnetic force, from the magnet 230, to the capture region interfacing with the first region 211 of the adaptor 210. The wall thickness can be constant or non-constant along the length of the adaptor 210. In examples, the wall thickness can range from 0.2 to 3 mm thick; however, in other examples, the wall thickness can have any other suitable thickness. The surface of the adaptor that receives the magnetic particles is made smooth (e.g., surface finish better than $SPIB_1$) such that the small magnetic particles (1-3 micron) do not gets entrapped in the surface during the bead capture onto its surface and subsequent release to another receptacle.

The adaptor 210 can additionally or alternatively include structural features that enable operation modes of the system 200. For instance, in relation to release of the adaptor 210 from the support structure 240 (described in more detail below), the adaptor 210 can include a protrusion 214 configured to interface with the plunger subsystem 250, where a trigger of the plunger subsystem 250 can push against the protrusion 214 to release the adaptor 210 from the support system 240, once the plunger subsystem 250 is activated. The protrusion 214 can be a rim about the second region 212 of the adaptor 210, or can alternatively be defined by any other suitable morphology.

As described above, the adaptor 210 interfaces, at a first region 211, with an exposed capture region of the sample processing cartridge 130 (e.g., with lid 135 open to provide access to access region 134), in order to facilitate application of magnetic force to the capture region, and to enable drawing of target material (e.g., target material coupled to magnetic particles) into the adaptor 210 for further downstream processing. The adaptor 210 can thus include a seal at the first region 211, in order to facilitate mechanisms for drawing target material from the sample processing chip 132 to the adaptor 210. The seal can be a separate element or an element integrated with the adaptor 210. The adaptor 210 can, however, omit a seal at the first region 211. The adaptor 210 also couples, at a second region 212, to the support structure 240, for retention in position relative to the magnet 230, and for reversible coupling and removal from the support structure 240. Coupling of the adaptor 210 to other system components can occur with one or more of: a press fit, a snap fit, a friction fit, a male-female coupling interface, a screw, another fastener, a magnetic mechanism, and any other suitable mechanism.

The adaptor 210 can be composed of a polymeric material (e.g., plastic) that does not adversely affect the magnetic field applied by the magnet 230 during operation. The adaptor 210 can additionally or alternatively include (e.g., include particles of) or be composed of a material (e.g., metallic material) that is magnetic or can produce an induced magnetic field to support applications of use of the system 200. The adaptor 210 can additionally or alternatively be composed of any other suitable material. Distributions of the material(s) of the adaptor 210 can be homogenous or non-homogenous through the body of the adaptor, in relation to desired magnetic effects at the capture region of the chip 201. The internal cavity 220 of the adaptor 210 can include a medium (e.g., magnetic medium, etc.), or can alternatively not include any medium.

2.4.2 First Magnetic Variation—Magnet

As shown in FIGS. 8A-8C, the magnet 230 is configured to pass into the internal cavity 220 of the adaptor 210 and apply an attracting force to the capture region and target material captured at the sample processing cartridge 130 during operation. The magnet 230 functions to generate a magnetic field that can attract target material captured at the capture region of the sample processing chip 132 (e.g., coupled to magnetic particles within the capture region) toward the adaptor 210 for further processing. The magnet shape and pole configuration is such that nearly normal magnetic force is applied to majority of the target microwells from where entrapped particles are being removed.

The magnet 230 can be morphologically prismatic, where the cross section of the magnet 230 along its longitudinal axis is defined by a polygonal perimeter, an ellipsoidal perimeter, an amorphous perimeter, or a boundary of any other suitable shape (e.g., closed shape, open shape). In variations, the magnet can have a length from 0.25-5" and a width from 0.1-1". In a specific example, the magnet has a square cross section along its length and has a length of 2" and sides of 0.25" width. The magnet 230 of the specific example has a weight of 15.4 g.

The magnet 230 couples, at a first end, to the support structure 240, and passes into the internal cavity 210 of the adaptor 210. In variations, as shown in FIG. 2B, units of the magnet 230 (and corresponding adaptor 210) can have different dimensions to support different variations of the chip 201. For instance, a unit of the magnet 230 can have a small cross section (e.g., 0.25"×0.25") to support a chip variation with fewer microwells, and a unit of the magnet 230 can have a larger cross section (e.g., 0.375"×0.375" to support a chip variation with more microwells).

The magnet 230 is composed of a permanent magnetic material, but can alternatively be an electromagnet. In variations, the magnet 230 can be composed of one or more of: alnico, neodymium, neodymium iron boron, samarium cobalt, ferrite, and any other suitable magnetic material. The magnet 230 can additionally or alternatively include a plating material, in order to facilitate operations involving processing of biological samples or other samples. In a specific example, the magnet 230 is composed of neodymium iron boron (NdFeB, grade 42) with a nickel-based coating (e.g., nickel-copper-nickel coating).

The magnet 230 can have one or more magnetization directions, and in variations, can produce a pull and/or push force up to 10 lbs., with a surface field of up to 12,000 Gauss, an internal field up to 30,000 Gauss (e.g., BRmax of 30,000 Gauss), and an energy density (BHmax) of up to 90 MGOe. In a specific example, the magnet 230 has a magnetization direction through its thickness, a pull force of 5.58 lbs., a surface field of 6584 Gauss, a BRmax of 13,200

Gauss, and a BHmax of 42 MGOe. In terms of field, the magnet 230 of the specific example is magnetized through its length so the poles are one the 0.25"×0.25" ends of the magnet 230. However, the magnet 230 can alternatively be configured to produce any other suitable field.

2.4.3 First Magnetic Variation—Support Structure

As shown in FIGS. 8A and 8C, the support structure 240 is reversibly coupled to the second region of the adaptor 210 and to the magnet 230. The support structure functions to retain the magnet 230 in position, and to transition between operation modes for coupling and uncoupling the magnet 230 and adaptor 210. The support structure 240 can also function to transition between operation modes for drawing material out of the capture region of the sample processing cartridge 130 for downstream processing.

The support structure 240 can have a housing with a form factor similar to that of a manual pipettor, where the housing has a surface with a gripping region (e.g., series of protrusions and recesses) configured to complement a user's hand. Alternatively the support structure 240 can be configured to not be handled by a human operator, and can additionally or alternatively include features for interfacing with a robotic apparatus (e.g., interface of pipettor 174 coupled to gantry 170 described above) for automated target material retrieval from the capture region of the sample processing cartridge 130. A variation of this embodiment is described in more detail below, with various operation modes for material retrieval and processing.

As noted above, the support structure 240 of the system 200 can also include a plunger subsystem 250 coupled to an ejector proximal the magnet 230, wherein in a baseline operation mode the adaptor 210 is coupled to the support structure 240 and the plunger subsystem 250 is not activated, and in an ejecting mode, the adaptor 210 is released from the support structure 240 in response to activation of the plunger subsystem 250. As described above, the ejector can interface with the protrusion 214 of the adaptor 210, in order to release the adaptor 210 from the support structure 240 in the ejecting mode. Furthermore, in variations, the plunger subsystem 250 can also include structures that function to facilitate fluid dispensing and aspiration functions in order to dispense and/or retrieve material from the capture region of the chip 201. As such, variations of the plunger subsystem 250 can perform similar functions to that of a pipettor, in addition to supporting magnetic field application and adaptor release.

The support structure 240 can be composed of one or more polymeric materials (e.g., plastics) that are sanitizable (e.g., autoclavable, resistant to damage by ethanol, etc.) between uses of the system 200. However, the support structure 240 can alternatively be composed of another suitable material.

2.4.4 First Magnetic Variation—Guide

As shown in FIGS. 8A and 8C, the system 200 can include a guide 260 configured to retain the support structure 240 in position relative to the capture region of the sample processing chip 132 and to prevent physical contact between the magnet 230 and the capture region of the sample processing chip 132 during operation. The guide 260 thus functions to provide support about the support structure 240 and/or chip 201, during the retrieval process. As such, in one variation, the guide 260 can include recessed regions configured to receive the support structure 240 with coupled magnet 230 and adaptor 210, as well as the chip 201, in order to fix relative alignment between the capture region of the sample processing chip 132 and the adaptor 210. The guide ensures that the adaptor surface is placed above the microwells of the sample processing cartridge 130 by a fixed distance, (e.g., 25 microns, 100 microns, 0.5 mm, or 1 mm, or 2 mm, or 3 mm, or 4 mm, 5 mm, 6 mm, etc.). In another variation, as shown in FIG. 8C, the guide 260 can be configured to couple to the sample processing cartridge 130 and to position the adaptor 210 relative to the capture region of the chip 201, by only contacting the adaptor. The guide 260 can, however, be coupled to any other suitable portion of the system 200 to provide support.

The guide 260 can be composed of one or more polymeric materials (e.g., plastics) that are sanitizable (e.g., autoclavable, resistant to damage by ethanol, etc.) between uses of the system 200. However, the guide 260 can alternatively be composed of another suitable material. The guide 260 can also be a disposable portion of the system 200.

2.5 System—Second Variation for Retrieval and Processing by Magnetic Force

As shown in FIGS. 6A, 7B, and 9A-9C, a variation of the system 200' can include a variation of adaptor 210', magnet 230', and support structure 240' (e.g., of separation subsystem 160), which functions to facilitate separation and retrieval of target material from non-target material using magnetic forces. In variations, the separation subsystem 160 can include embodiments, variations, and examples of components described in applications incorporated by reference above and described in further detail below. However, other variations of the separation subsystem 160 can additionally or alternatively include other components.

2.5.1 Second Magnetic Variation—Adaptor

Figure 9A:
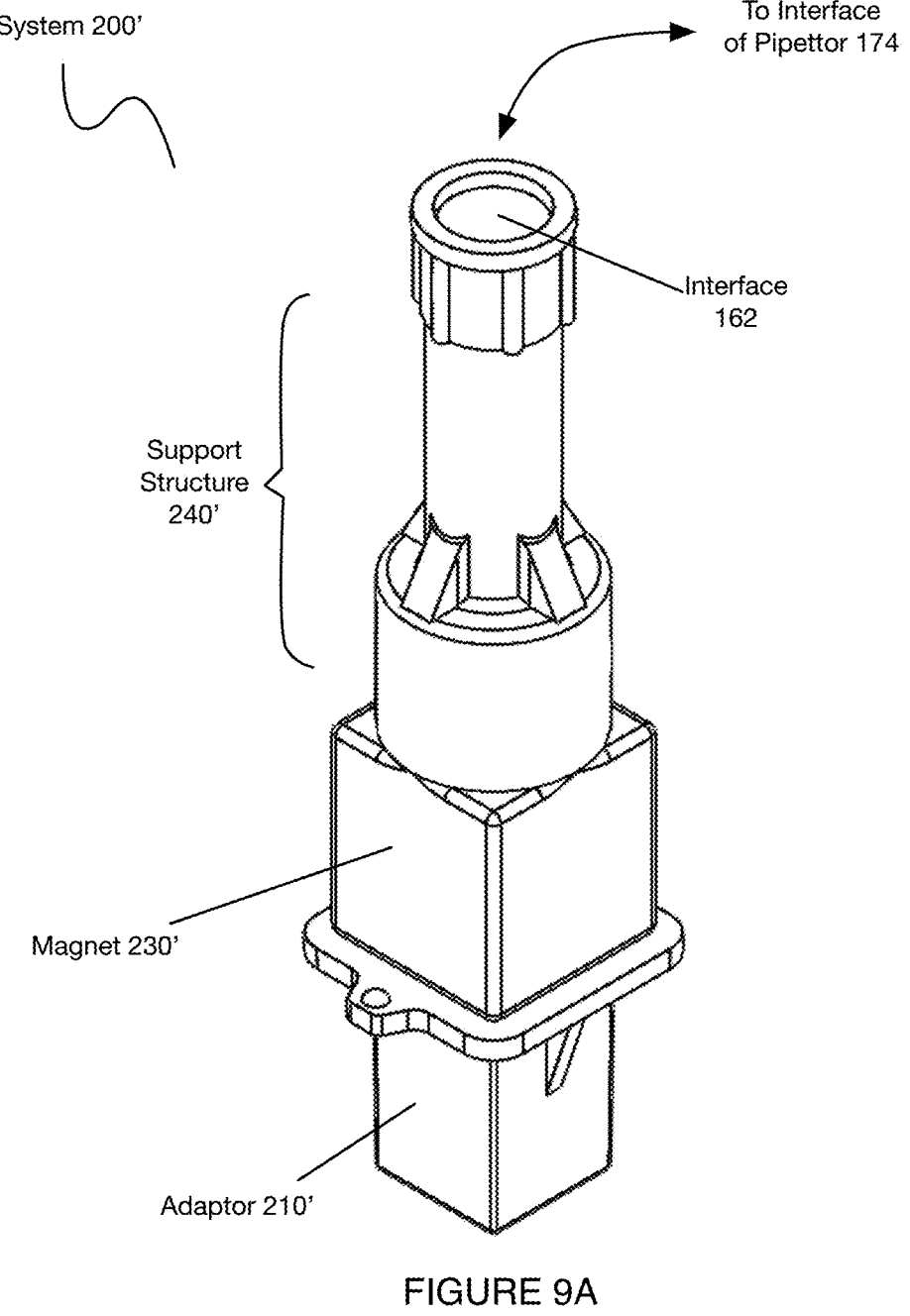
FIGS. 9A-9C depict a second magnetic variation of a system for target material retrieval.
Figure 9B:
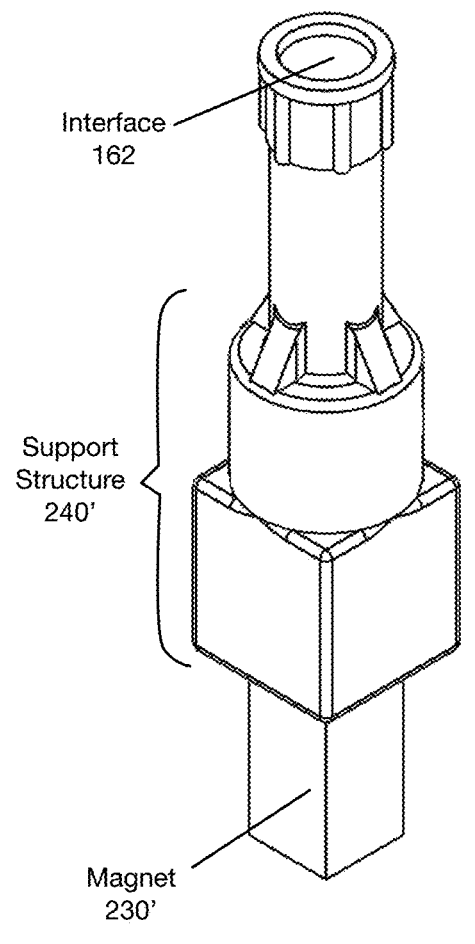
Figure 9C:
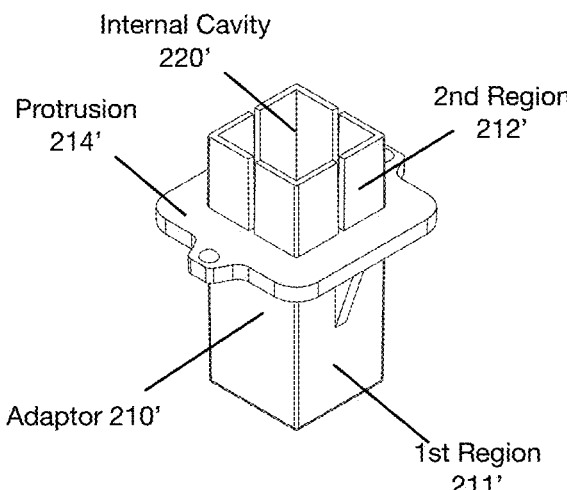

As shown in FIGS. 9A-9C, the adaptor 210' can include a first region 211 configured to interface with the sample processing chip 132, for instance, through access region 134, in order to enable retrieval of target material from the sample processing chip 132. The adaptor 210' can also include a second region 212' for coupling with the magnet 230' (e.g., magnetic distal portion) of support structure 240', and an internal cavity 220' passing from the first region to the second region. The adaptor 210' functions to provide structures that separate the magnet 230' and/or support structure 240' from physically contacting wells or other sensitive material of the sample processing chip 132, and to support application of a magnetic field to the desired regions for retrieval of target material (or non-target material). The adaptor 210' can also function to prevent sample cross contamination, by serving as a disposable component that can be discarded between uses of the system 200'.

The adaptor 210' can be morphologically prismatic with an internal cavity 220', where the cross section of the adaptor 210' along its longitudinal axis is defined by a polygonal perimeter, an ellipsoidal perimeter, an amorphous perimeter, or a boundary of any other suitable shape (e.g., closed shape, open shape). The cross section of the adaptor 210' can complement a shape of a footprint of the microwell region of the sample processing chip 132, but may alternatively not complement a shape corresponding to the sample processing chip 132. The adaptor 210' preferably has a wall thickness that supports application of a magnetic force, from the magnet 230', to the sample processing chip 132 interfacing with the first region 211' of the adaptor 210'. The wall thickness can be constant or non-constant along the length of the adaptor 210. In examples, the wall thickness can range from 0.2 to 3 mm thick; however, in other examples, the wall thickness can have any other suitable thickness. The surface of the adaptor 210' that receives the magnetic particles is made smooth (e.g., surface finish better than SPIB$_1$) such that small functionalized particles (e.g., 1-3 micron in characteristic dimension) do not get entrapped at the surface during capture and subsequent release to another receptacle (e.g., process container 20).

The adaptor 210' can additionally or alternatively include structural features that enable separation operation modes of the separation subsystem 160, described in more detail below. For instance, in relation to release of the adaptor 210' from the support structure 240', the adaptor 210' can include a protrusion 214' configured to allow another object (e.g., sleeve stripping tool 165 described in more detail below) to provide a force against the protrusion 214' to release the adaptor 210' from the support structure 240'.

As described above, the adaptor 210' interfaces, at a first region 211', with a capture region of the sample processing chip 132 exposed through access region 134, in order to facilitate application of magnetic force to the region, and to enable drawing of material (e.g., target or non-target material coupled to magnetic particles) to the adaptor 210' for further downstream processing. The magnetic sleeve 1410 can thus include a seal at the first region 211', in order to facilitate mechanisms for drawing target material from the sample processing chip 132 to the adaptor 210'. The seal can be a separate element or an element integrated with the adaptor 210'. The adaptor 210' can, however, omit a seal at the first region 211'.

The adaptor 210' can be composed of a polymeric material (e.g., plastic) that does not adversely affect the magnetic field applied by the magnet 230' during operation. The adaptor 210' can additionally or alternatively include (e.g., include particles of) or be composed of a material (e.g., metallic material) that is magnetic or can produce an induced magnetic field to support applications of use of the system 200'. The adaptor 210' can additionally or alternatively be composed of any other suitable material. Distributions of the material(s) of the adaptor 210' can be homogenous or non-homogenous through the body of the adaptor, in relation to desired magnetic effects at the capture region of the sample processing chip 132. The internal cavity 220' of the adaptor 210' can include a medium (e.g., magnetic medium, etc.), or can alternatively not include any medium.

2.5.2 Second Magnetic Variation—Support Structure and Magnet

In the variation shown in FIGS. 9A-9C, the system 200' can include a support structure 240' including an interface 162 to the fluid handling subsystem (e.g., pipette interface) of the gantry 170 described above, and magnet 230' configured to provide magnetic forces for target material separation. In this variation, the magnet 230' can be configured to couple with one or more units of the adaptor 210', in variations where the adaptor 210' is a disposable elements. Furthermore, the interface 162 can be configured to couple to a pipetting head coupled to the gantry 170 described in more detail below, in order to facilitate automation of target or non-target material retrieval by way of magnetic forces, fluid aspiration, and/or fluid delivery operations provided by the pipetting head. As such, the system 100 can include a separation mode in which the gantry 170 transports the support structure 240', coupled to the adaptor 210', between units of the sample processing cartridge 130 and the process container 20 for magnetic separation and processing of target material from a sample. Furthermore, embodiments of methods implemented using the separation subsystem 160 can produce rapid retrieval of target material, with a retrieval efficiency of >90% where only magnetic particles coupled to target material (or non-target material) of the sample are retrieved. The separation subsystem 160 can thus function to produce increased selective retrieval efficiency can thus reduce downstream costs in relation to processing reagent and other material costs (due to reduced volumes needed, due to reduced splits in biochemistry reactions) and processing burden.

As shown in FIG. 9A, the support structure can include an interface 162 to the fluid handling subsystem of the gantry 170 described below, where the interface includes a coupling region that complements a corresponding coupling region of the fluid handling subsystem. The coupling region of the interface 162 can operate by: a magnetic coupling mechanism; a press fit; a snap fit, a screwing mechanism; a male-female connection; or another suitable mechanism for providing reversible coupling with the fluid handling subsystem.

The magnet 230' of the support structure 240' can include or be composed of a material for providing a permanent magnet, or can alternatively be configured as an electromagnet (e.g., with coupling to suitable electronics of the system 100). In variations, the magnetic distal region 163 can be composed of one or more of: alnico, neodymium, neodymium iron boron, samarium cobalt, ferrite, and any other suitable magnetic material. In morphology, the magnet 230' can complement a morphology of the adaptor 210', such that units of the adaptor 210' can couple (e.g., reversibly couple) with the magnet 230'. Furthermore, the morphology and pole configuration of the magnet 230' is such that nearly normal magnetic force is applied to majority of the target microwells from where entrapped particles are being removed.

Figure 10A:
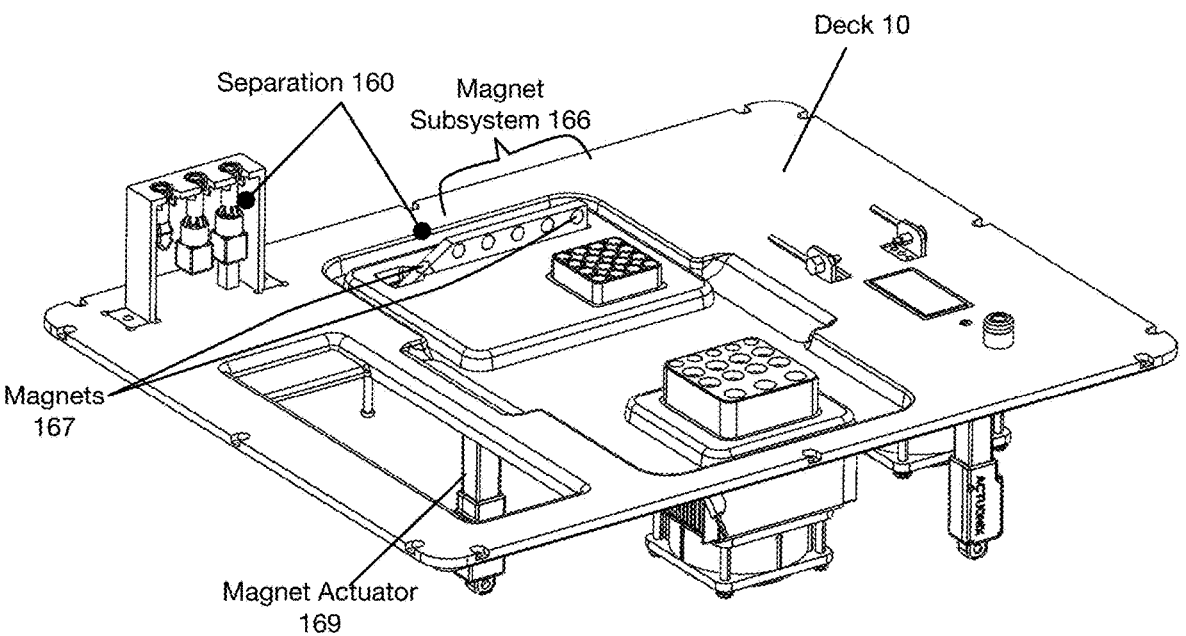
FIGS. 10A-10B depict variations of a subset of components used for material separation in a system for target material retrieval.
Figure 10B:
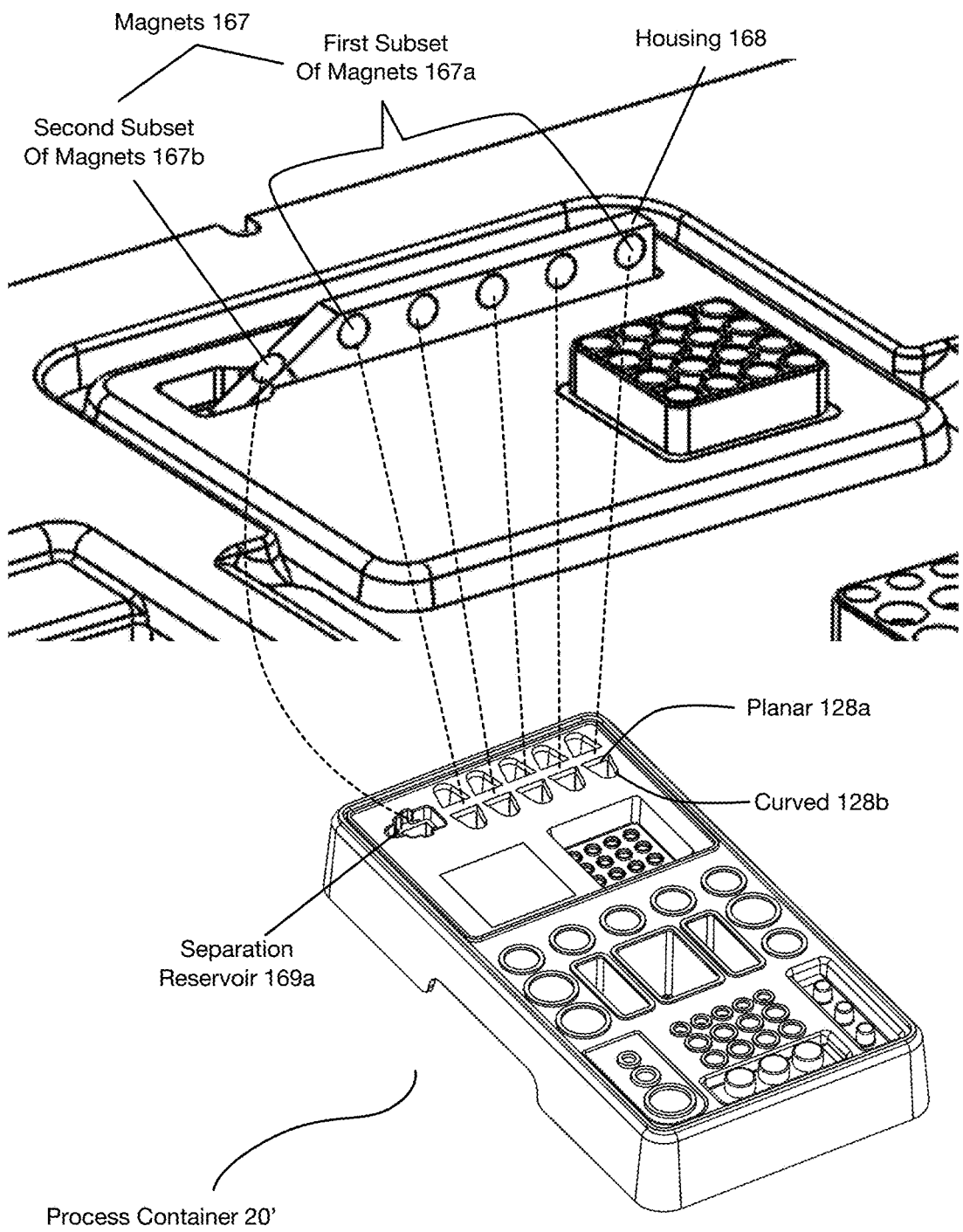

2.5.3 Second Magnetic Variation—Optional Separation Elements Involving Deck, Gantry, and/or Base As shown in FIGS. 6A, 7B, and 10A-10B, in variations, the separation subsystem 160 can include a magnet subsystem 166 including a set of magnets 167 within a housing 168, where the magnet subsystem 166 further includes a magnet actuator 169 configured to move the set of magnets 167 relative to the deck 10 (e.g., through in opening in the deck 10), and into/out of alignment with one or more separation reservoirs 129a, 129 of the process container 20 described above. The magnet actuator 169 can also be coupled to control circuitry (e.g., at the base 180). Furthermore, the magnet actuator 169 can be configured to transition the set of magnets between a retracted state and an extended state, wherein in the extended state, the set of magnets passes into the first region of the deck (e.g., as shown in FIGS. 10A and 10B). As such, the separation subsystem 160 can also include elements that are supported by the deck 10 and/or base 180, in order to enable operations for separating target material from non-target material.

In variations, the set of magnets 167 can include one or more permanent magnets and/or electromagnets (e.g., with coupling to suitable electronics of the system 100). Permanent magnets can be composed of one or more of: alnico, neodymium, neodymium iron boron, samarium cobalt, ferrite, and any other suitable magnetic material.

In the example shown in FIGS. 10A-10B, the set of magnets 167 can include a first subset of magnets 167a arranged in a linear array (e.g., for performance of purification operations at the process container 20'), where the positions of the first subset of magnets 167a correspond to positions of volumes of the fifth domain 25' for particle separation/purification, described in relation to the process container 20' above and workflows described in Section 3 below. In the example shown in FIG. 10A-10B, the set of magnets 167 also includes a second subset of magnets 167b (e.g., one or more magnets) displaced from or otherwise offset from an axis associated with the first subset of magnets 167a, in order to interact with a separation reservoir 129, 129a of the process container 20 (e.g., for initial bead retrieval). The set of magnets 167 can, however, be arranged in another suitable manner (e.g., in relation to distributed arrays, in relation to number, etc.) in relation to providing suitable interactions with separation reservoirs 129 of the process container 20 or other containers.

The housing 168 functions to surround the set of magnets 167, and to provide smooth operation in relation to transitioning the set of magnets 167 into/out of alignment with corresponding portions of the process container 20, 20'. Thus, as shown in FIG. 10B, in relation to configurations where there is a first subset of magnets 167a and a second subset of magnets 167b, the housing 168 can include a first surface (e.g., first planar surface) tracking the first subset of magnets 167a, and a second surface (e.g., second planar surface) tracking the second subset of magnets 167b, wherein the first surface 168a and the second surface 1681D are angled away from each other. In this variation, a pair of opposing walls can extend from the first surface and the second surface, in order to promote smooth operation (e.g., sliding operations) of the housing 168 and magnets through the deck 10 in order to interface with the process container 20, 20'.

In relation to the process container 20', as shown in FIG. 10B, volumes of the process container 20' configured for magnetic separation can each include a planar surface 128a, or other surface complementary to the housing 168 at sides configured to be closest to the housing 168 during operation (e.g., in the extended magnet states). Furthermore, volumes of the process container 20' configured for magnetic separation can each include a second surface 128b (e.g., curved surfaces) displaced away from the housing 168 for aspiration and/or delivery of fluids by a pipettor coupled to the gantry 170. Cross sections taken longitudinally through separation volumes/reservoirs 129, 129a of the reagent cartridge 120 can further be tapered toward a base of the process container 20, 20', such that separation operations require a lower volume of fluid and/or provide more efficient aspiration and separation of target from non-target material.

2.5.4 Second Magnetic Variation—Operation Modes

Figure 11A:
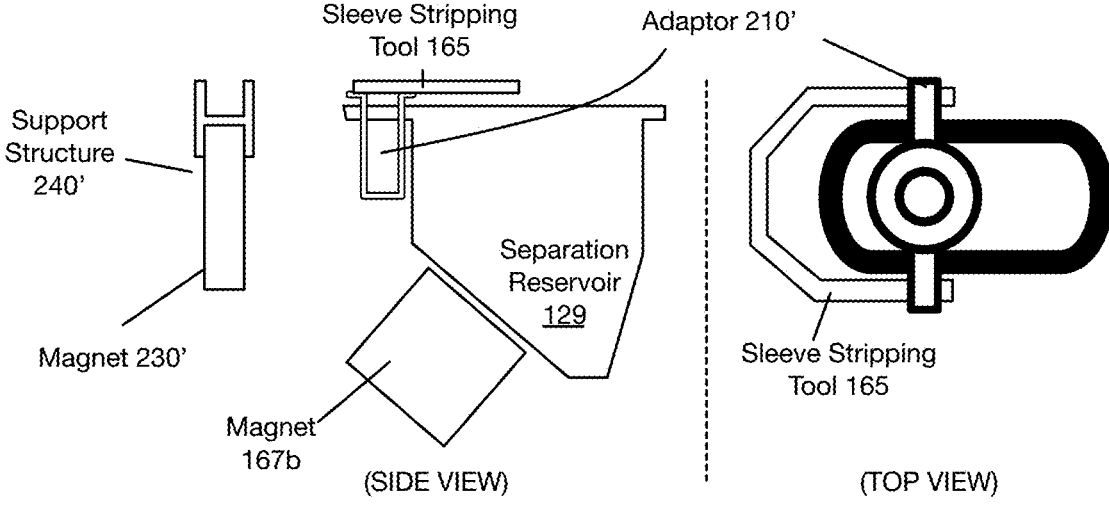
Figure 11B:
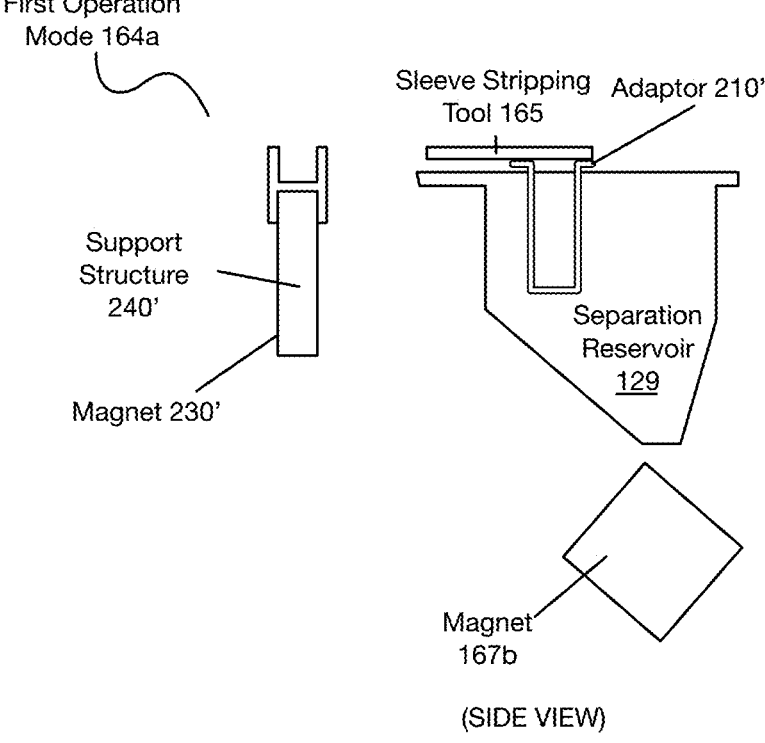
Figure 11C:
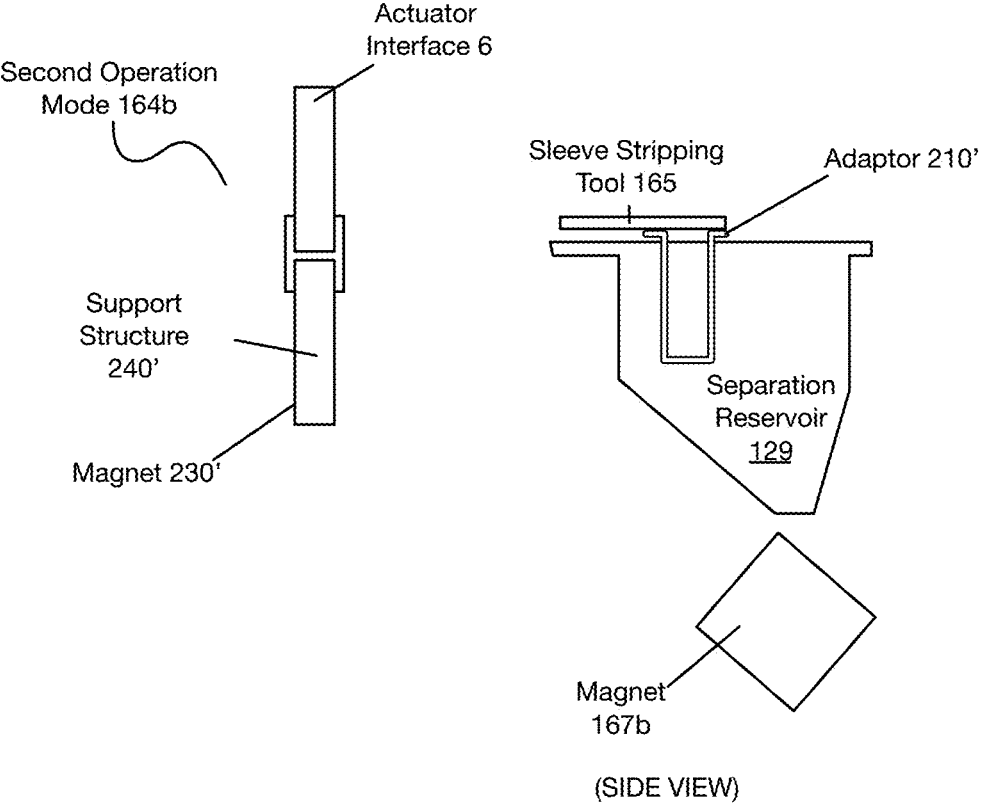
Figure 11D:
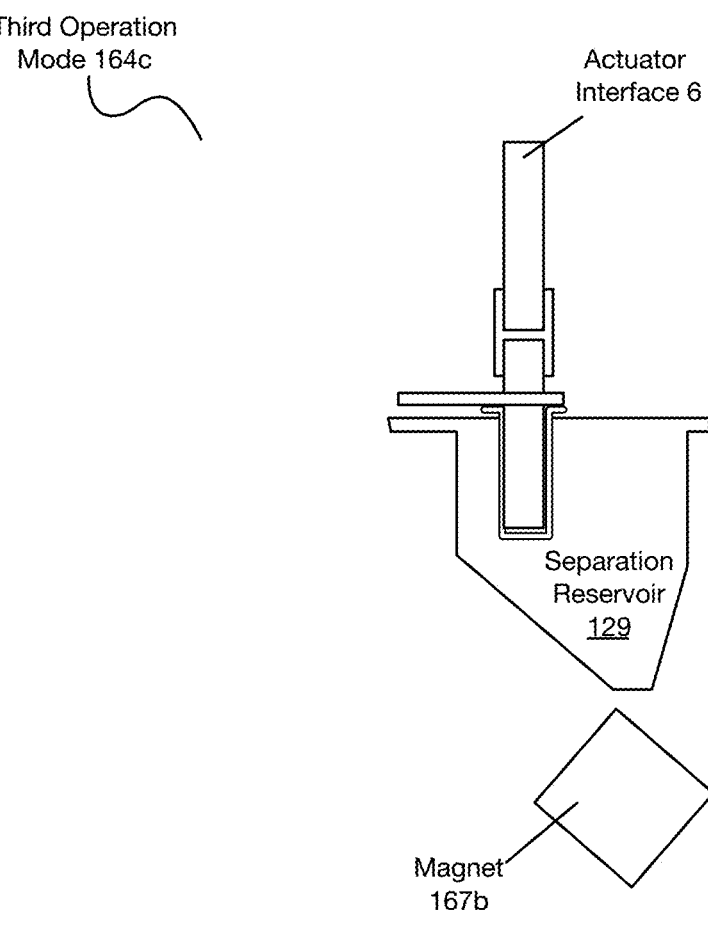
Figure 11F:
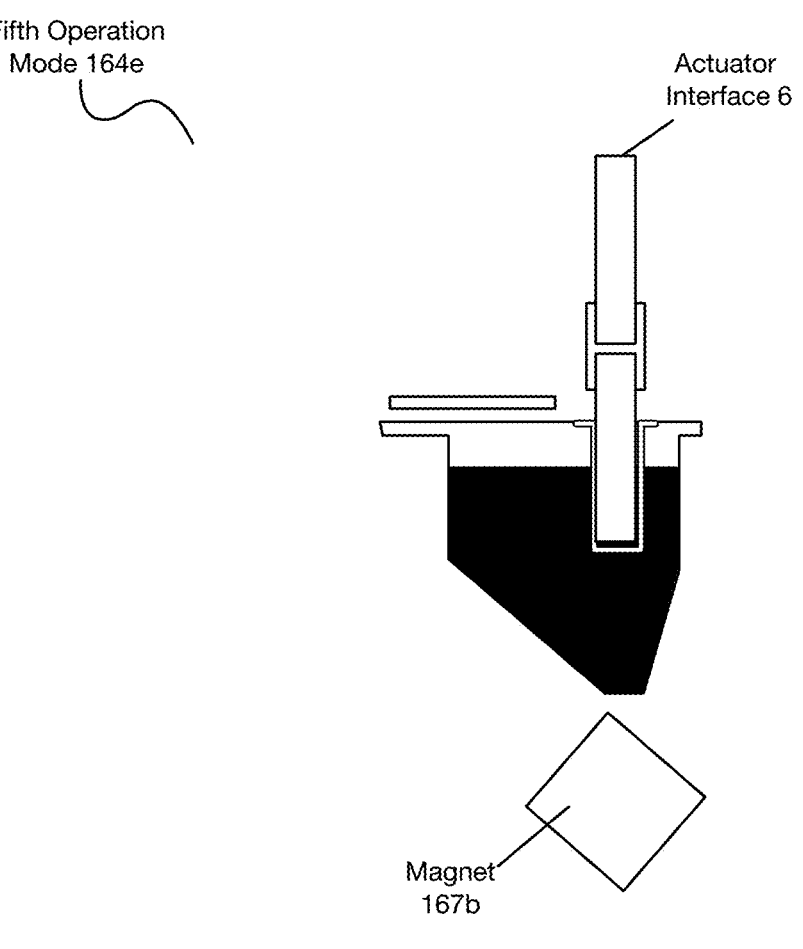
Figure 11H:
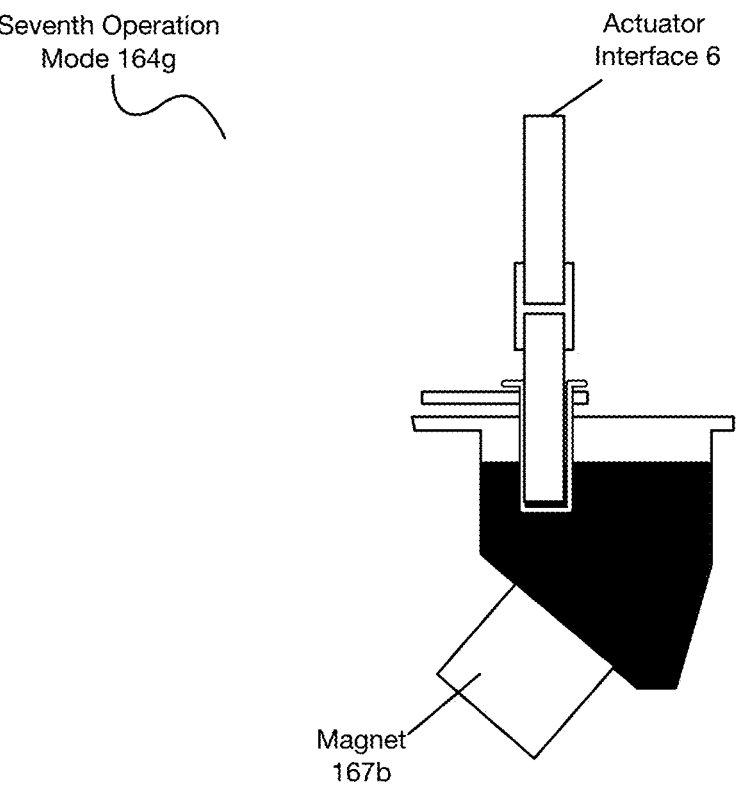
Figure 11I:
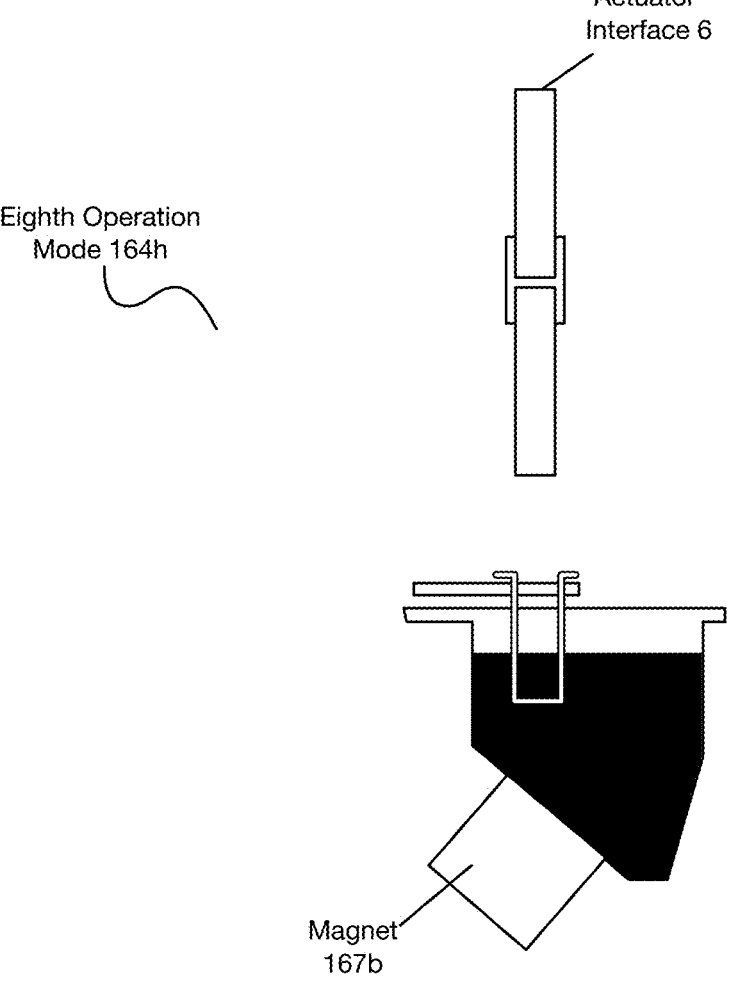
Figure 11J:
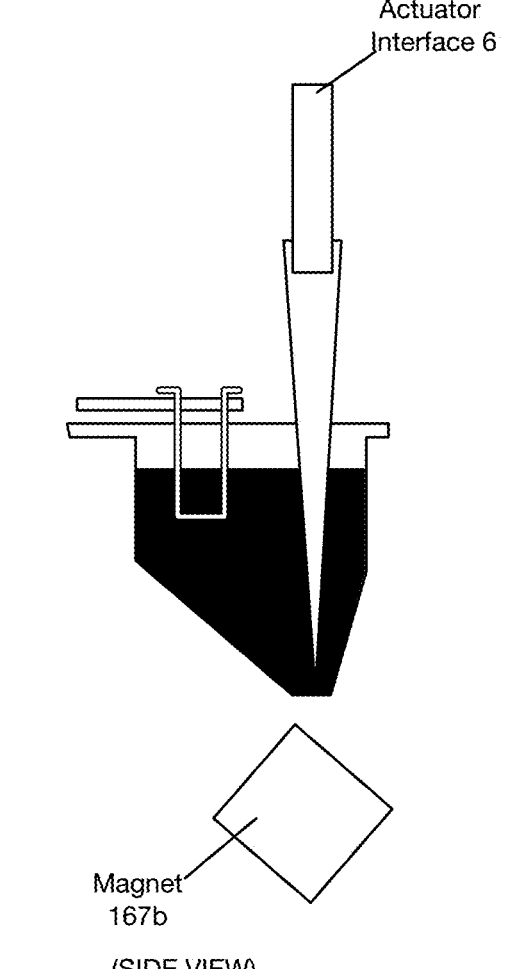
Figure 12A:
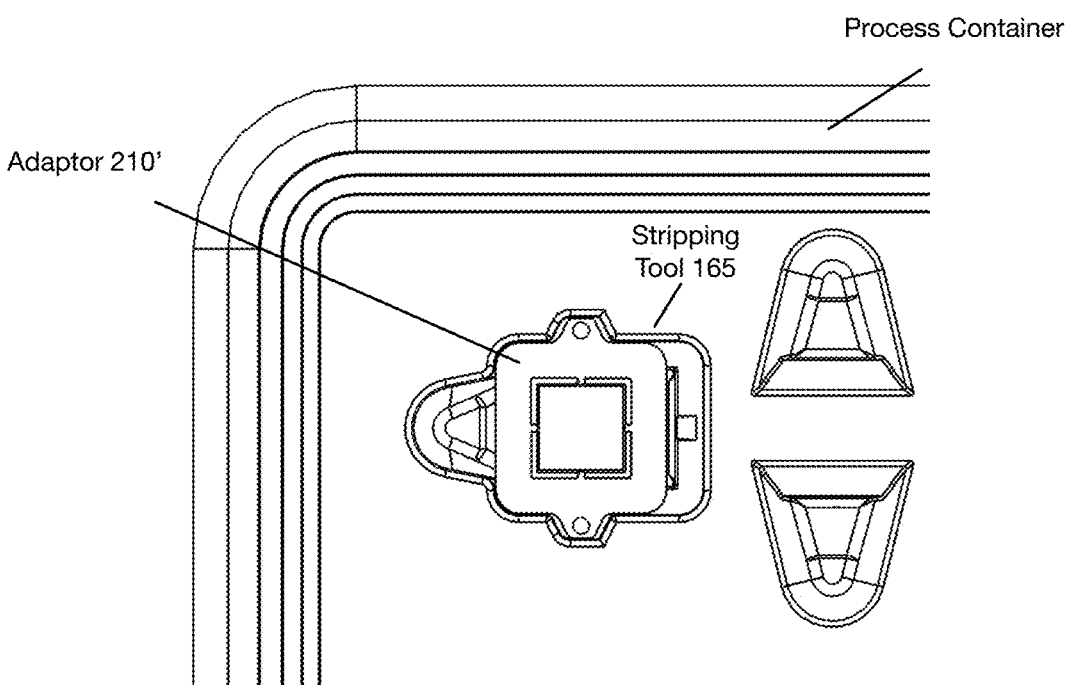
FIGS. 12A-12D depict views of components of a variation of a separation subsystem associated with a system for target material retrieval.
Figure 12B:
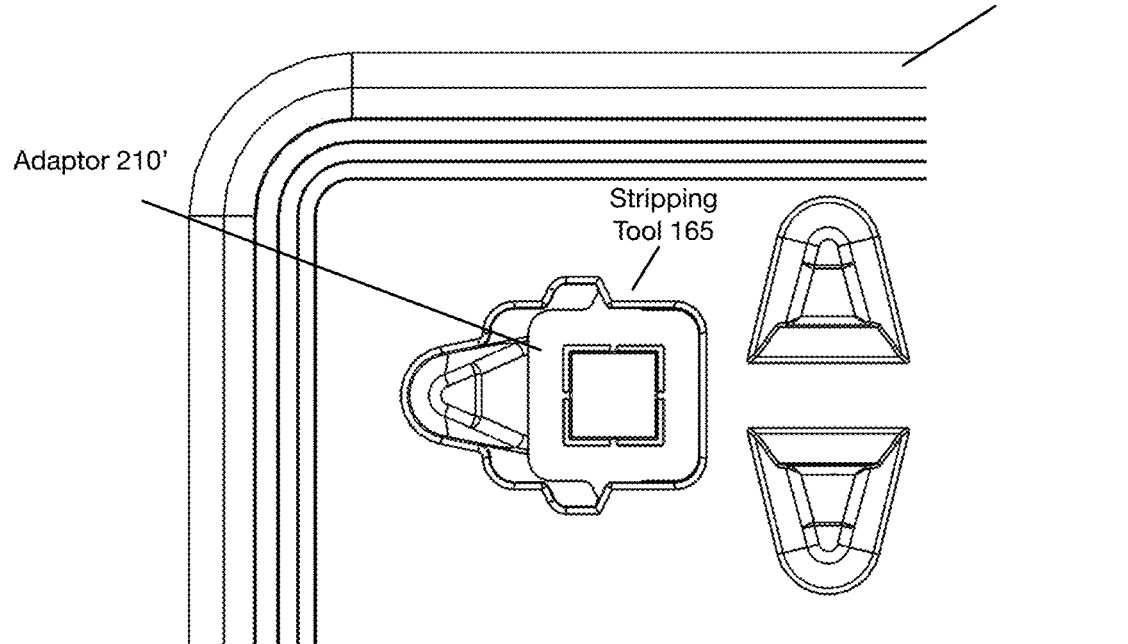
Figure 12C:
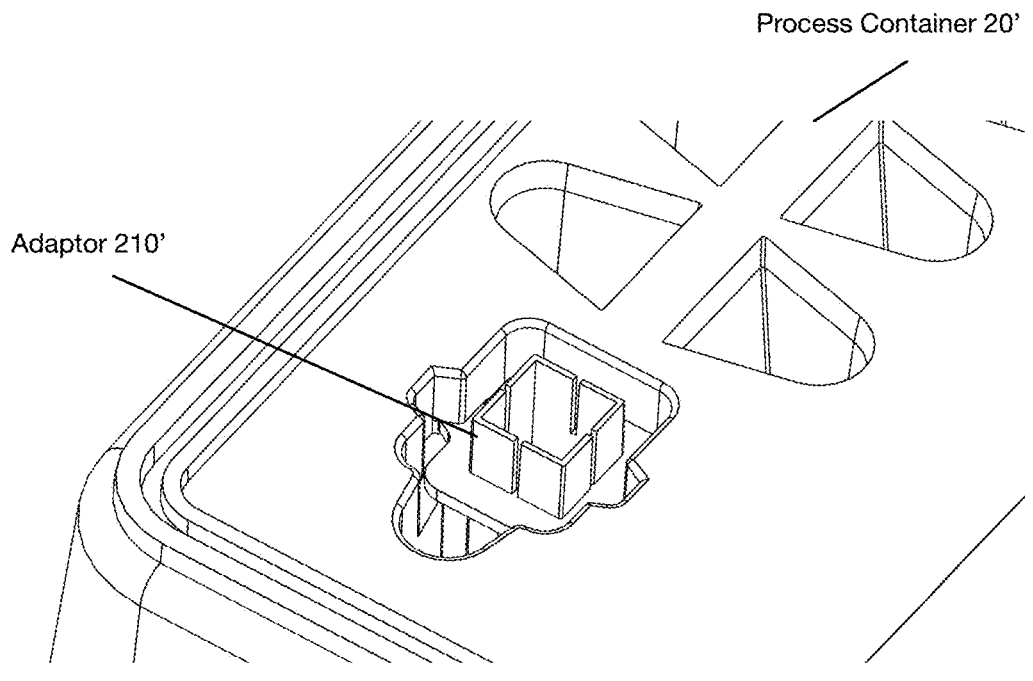
Figure 12D:
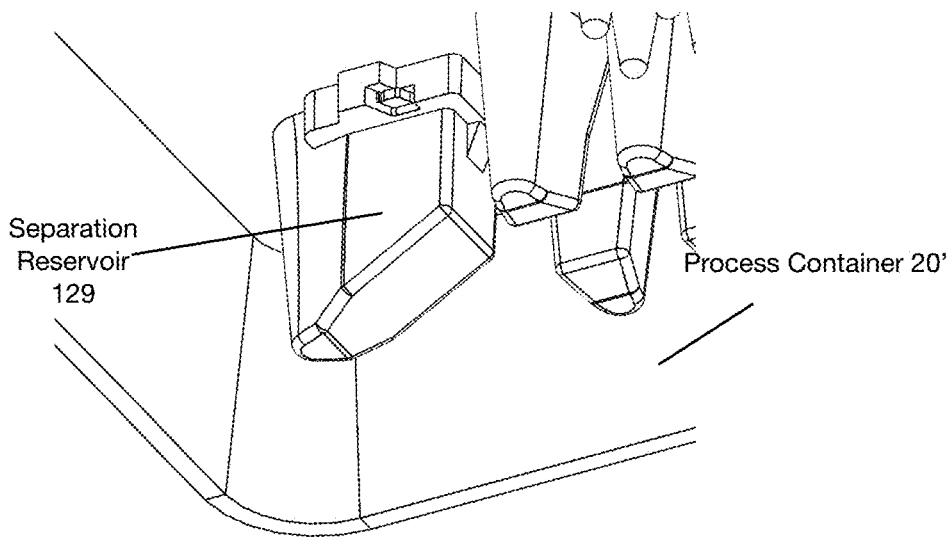

As shown in FIGS. 11A through 11J, the separation subsystem 160 can provide a sequence of operation modes for material separation, where, as shown in FIG. 12A, the operation modes involved specific system structure configurations of: a support structure 240' coupled with a pipetting head or other actuatable component (e.g., interface of pipettor 174 coupled to gantry 170), the support structure 240' coupled to a magnet 230', a unit of adaptor 210', a sleeve stripping tool 165, a separation reservoir 129, and a magnet 167b of the set of magnets 167 described above.

In more detail, as shown in FIG. 11B, the separation subsystem 160 can provide a first operation mode 164a, where the first operation mode 164a is a baseline operation mode in which the support structure 240' is uncoupled from a pipette interface or other actuatable component (e.g., described in relation to the gantry 170 below) and the magnet 230' of the support structure 240' is uncoupled from the adaptor 210'. The magnetic sleeve 1410 is further retained by sleeve stripping tool 165 above the separation reservoir 129 (or in variations, at another position), and the magnet 167b is displaced away from the separation reservoir 129 (e.g., by magnet actuator 169 described above). As such, in the first operation mode 164a, the system can stage the adaptor 210' in position near the separation reservoir 129, and stage the support structure 240' coupled to magnet 230' in preparation for separation and retrieval of target material from a sample.

As shown in FIG. 11C, the separation subsystem 160 can provide a second operation mode 164b, where the second operation mode 164b is an initializing operation mode in which the support structure 240' is coupled with a pipette interface or other actuator interface 6 (e.g., described in relation to the gantry 170 and pipettor 174) and the magnet 230' of the first body 161 is uncoupled from the adaptor 210'. The adaptor 210' is further retained by sleeve stripping tool 165 above the separation reservoir 129, and the magnet 167b is displaced away from the separation reservoir 129 (e.g., by magnet actuator 169 described above). As such, in the second operation mode 164b, the system stages the adaptor 210' in position near the separation reservoir 129, and couples the support structure 240', with magnet 230', to the pipettor 174 (e.g., through actuator interface 6) in preparation for separation and retrieval of target material from a sample.

As shown in FIG. 11D, the separation subsystem 160 can provide a third operation mode 164c, wherein, in the third operation mode 164c, the support structure 240' is coupled with a pipette interface or other actuator interface 6 (e.g., described in relation to the gantry 170 and pipettor 174) and moved into alignment with the separation reservoir 129. In the third operation mode 164c, the magnet 230' of the support structure 240' is coupled with the adaptor 210' above the separation reservoir 129 in the retained position of the adaptor 210'. In the third operation mode 164c, magnet 167b is displaced away from the separation reservoir 129 (e.g., by magnet actuator 169 described above). As such, in the third operation mode 164c, the system transitions the support structure 240' and magnet 230' (e.g., by way of pipettor 174) for coupling with the adaptor 210' retained near the separation reservoir 129, in preparation for separation and retrieval of target material from a sample.

As shown in FIG. 11E, the separation subsystem 160 can provide a fourth operation mode 164d, wherein, in the fourth operation mode 164d, the support structure 240' is coupled with a pipette interface or actuator interface 6 (e.g., described in relation to the gantry 170 and pipettor 174) and the magnet 230' of the support structure 240' is coupled with the adaptor 210' above the separation reservoir 129. In the fourth operation mode 164d, the pipetting head (or other actuatable component) moves the support structure 240' and magnet 230' coupled to the adaptor 210' out of the retained position provided by the sleeve stripping tool 165, to prepare for attraction of material (e.g., functionalized particles from the sample processing cartridge) derived from the sample. In the fourth operation mode 164d, magnet 167b is displaced away from the separation reservoir 129 (e.g., by magnet actuator 169 described above). As such, in the fourth operation mode 164d, the system transitions the support structure 240' and magnet 230' (e.g., by way of pipettor 174), coupled to the adaptor 210', out of the retained position and into separation reservoir 129, in preparation for separation and retrieval of target material from a sample.

As shown in FIG. 11F, the separation subsystem 160 can provide a fifth operation mode 164e, wherein, in the fifth operation mode 164e, the support structure 240' is coupled with a pipette interface or actuator interface 6 (e.g., described in relation to the gantry 170 and pipettor 174) and the magnet 230' is coupled to the adaptor 210' within separation reservoir 129. In the fifth operation mode 164d, the pipette interface (or other actuatable component) delivers fluid derived from the sample (e.g., lysed target material bound to target particles) into the separation reservoir 129, and the adaptor 210', still coupled with the support structure 240', is submerged within the fluid in the separation reservoir 129 to attract functionalized particles bound to target content. In the fifth operation mode 164e, magnet 167b is displaced away from the separation reservoir 129 (e.g., by magnet actuator 169 described above). As such, in the fifth operation mode 164e, the system configures the support structure 240', magnet 230', and adaptor 210', for attraction of target material delivered into the separation reservoir 129.

As shown in FIG. 11G, the separation subsystem 160 can provide a sixth operation mode 164f, wherein, in the sixth operation mode 164f, the support structure 240' is coupled with a pipette interface or actuator interface 6 (e.g., described in relation to the gantry 170 and pipettor 174) and the magnet 230' of the first body 161, still coupled with the adaptor 210', is moved by back into a retained position at the sleeve stripping tool 165. In the sixth operation mode 164f, the adaptor 210' (still coupled with target material/functionalized particles) is submerged within the fluid in the separation reservoir 129. In the sixth operation mode 164f, magnet 167b is displaced away from the separation reservoir 129 (e.g., by magnet actuator 169 described above). As such, in the sixth operation mode 164f, the system configures the support structure 240', magnet 230', and adaptor 210', for processing of target material bound to the adaptor 210'. For instance, while material is bound to the adaptor, the system can perform wash steps to remove non-target material, or other processes. Additionally or alternatively, the sixth operation mode 164f can prepare target material for transfer from the adaptor 210' to a region of the separation reservoir 129 proximal magnet 167b, for further processing (e.g., aspiration and delivery for amplification, etc.).

As shown in FIG. 11H, the separation subsystem 160 can provide a seventh operation mode 164g, wherein, in the seventh operation mode 164g, the support structure 240' is coupled with a pipette interface or actuator interface 6 (e.g., described in relation to the gantry 170 and pipettor 174) and the magnet 230' is coupled with the adaptor 210' in the retained position at the separation reservoir 129. In the seventh operation mode 164g, the adaptor 210', still coupled with the support structure, is retained in position at the sleeve stripping tool 165, and the adaptor 210' (with magnetically bound functionalized particles) is submerged within the fluid in the separation reservoir 129. In the seventh operation mode 164g, magnet 167b is displaced toward the separation reservoir 129 (e.g., by magnet actuator 169 described above) to prepare for attraction and retention of target or non-target material coupled to the functionalized particles of the fluid against a wall 128a of the separation reservoir 129. As such, the seventh operation mode 164g prepares target material for transfer from the adaptor 210' to a region of the separation reservoir 129 proximal magnet 167b, for further processing (e.g., aspiration and delivery for amplification, etc.).

As shown in FIG. 11I, the separation subsystem 160 can provide an eighth operation mode 164h, in which the support structure 240' is coupled with a pipette interface or actuator interface 6 (e.g., described in relation to the gantry 170 and pipettor 174), and moved away from the separation reservoir 129 to be replaced with a suitable tip from the tool container described above. In the eighth operation mode 164h, the magnet 230' of is uncoupled from the adaptor 210' above the separation reservoir 129, by having the pipetting head move the support structure 240' away from the adaptor 210' while the adaptor 210' is retained in position at the sleeve stripping tool 165. In the eighth operation mode 164h, the adaptor 210' is submerged within the fluid in the separation reservoir 129. In the eighth operation mode 164h, magnet 167b is still positioned in proximity to the separation reservoir 129 (e.g., by magnet actuator 169 described above) for retention of target or non-target material coupled to functionalized particles of the fluid against a wall 128*a* of the separation reservoir 129. In the eighth operation mode 164*h*, the magnet 167*b* draws target material toward the bottom of the separation reservoir 129 (e.g., for later extraction from the bottom by the pipettor, for retention while the pipettor draws material unbound by the magnet 167*b*). As such, the eighth operation mode 164*h* allows material captured at the adaptor 210' to be transmitted and temporarily retained at a region of the separation container 129 for further processing.

As shown in FIG. 11J, the separation subsystem 160 can provide a ninth operation mode 164*i*, wherein, in the ninth operation mode 164*i*, the pipetting head/actuator interface 6 is coupled with a suitable tip and moved into the separation reservoir 129 to aspirate material from the separation reservoir 129. In the ninth operation mode 164*i*, the adaptor 210' is still retained in position above the separation reservoir 129 at the sleeve stripping tool 165 and submerged within the fluid in the separation reservoir 129. In the ninth operation mode 164*i*, magnet 167*b* is moved away from the separation reservoir 129 (e.g., by magnet actuator 169 described above) in coordination with aspiration of material by the pipetting head. As such, the ninth operation mode 164*i* allows material captured at the adaptor 210' to be transmitted and temporarily retained at a region of the separation container 129 for further processing.

Variations of steps shown in FIGS. 11A-11J, related to target material retrieval and downstream processing can, however, be implemented using variations of system 200 described above, without involvement of the gantry 170 and/or the interface of pipettor 174.

FIGS. 12A through 12D depict additional views of configurations of a magnetic sleeve 1410 with respect to sleeve stripping tool 165 of a separation reservoir 129 of a process container 20, in relation to operation modes described above.

Variations of the separation subsystem 160 can, however, include elements and provide modes of operation for target material retrieval based upon one or more of: gravitational forces, buoyant forces, centrifugal forces, chemical separation, and/or any other suitable separation approaches. In yet another embodiment, target material retrieval operation by the separation subsystem 160 may be used to transfer target particles from the microwell chip to another substrate or another new empty microwell chip while keeping the relative spatial locations of the different particles being transferred.

2.6 System—Embodiments for Retrieval by Gravity-Associated Forces

Figure 13A:
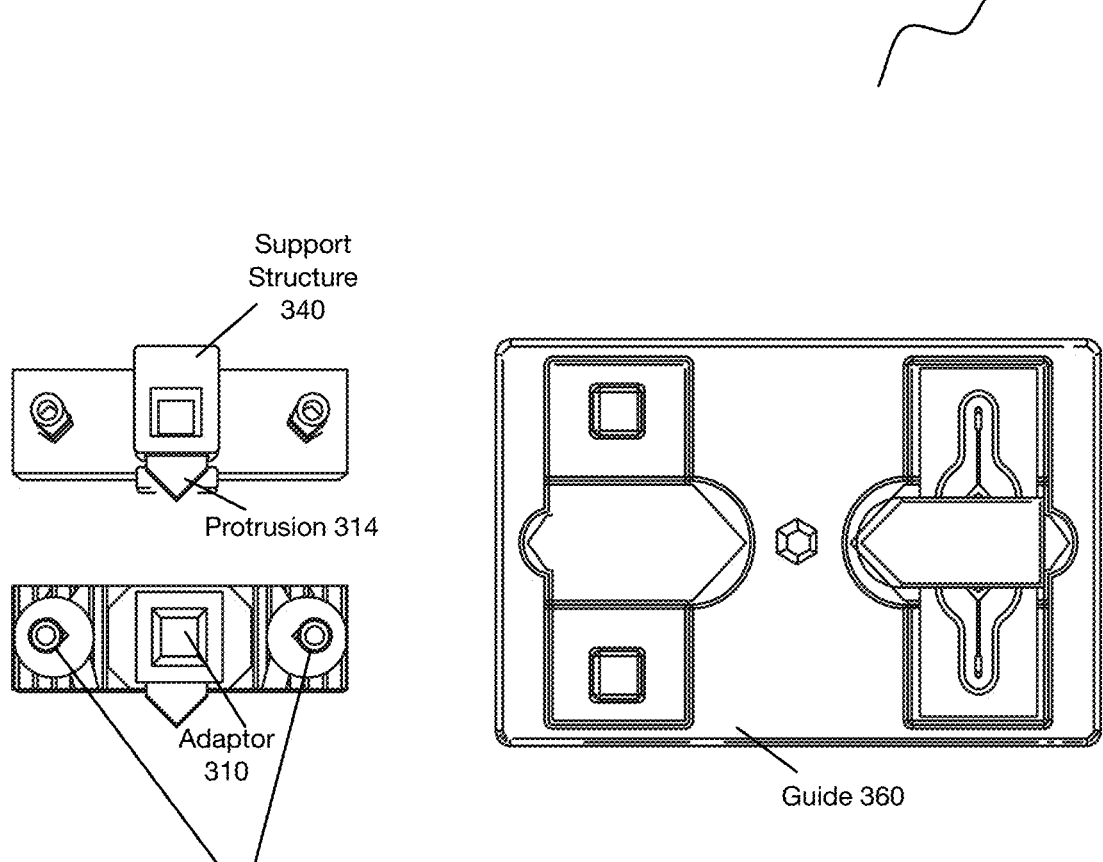
Figure 13B:
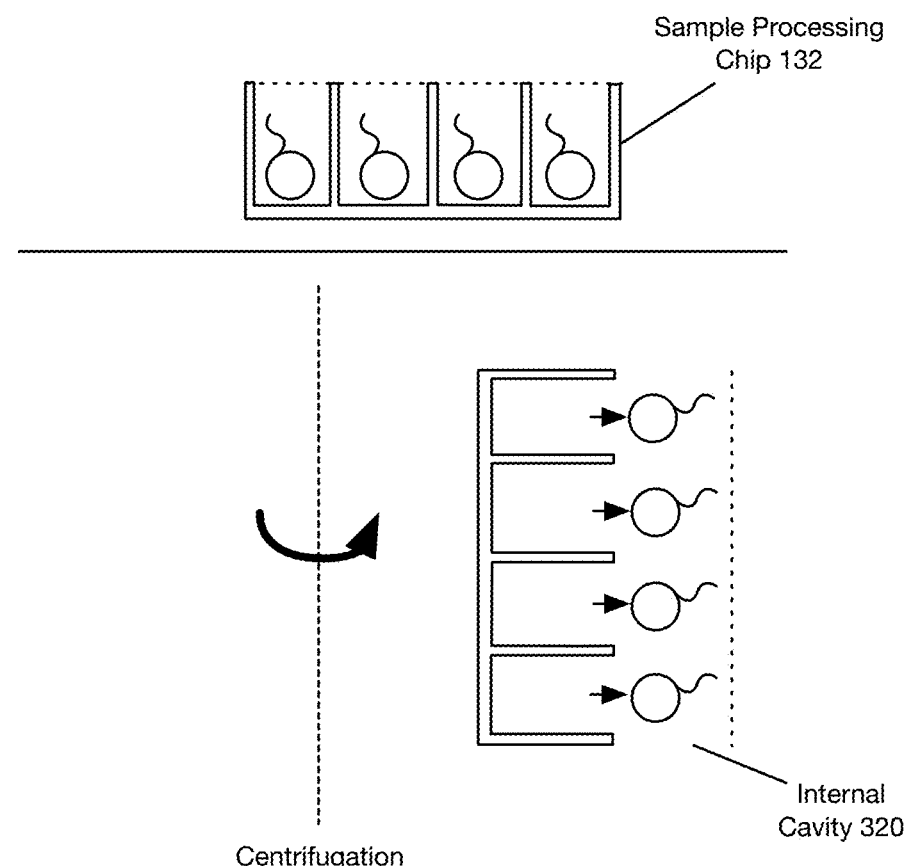
Figure 13C:
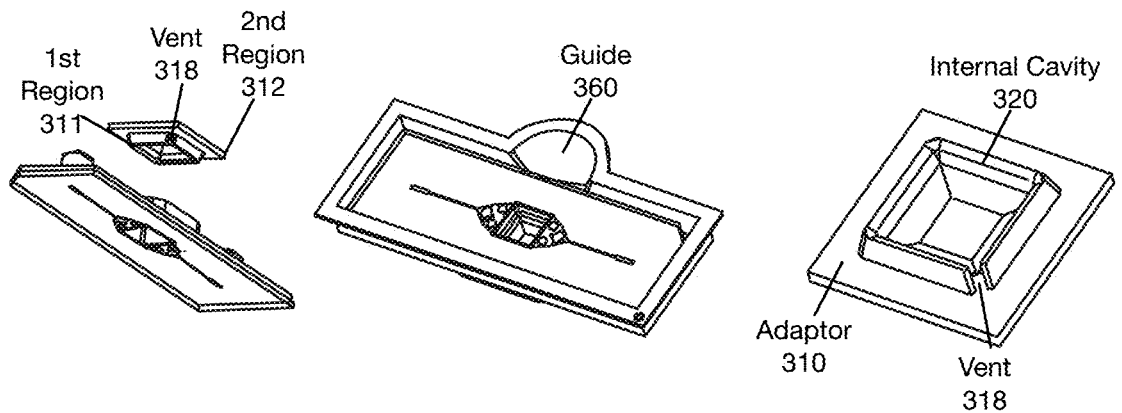

As shown in FIGS. 13A-13C, a variation of the system 300 includes an adaptor 310 including a first region 311 configured to couple to a capture region of a sample processing cartridge 130 for capturing particles in single-particle format, a second region 312, and an internal cavity 320 passing from the first region 311 to the second region 312; and a support structure 340 reversibly coupled to the second region of the adaptor 310. The adaptor 310 can also include a vent 318 operable to prevent retention of an air bubble between the internal cavity 320 of the adaptor 310 and the capture region of the sample processing chip 132.

The system 300 can also include one or more of: a set of plugs 350 configured to couple an inlet and/or an outlet fluidly coupled to the capture region of the sample processing chip 132 (e.g., directly, or through a manifold device); and a guide 360 including a recess complementary to the sample processing chip 132 and the adaptor 310, where the guide 360 is configured to retain the sample processing chip 132 and coupled adaptor 310 within a centrifuge apparatus for application of a gravity-associated force, through centrifugation, to contents of the capture region of the sample processing chip 132 and to the adaptor 310. The guide 360 can also function to prevent physical contact between a centrifuge apparatus and the sample processing chip 132 during operation.

The system 300 functions to allow an applied gravity-associated force to the capture region of the sample processing chip 132, as shown in FIG. 13B, in order to provide a directional force for delivering target material within the capture region, into the adaptor 310. Embodiments of methods implemented with the system 300 can produce retrieval of target material in 2-3 minutes of manual operation time (and ~15 minutes total time), with a retrieval efficiency of ~85-95%. The system 300 can thus function to provide a rapid method (in relation to manual operation time and total operation time) with high retrieval efficiency. The system 300 can implement one or more embodiments, variations, or examples of the method(s) described below, and/or can be used to implement other methods.

2.6.1 Adaptor

As shown in FIGS. 13A-13C, the adaptor 310 includes a first region 311 configured to couple to a capture region of a sample processing cartridge 130 for capturing particles in single-particle format, a second region 312, and an internal cavity 320 passing from the first region to the second region. The adaptor 310 functions to provide structures for allowing target material to be delivered from the capture region of the sample processing cartridge 130 in a manner that promotes easy retrieval of the target material from the adaptor 310, and to support application of a gravity-associated force to the capture region for transfer of target material of the sample processing chip 132 into the adaptor 310. The adaptor 310 can also function to prevent air bubbles and/or other obstructions from forming obstacles between the capture region of the sample processing cartridge 130 and the internal cavity 320 of the adaptor 310. The adaptor 310 can also function to prevent sample cross contamination, by serving as a disposable component that can be discarded between uses of the system 300.

The adaptor 310 has an internal cavity 320 with a concave surface facing toward the capture region of the sample processing chip 132 (when the adaptor 310 is coupled to the sample processing chip 132). The concave surface functions to define a volume for receiving and enabling force-based separation of target material from other components captured within the capture region of the chip 310. In variations, the volume of the internal cavity 320 can be from 0.1 microliters to 5 mL; however, in alternative variations, the volume of the internal cavity can define another volume.

In variations, the surface of the internal cavity 320 can include textures (e.g., dimples or other recesses, chambers, etc.), binding agents (e.g., chemical agents, charged agents, etc.) and/or other features that facilitate preferential retention of target material at the internal cavity 320 of the adaptor 320 after application of the applied force.

As shown in FIG. 13A, the adaptor 310 also includes a vent 318 configured to allow air (or other gases) to be released from within the internal cavity 320, after the adaptor 310 is coupled to the chip 310, in order to prevent air (or other gases) from creating a barrier to separation of target material from wells of the capture region of the sample processing chip 132, with application of the applied force. The vent 318 can be placed at a peripheral region of the adaptor 310, or can alternatively be placed at another suitable region of the adaptor. In relation to the applied force, the vent can be placed in an orientation that prevents target material from leaving the internal cavity 320 and through the vent 318; however, vent 318 can alternatively be placed in another orientation. The adaptor 310 can also include multiple vents or other bubble-releasing features (e.g., valves) and/or self-sealing material sections through which a needle can be pierced and air bubble extracted.

The adaptor 310 preferably has a wall thickness suitable for magnitudes of force used for separation of target material. In examples, the wall thickness can range from 0.2 to 3 mm thick; however, in other examples, the wall thickness can have any other suitable thickness.

The adaptor 310 can additionally or alternatively include structural features that enable operation modes of the system 300. For instance, in relation to coupling and release of the adaptor 310 from the capture region of the sample processing cartridge 130, the adaptor 310 can include a protrusion 314 (e.g., tab) that can be used to facilitate coupling and uncoupling of the adaptor 310 from the sample processing chip 132.

As described above, the adaptor 310 couples, at a first region 311, to an exposed capture region of the sample processing cartridge 130, in order to form a volume for separation and retrieval of target material from the capture region with application of gravity-associated force. The adaptor 310 can include a seal at the first region 311, in order prevent material from leaking at interfaces between the sample processing chip 132 and the adaptor 310. The seal can be a separate element or an element integrated with the adaptor 310. The adaptor 310 can, however, omit a seal at the first region 311. The adaptor 310 also couples, at a second region 312, to the support structure 340, for retention of the adaptor 310 in position at the sample processing chip 132, and for reversible coupling and removal from the support structure 340 and the sample processing chip 132. Coupling of the adaptor 310 to other system components can occur with one or more of: a press fit, a snap fit, a compression fit, a friction fit, a male-female coupling interface, a screw, another fastener, a magnetic mechanism, and any other suitable mechanism.

The adaptor 310 can be composed of a polymeric material (e.g., plastic, elastomer) that can undergo elastic deformation in order to facilitate removal of air or other gases trapped within the adaptor 310. The adaptor 210 can additionally or alternatively include (e.g., include particles of) or be composed of another material (e.g., non-polymeric material, metal, ceramic, etc.) that has functionality for promoting separation of target material from non-target material captured within the capture region of the sample processing chip 132. The adaptor 310 can additionally or alternatively be composed of any other suitable material.

2.6.2 Support Structure

As shown in FIGS. 13A and 13C, the support structure 340 is reversibly coupled to the second region 312 of the adaptor 310. The support structure 340 functions to retain the assembly of the sample processing chip 132 and the adaptor 310 in position, and to transition between operation modes for coupling and uncoupling the sample processing chip 132, adaptor 310, and/or guide 360 (described in more detail below).

The support structure 340 can have a form factor for clamping the assembly of the sample processing cartridge 130 and the adaptor 310 together in a manner that prevents material from leaking at the interface between the sample processing cartridge 130 and the adaptor 310. In one variation, the support structure 340 can thus have the form of a clamshell, where terminal opposing regions include clamping structures for clamping the assembly of the adaptor 310 and the sample processing chip 132 together. The support structure 340 can also have an opening that allows contents of the adaptor 310 and/or capture region of the sample processing chip 132 to be observed during processing.

The support structure 340 can be composed of one or more polymeric materials (e.g., plastics) that are sanitizable (e.g., autoclavable, resistant to damage by ethanol, etc.) between uses of the system 300. However, the support structure 340 can alternatively be composed of another suitable material. Furthermore, the support structure 340 can be a disposable or non-disposable component of the system 300.

2.6.3 Set of Plugs and Guide

Figure 3A:
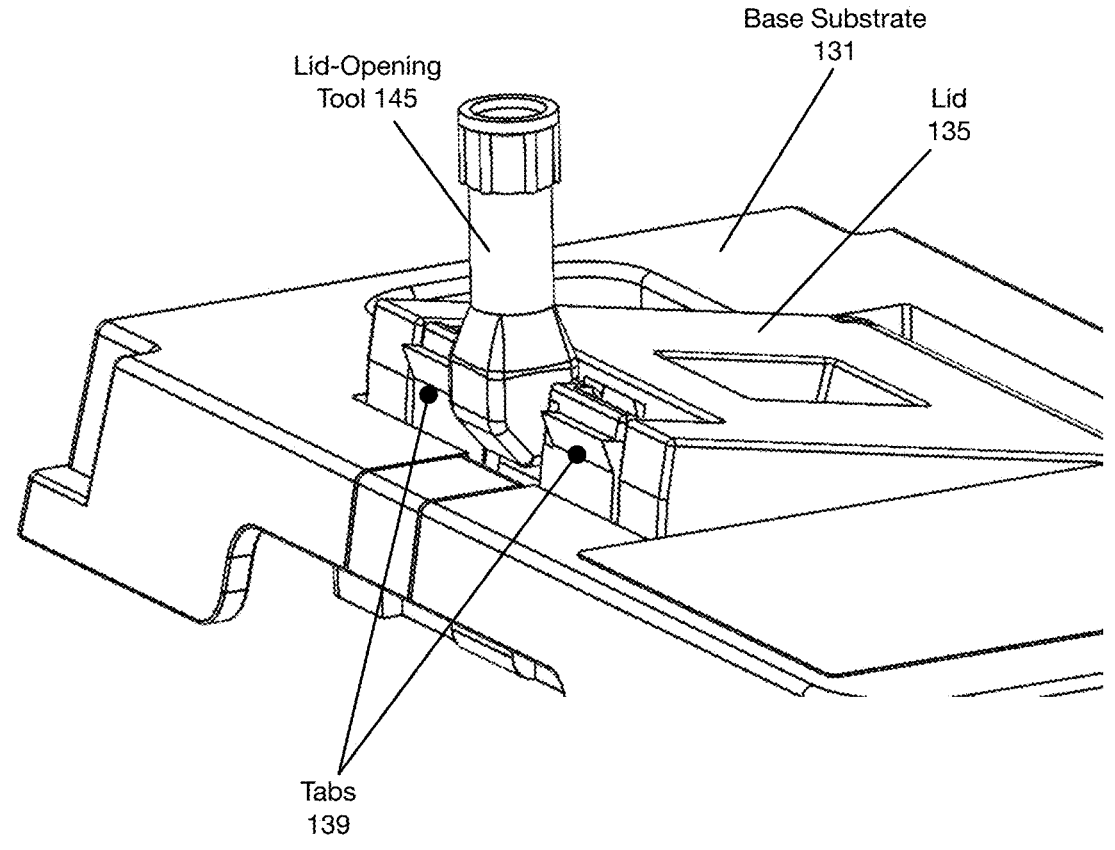
FIGS. 3A-3C depict operation modes of a lid-opening tool associated with the sample processing cartridge shown in FIGS. 2A-2C.
Figure 3B:
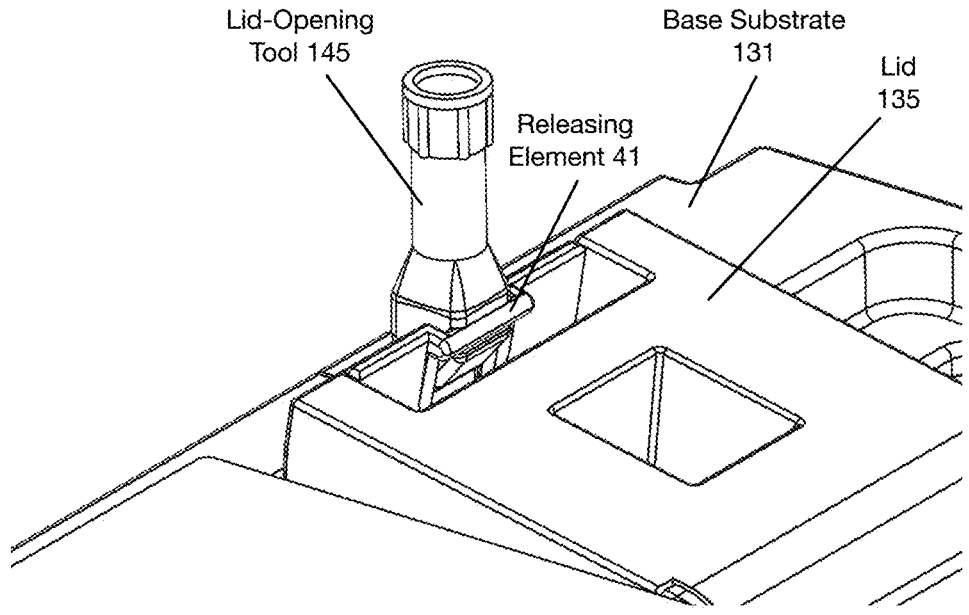
Figure 3C:
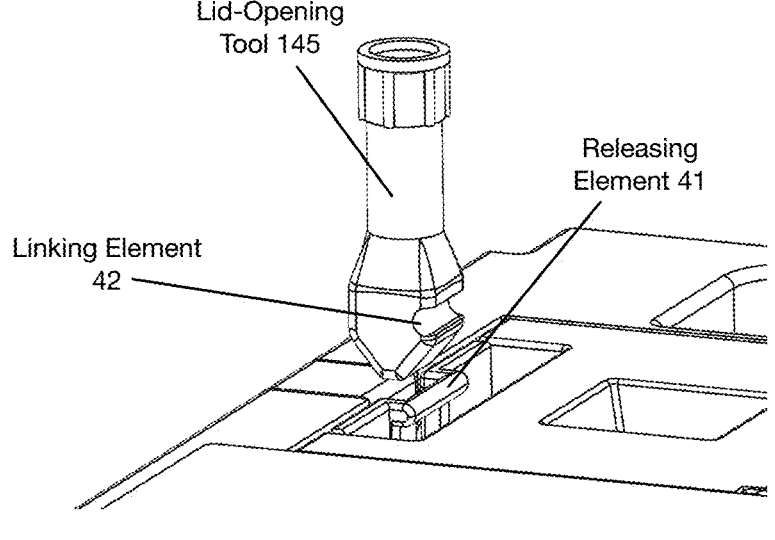

As shown in FIG. 3A, the system 300 can also include a set of plugs 350 configured to couple an inlet and/or an outlet fluidly coupled to the capture region of the sample processing chip 132 (e.g., directly, or through a manifold device). In embodiments where the sample processing chip 132 (described above) includes a manifold or other substrate for fluid delivery into and from the sample processing chip 132, the set of plugs 350 can couple to the inlet(s) and outlet(s) of the manifold. Additionally or alternatively, the set of plugs 350 can couple directly to an inlet and/or outlet of the sample processing chip 132. Coupling of the set of plugs 350 to other system components can occur with one or more of: a press fit, a snap fit, a friction fit, a male-female coupling interface, a screw, another fastener, a magnetic mechanism, and any other suitable mechanism.

The set of plugs 350 can be composed of one or more polymeric materials (e.g., plastics) that are elastomeric and/ or sanitizable (e.g., autoclavable, resistant to damage by ethanol, etc.) between uses of the system 300. However, the set of plugs can alternatively be composed of another suitable material. Furthermore, the set of plugs 350 can be a disposable or non-disposable component of the system 300.

As shown in FIGS. 13A and 13C, the system 300 can also include a guide 360 including a recess complementary to the sample processing chip 132 and the adaptor 310, where the guide 360 is configured to retain the sample processing chip 132 and coupled adaptor 310 within a centrifuge apparatus for application of a gravity-associated force, through centrifugation, to contents of the capture region of the sample processing chip 132 and to the adaptor 310. The guide 360 can also function to prevent physical contact between a centrifuge apparatus and the sample processing chip 132 during operation. The recess of the guide 360 preferably allows the entire sample processing chip 132 and adaptor 310 assembly to be seated within the recess; however, the recess of the guide 360 can alternatively be configured to receive only a portion of the sample processing chip 132 and/or adaptor 310.

As shown in FIG. 13C, the recess can include an extended region not contacting the sample processing chip 132 and/or adaptor 310, where the extended region facilitates placement and removal of the chip assembly within the recess by an operator. Coupling of the sample processing chip 132 and/or adaptor 310 assembly to the recess of the guide 360 can occur with one or more of: a press fit, a snap fit, a compression fit, a friction fit, a male-female coupling interface, a screw, another fastener, a magnetic mechanism, and any other suitable mechanism.

The guide 360 can be composed of one or more polymeric materials (e.g., plastics) that are rigid and/or sanitizable (e.g., autoclavable, resistant to damage by ethanol, etc.)

between uses of the system 300. However, the guide 360 can alternatively be composed of another suitable material. Furthermore, the set of plugs 350 can be a disposable or non-disposable component of the system 300.

2.7 System—Conclusion

The system(s) described can additionally or alternatively include other components that facilitate target material retrieval from a capture region of a chip. The system(s) described can implement one or more embodiments, variations, and examples of the method(s) described below, or any other suitable method.

3. METHOD

As shown in FIG. 14, embodiments of a method 400 for target material retrieval include: capturing a set of particles, in single-particle format, at a set of wells distributed across a substrate at a capture region 410; supporting an environment for processing target material of the set of particles within the capture region, according to a set of operations 420; forming an assembly with an adaptor configured to interact with (e.g., couple to) to the substrate 430; transmitting a force to the adaptor and the capture region, thereby releasing target material of the set of particles into the adaptor 440; and releasing target material of the set of particles for capture by the adaptor 450.

Embodiments, variations, and examples of the method 400 function to provide mechanisms for efficient retrieval of target material from a high-density capture device (e.g., microwell chip), where the high-density capture device includes a high-density array of high-aspect ratio microwells, in order to promote increased efficiency in captured single cell-bead pairing efficiency. Embodiments of the method 400 can also function to reduce manual burden in relation to retrieval of target material from the high-density capture device. Embodiments of the method 400 can also function to increase the efficiency at which target material is retrieved from the high-density capture device, and the efficiency at which non-target material is retained at the capture device.

The method 400 can process target material from cells captured in single cell format at a capture region of a chip, as described above. The cells can include any or all of mammalian cells (e.g., human cells, mouse cells, etc.), embryos, stem cells, plant cells, microbes or any other suitable kind of cells. The target material can include material associated with the cells, tissue, nuclei or cell-free nucleic acids (e.g., target lysate, mRNA, RNA, DNA, proteins, glycans, metabolites etc.) or particles bound with cellular or cell-free biomarkers. Additionally or alternatively, the method 400 can be configured to process particles (e.g., beads, probes, nucleotides, oligonucleotides, polynucleotides, etc.), reagents, or any other suitable materials as target materials for further processing. The method also can be configured to selectively remove multiple target particles simultaneously from a surface seeded with multitude of particles by selectively binding the target particles with other carrier particles that can be carried to another position by moving the carrier particles with a mechanism that moves the carrier particles.

The method 400 can be implemented by embodiments of the systems described above, and/or any other suitable system components.

4.1 Method—Capture and Processing Target Material

Block 410 recites: capturing a set of particles, in single-particle format, at a set of wells distributed across a substrate at a capture region. Block 410 functions to process content of a sample in order to isolate particles (e.g., single cells, cells co-captured with functional particles, etc.) in single-particle format within individual capture chambers of a chip, in order to isolate target material from individual target particles in a manner that facilitates further downstream processing. Block 410 can be implemented by an embodiment, variation, or example of the sample processing cartridge 130/sample processing chip 132 described above; however, Block 410 can additionally or alternatively include receiving a biological sample at any other suitable system configured to capture cells in at least one of single-cell format and single-cluster format (e.g., with co-capture of cell in single-cell format and one or more functional particles corresponding to each single cell).

In Block 410, a biological sample containing the target particles can be transmitted and/or received directly into an inlet of the chip (e.g., by pipetting, by fluid delivery through a fluid channel coupled to the array) for distribution across a set of wells of a capture region of the chip, and/or in any other suitable manner. Embodiments, variations, and examples of Block 410 can be implemented as described in one or more applications incorporated by reference above.

Block 420 recites: supporting an environment for processing target material of the set of particles within the capture region, according to a set of operations. Block 420 functions to create an environment whereby target material of the sample can be prepared for retrieval in coordination with application of an applied force, according to subsequent blocks of the method 400. As such, Block 420 can include creating physical environments (e.g., within chambers, with appropriate process reagents) for one or more of: lysing captured cells, disrupting membranes of captured cells; releasing target material (e.g., nucleic acid content) from captured cells; separating undesired elements (e.g., RNA, proteins) captured sample material; performing washing steps, co-capturing functional particles (e.g., non-magnetic beads, magnetic beads) with individually-captured cells and/or their target material; performing barcoding steps; attaching relevant adaptor molecules to released nucleic acid content; hybridizing target material (e.g., mRNA) to functional particles; performing reverse transcription; transmitting a retrieval buffer into the chip for preparation of target material for release from the capture region; sonicating or otherwise physically disturbing contents of the capture region for the chip for preparation of target material for release from the capture region; and/or performing any other suitable steps to enable efficient retrieval of target material from the capture region of the chip. As described in more detail below, specific steps for implementing magnetic force retrieval modes and/or gravity-associated retrieval modes can be performed.

Additionally or alternatively, embodiments, variations, and examples of Block 420 can be implemented as described in one or more applications incorporated by reference above.

4.2 Method—Magnetic Force Retrieval Modes

Related to embodiments, variations, and examples of the systems 200, 200' described above, the method 400 can include steps for retrieval of target material from the capture region of the sample processing chip, using magnetic force retrieval modes.

In particular, Block 430 recites: forming an assembly with an adaptor configured to couple to the substrate. Block 430 is preferably implemented by way of an embodiment, variation, or example of the adaptor 210, 210' described above, whereby the adaptor includes functionality for separating a magnet from physically contacting wells or other sensitive material at the capture region of the chip, and for transmitting forces associated with a magnetic field to the capture region for retrieval of target material of the chip. Forming the assembly can be facilitated through structural features of the chip and/or adaptor, as well as through use of guides or other support structures for retaining relative orientations between the chip and the adaptor during the process of delivering captured target material from the capture region of the chip for retrieval.

Block 440 recites: transmitting a force to the adaptor and the capture region, thereby releasing target material of the set of particles toward the adaptor. Block 440 functions to transmit force, in a controlled manner, to the capture region of the chip using the adaptor, in order to promote release of target material from the chip for retrieval. In relation to magnetic retrieval modes, the force is a magnetic force generated through use of a magnet (e.g., such as the magnets described above); however, the force can additionally or alternatively include another suitable force. Furthermore, the force is preferably applied as a pulling force in a direction perpendicular to a plane at which the set of wells is defined; however, the force can alternatively be oriented in any other suitable direction.

Block 450 recites: releasing target material of the set of particles for capture by the adaptor. Block 450 functions to promote transmission of target material (e.g., through use of coupled magnetic beads to functional particles to which target material is bound) toward the adaptor, in order to facilitate retrieval of target material from the chip in an efficient manner. Target material can then be extracted for further downstream processing.

Variations and examples of magnetic retrieval modes in association with Blocks 420-450 are further described in Section 4.2.1. below.

4.2.1 Magnetic Retrieval Method Variations and Examples

Figure 15B:
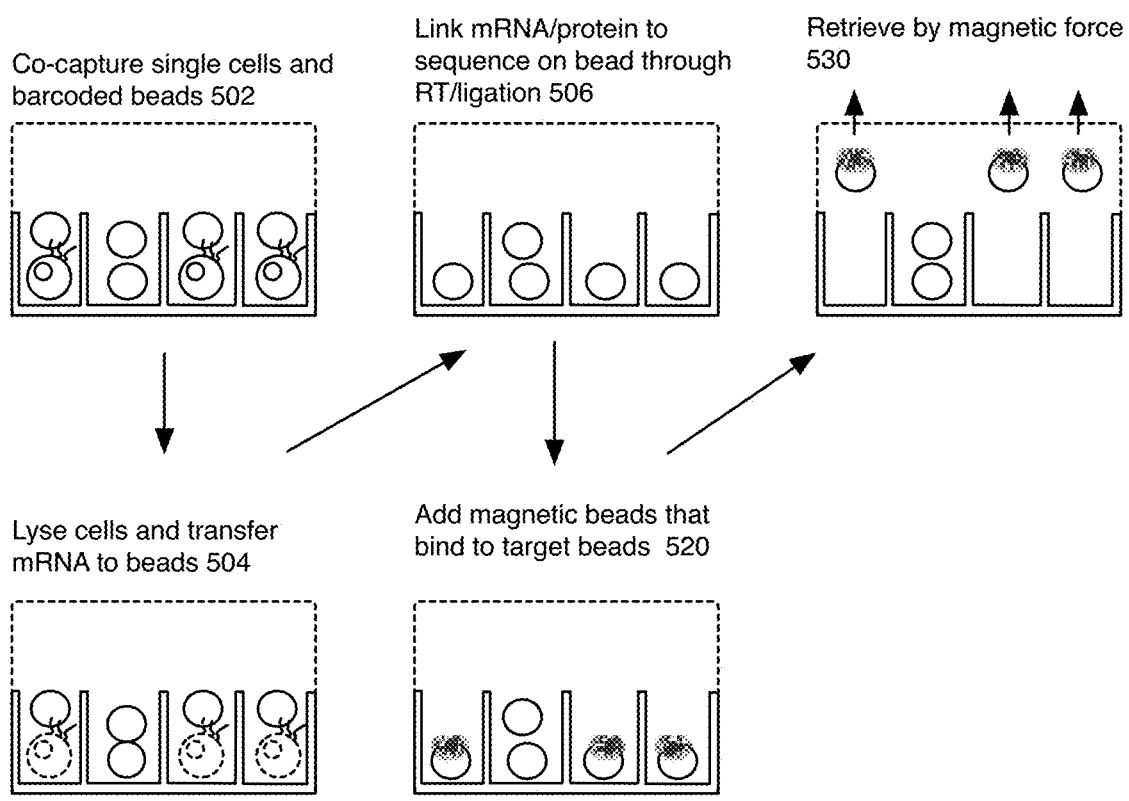

In particular, as shown in FIGS. 15A and 15B, variations of magnetic retrieval methods 500 can include steps for: Co-capturing single cells and barcoded beads within individual wells of the chip 502; Lysing cells and transferring mRNA from cells to its co-captured bead 504; linking captured mRNA/proteins to barcoded oligonucleotide sequence on beads through Reverse Transcriptase or ligation (where, during this process, only biotinylated TSO primer attaches to bead in a microwell that has a target cell) 506; thus binding biomarkers from single cells to functionalized non-magnetic beads, in single bead format within a set of wells of the chip 510; binding a set of magnetic particles (e.g., 0.5-3 micron particles) through specific interactions to the functionalized non-magnetic beads within the set of wells 520 (e.g., where biotinylayed magnetic beads, 0.5-3 micron, bind to target beads through streptavidin interactions and remaining excess bead are freely floating, laying on the floor or non-specifically bind to other beads); and using an adaptor, applying a magnetic force to the set of magnetic particles coupled to the captured target material (e.g., directly coupled to functionalized non-magnetic microspheres within the wells, directly coupled to target material using a molecular scissor process), for retrieval of target material from within the set of wells 530. Magnetic retrieval methods described can produce retrieval of target material in 5-8 minutes of manual operation time (and 15-45 minutes total time), with a retrieval efficiency of >90% where only magnetic particles coupled to target material of the sample are retrieved. Furthermore, magnetic retrieval methods can produce a reduction in reverse transcription-derived concatamers, provide an automation-friendly protocol, reduce number of splits required in downstream cDNA amplification, reduce the need for SPRI-based clean-up and size selection and reduce efforts and process reagent usage in downstream steps (e.g., associated with exonuclease treatment and cDNA amplification). Removal of exonuclease treatment steps in library preparation from single cells is very advantageous as any contamination of exonuclease enzymes to the instruments, lab bench and equipment used during one single cell preparation may inhibit the reactions used for subsequent single cell preparation for the next sample using the exonuclease contaminated elements.

Figure 16:
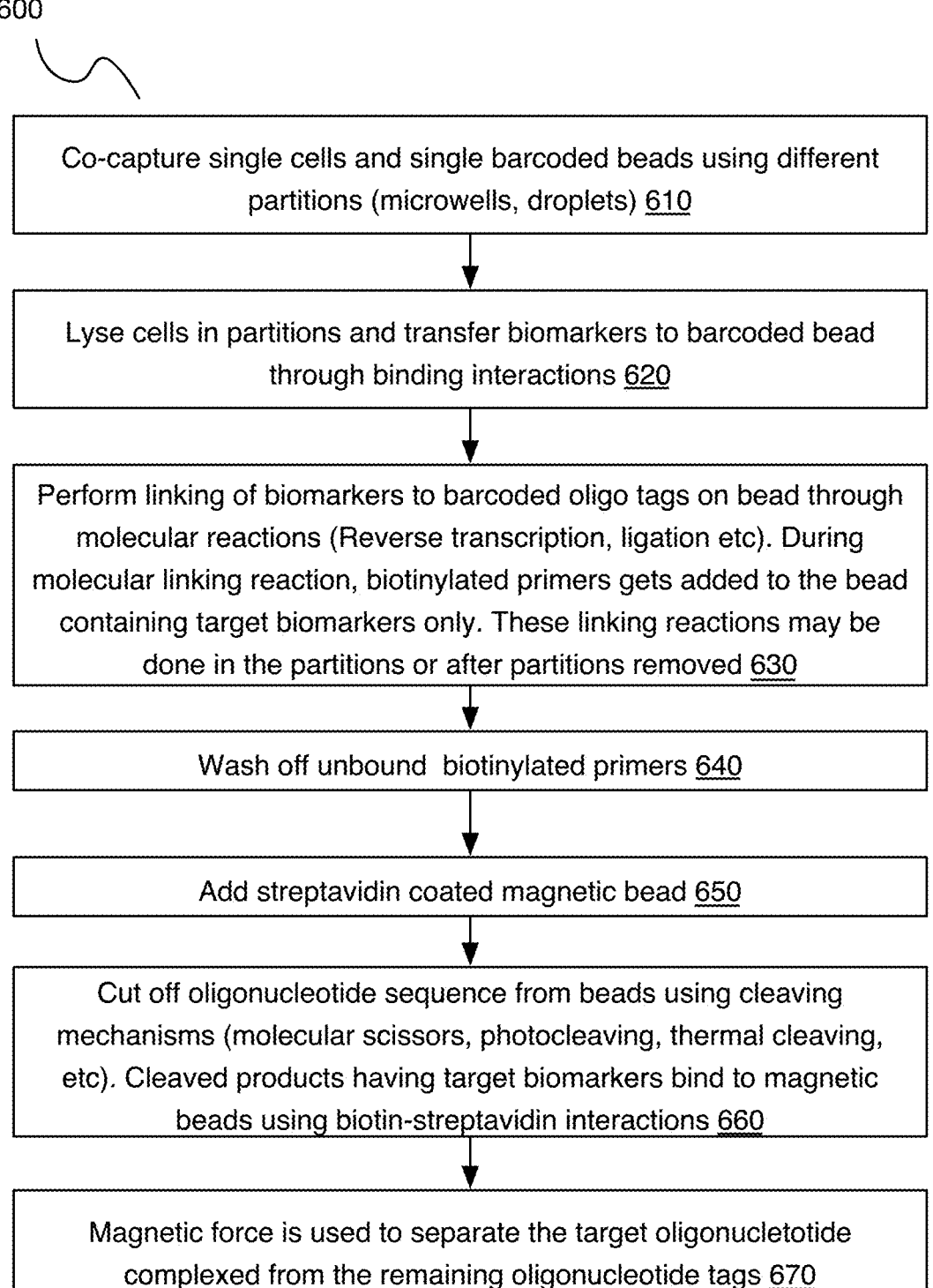

First Example: In a first example of the methods 400 and 500, magnetic forces can be transmitted to the chip, for enabling a mechanism for binding and selective removal of barcoded non-magnetic microspheres coupled to or otherwise containing mRNA products as target material from single cells originally captured at the chip. In more detail, as shown in FIG. 16, the method boo can include functionality for: co-capturing single cells and single barcoded beads using different partitions (microwells, droplets) 610; lysing cells in partitions and transfer biomarkers to barcoded bead through binding interactions 620; performing linking of biomarkers to barcoded oligo tags on bead through molecular reactions (Reverse transcription, ligation etc.), where during molecular linking reaction, biotinylated primers get added to the bead containing target biomarkers only and these linking reactions may be done in the partitions or after partitions removed 630; washing off unbound biotinylated primers 640; adding streptavidin coated magnetic beads 650; optionally cutting off oligonucleotide sequence from beads using cleaving mechanisms (e.g., molecular scissors, photocleaving, thermal cleaving, etc.), where cleaved products having target biomarkers bind to magnetic beads using biotin-streptavidin interactions 660; and using magnetic force to separate the target oligonucleotide complexed from the remaining oligonucleotide tags 670. Embodiments, variations, and examples of workflow aspects can be performed as described in relation to applications incorporated by reference above.

Figure 17A:
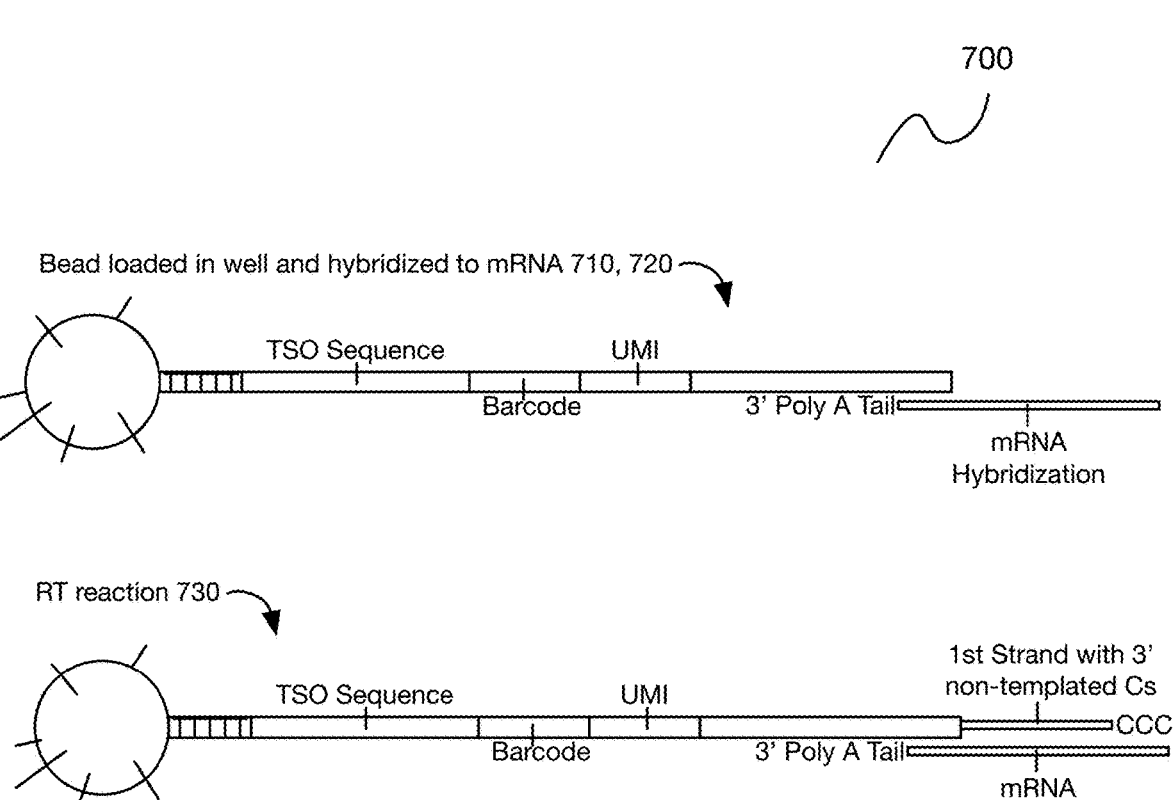

As shown in FIGS. 17A-17D, an example of the method 700 can include capturing functionalized non-magnetic beads in single-bead format 710, and hybridizing the functionalized non-magnetic beads to mRNA material from single cells captured contemporaneously in corresponding wells 720. As shown in FIG. 17A (top), hybridization can involve use of a molecule having a set of thymine (T) bases bound to the functionalized non-magnetic bead, a template switching oligonucleotide (TSO) sequence at a 5' end, a barcode sequence, a unique molecular identifier (UMI), and a tail at the 3' end.

Then, as shown in FIG. 17A (bottom) the first example of the method 600 can include performing a reverse transcription reaction (RT-reaction) with the target mRNA material, with a first molecule corresponding to the target mRNA molecule and having 3' end non-templated cytosine (C) bases 730. The RT-reaction thus incorporates a TSO containing a biotin tag at the 5' end. Following block 730, the method 700 can include washing steps for removing unbound biotinylated TSO primers, as described in applications incorporated by reference above.

Then, as shown in FIG. 17B, the first example of the method 600 can include implementing cDNA with a template switching oligonucleotide (TSO) sequence extension at the first strand having 3' end non-templated cytosine bases, for complete capture of 5' ends of the target material, using the template switching mechanism of a Moloney Murine Leukemia Virus (MMLV) RT enzyme 740. The cDNA TSO sequence extension corresponds with a Biotin TSO at the 5' end of the target mRNA.

Figure 17C:
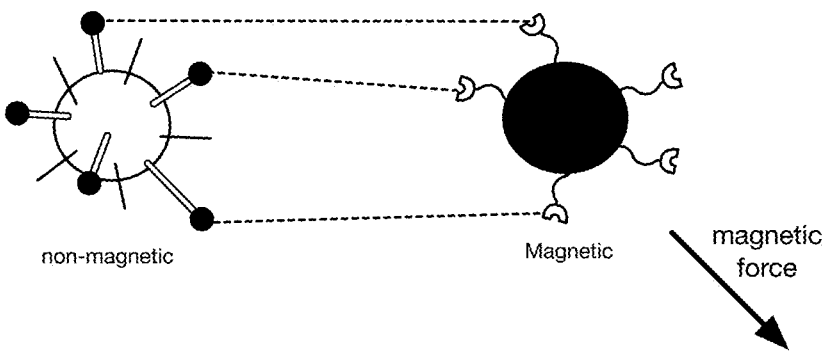
Figure 17D:
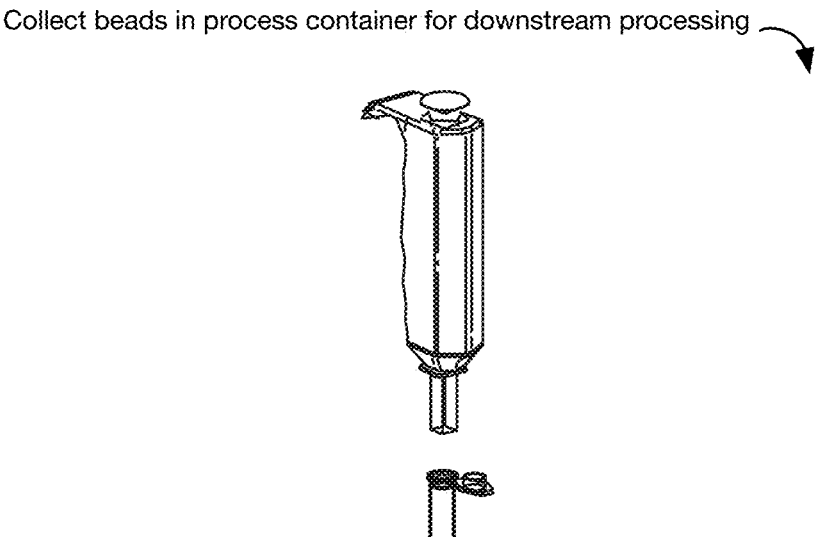

Then as shown in FIGS. 17B and 17C, the first example of the method 700 can include binding 750 the functionalized non-magnetic beads to magnetic streptavidin beads (e.g., dynabeads) at the 5' biotin end of the molecule produced in Block 740, by way of the biotyntilated TSO portion. In more detail, the magnetic streptavidin beads can be added to the capture chambers and mixed with contents with an incubation period (e.g., 20 minutes) before retrieval. As shown in FIG. 17C, the method 700 can further include applying an attractive magnetic force 660 to draw the bead complexes to the adaptor using an embodiment, variation, or example of the system 200 described above. As shown in FIG. 17D, captured bead complexes can then be transmitted to a container (e.g., tube) for further processing.

Second Example: In a second example of the methods 400 and 500, magnetic forces can be transmitted to the chip, for enabling a mechanism for binding and selective removal of barcoded nucleic acid material products as target material from single cells originally captured at the chip, while leaving functionalized non-magnetic particles at the chip during the retrieval process. In more detail, as shown in FIGS. 18A-18E, an example of the method Boo can include capturing functionalized non-magnetic beads in single-bead format, and hybridizing the functionalized non-magnetic beads to mRNA material from single cells captured contemporaneously in corresponding wells. Then, instead of retrieving functionalized non-magnetic beads from the chambers of the chip, the method Boo can implement molecular scissors (e.g., double stranded molecular scissor molecules, single stranded molecular scissor molecules) or photocleaving to release target cDNA-RNA hybrid for capture on secondary magnetic particles, for retrieval by applied magnetic force. Examples of molecular scissors include Btu Endonucleases that can specifically cut single started oligonucleotide sequence containing modified bases (e.g., deoxy-lUridine, dSpacer or deoxylnosine. Another example of molecular scissors include Urasil-specific Excision Reagent (USER) enzymes that can specifically cut single stranded oligonucleotide sequence containing modified base Uracil. In examples, the enzyme is activated at a temperature of ~37 C. Examples of photocleavable linkers (PC Linker) include a non-nucleosidic moiety that can be used to link two nucleotide sequences through a short UV photocleavable C3 spacer arm. Photo-cleavage of PC Linker by UV light yields one 5'-phosphorylated oligo and one 3'-phosphorylated oligo. This process can select for molecules containing products and reduce damage to target cDNA-RNA hybrids due to reduced stresses attributed to pulling a single bead type from a capture well, as opposed to pulling two bead types out of the wells).

In more detail, as shown in FIG. 18A (top), hybridization can involve use of a molecule having a set of thymine (T) bases (e.g., 5 or 10 T bases) bound to the functionalized non-magnetic bead, a modified base region having a set of modified, non-natural bases (e.g. dU as shown in FIG. 18A, top; dSpacer as shown in FIG. 18A, bottom) configured to be targeted by a molecular scissor (e.g., that operates with a or ultraviolet photocleaving mechanism, that operates with another mechanism), template switching oligonucleotide (TSO) sequence, a barcode sequence, a unique molecular identifier (UMI), and a tail at the 3' end.

The second example of the method 700 can include Blocks 830 and 840 (shown in FIGS. 18B and 18C), analogous to Blocks 730 and 740 described above, for performing a RT reaction and a TSO process for complete capture of 5' ends of target material using an MMLV RT enzyme.

Then, as shown in FIG. 18C, the second example of the method Boo can include releasing the target RNA-cDNA hybrids into the wells of the capture region of the chip 850 by restricting the bead-oligonucleotides at the modified base region, using single or double stranded molecular scissors.

Figure 18D:
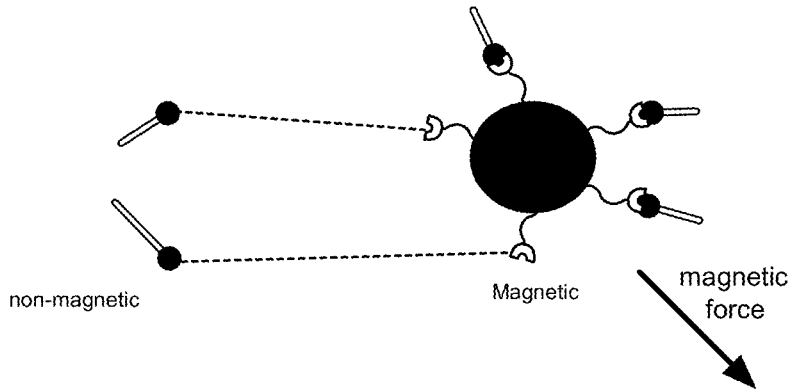
Figure 18E:
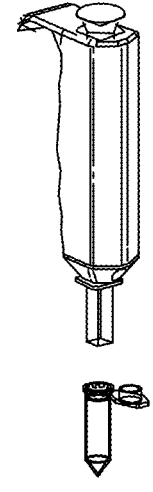

Then, as shown in FIGS. 18C and 18D, the second example of the method Boo can include binding released target RNA-cDNA hybrids to magnetic streptavidin beads at the 5' biotin end of the molecule produces in Block 840. As shown in FIG. 18D, the method Boo can further include applying an attractive magnetic force 860 to draw the bead complexes to the adaptor using an embodiment, variation, or example of the system 200 described above. As shown in FIG. 18E, captured bead complexes can then be transmitted to a container (e.g., tube) for further processing.

While examples are described above, any other suitable target material (e.g., non-mRNA material) can be processed using other enzymes (e.g., non-MMLV enzymes), other transcription processes, and/or any other suitable processes.

4.3 Method—Gravity-Associated Force Retrieval Modes

Related to embodiments, variations, and examples of the system 300 described above, the method 400 can include steps for retrieval of target material from the capture region of the chip, using gravity-associated force retrieval modes.

In particular, Block 430 recites: forming an assembly with an adaptor configured to couple to the substrate. Block 430 is preferably implemented by way of an embodiment, variation, or example of the adaptor described above, whereby the adaptor includes functionality for defining an internal cavity into which target material can be aggregated with application of an applied force to the assembly. Forming the assembly can be facilitated through structural features of the chip and/or adaptor, as well as through use of guides or other support structures for retaining relative orientations between the chip and the adaptor during the process of delivering captured target material from the capture region of the chip for retrieval.

Block 440 recites: transmitting a force to the adaptor and the capture region, thereby releasing target material of the set of particles into the adaptor. Block 440 functions to transmit force, in a controlled manner, to the capture region of the chip, in order to promote release of target material from the chip and into the adaptor for retrieval. In relation to gravity-associated force retrieval modes, the force is a centrifugal force generated through use of a centrifuge apparatus; however, the force can additionally or alternatively include another suitable force.

Block 450 recites: releasing target material of the set of particles into the adaptor. Block 450 functions to promote transmission of target material toward the adaptor, in order to facilitate retrieval of target material from the adaptor in an efficient manner. Target material can then be extracted for further downstream processing.

Variations and examples of centrifugation-associated retrieval modes in association with Blocks 420-450 are further described in Section 4.3.1. below.

4.3.1 Centrifugation-Associated Retrieval Method Variations and Examples

Figure 19:
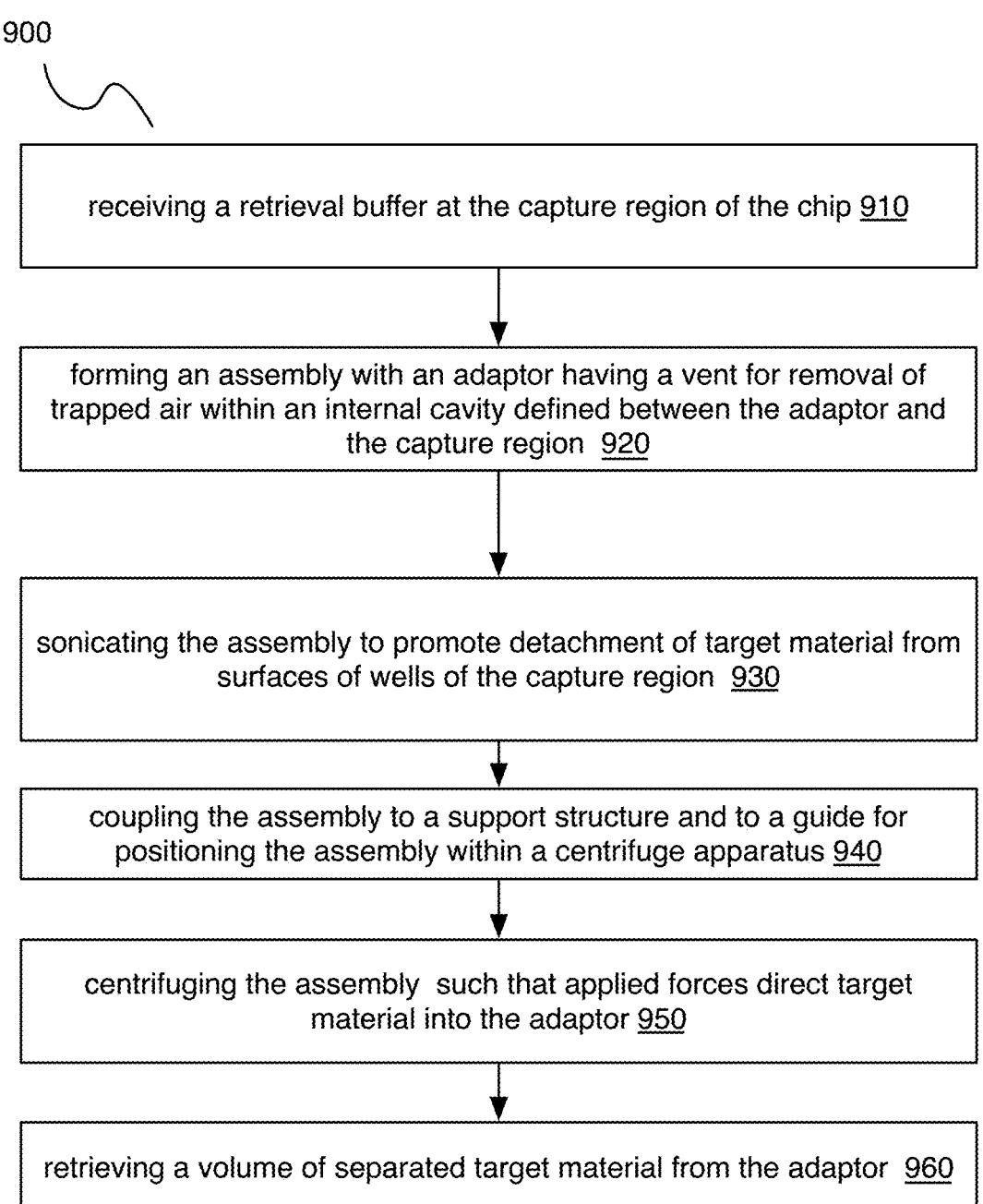

In particular, as shown in FIG. 19, variations of centrifugation retrieval methods 900 can include steps for: receiving a retrieval buffer at the capture region of the chip 910 (e.g., with filling of the wells and blocking inlet and outlet ports of the sample processing chip with plugs); forming an assembly with an adaptor having a vent for removal of trapped air within an internal cavity defined between the adaptor and the capture region 920 (e.g., with attachment of the adaptor and applying pressure to remove any trapped air); sonicating the assembly (e.g., at 47 kHz, at another frequency) to promote detachment of target material from surfaces of wells of the capture region 930; coupling the assembly to a support structure and to a guide for positioning the assembly within a centrifuge apparatus 940; centrifuging the assembly (e.g., at woo relative centrifugal field) such that applied forces direct target material into the adaptor 950; and retrieving a volume (e.g., pellet) of separated target material from the adaptor 960 (e.g., using retrieval buffer delivered through a fluidic network of the sample processing chip).

Centrifugation-based retrieval methods can rapidly produce retrieval of target material in 2-3 minutes of manual operation time (and ~15 minutes total time), with a retrieval efficiency of ~85-95%.

5. CONCLUSION

The FIGURES illustrate the architecture, functionality and operation of possible implementations of systems, methods and computer program products according to preferred embodiments, example configurations, and variations thereof. In this regard, each block in the flowchart or block diagrams may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A method for retrieval and processing of material from a sample, the method comprising:

coupling a first magnet to an adaptor of a separation subsystem, the first magnet supported by a pipette interface, wherein the adaptor comprises an internal cavity comprising first and second regions, wherein the second region includes a vent to atmosphere;

establishing fluid communication between the first region of the adaptor and a capture region of a capture substrate containing material derived from the sample, wherein the capture region comprises a plurality of high-aspect ratio wells, and wherein target material is retained at individual wells of the capture region;

applying a magnetic force to contents of the capture substrate, through the adaptor, by way of the first magnet, thereby transferring a volume of target material from the capture substrate to the adaptor;

with the separation subsystem comprising a gantry, displacing the adaptor from the capture substrate;

transporting the adaptor, with the volume of target material, into a separation reservoir of a process container;

performing a washing operation, within the separation reservoir, thereby separating non-target material from the volume of target material; and transferring the volume of target material from the separation reservoir to another substrate.

2. The method of claim 1, wherein the target material is attached to magnetic particles.

3. The method of claim 1, wherein the target material is derived from single cells.

4. The method of claim 1, wherein the target material is nucleic acid.

5. The method of claim 1, wherein the target material is protein.

6. The method of claim 1, wherein the plurality of high-aspect ratio wells are arranged in hexagonal close packing configuration.

7. The method of claim 2, wherein one or more wells of the plurality of wells contain target material bound to magnetic particles.

8. The method of claim 1, wherein the separation subsystem comprises a support structure coupled to the gantry for displacing the adaptor from the capture substrate.

* * * * *